US 7,010,869 B1

(12) United States Patent
Ellis, III

(10) Patent No.: US 7,010,869 B1
(45) Date of Patent: Mar. 14, 2006

(54) SHOE SOLE ORTHOTIC STRUCTURES AND COMPUTER CONTROLLED COMPARTMENTS

(75) Inventor: Frampton E. Ellis, III, 2895 S. Abingdon St., Suite B2, Arlington, VA (US) 22206-1331

(73) Assignee: Frampton E. Ellis, III, Jasper, FL (US)

( * ) Notice: Subject to any disclaimer, the term of this patent is extended or adjusted under 35 U.S.C. 154(b) by 638 days.

(21) Appl. No.: 09/558,629

(22) Filed: Apr. 26, 2000

Related U.S. Application Data

(63) Continuation-in-part of application No. 09/358,848, filed on Jul. 22, 1999, now abandoned.
(60) Provisional application No. 60/139,319, filed on Jun. 15, 1999, provisional application No. 60/138,624, filed on Jun. 11, 1999, provisional application No. 60/133,114, filed on May 7, 1999, provisional application No. 60/131,255, filed on Apr. 27, 1999, and provisional application No. 60/130,990, filed on Apr. 26, 1999.

(51) Int. Cl.
*A43B 17/00* (2006.01)
*A43B 19/00* (2006.01)
*A43B 7/14* (2006.01)
*A61F 5/14* (2006.01)

(52) U.S. Cl. .............................. 36/25 R; 36/88; 36/101; 36/100; 36/146; 36/161; 36/10

(58) Field of Classification Search ................. 36/25 R, 36/29, 32 R, 43, 22 R, 30 R, 31, 100, 101, 36/15, 103, 7.1 R, 7.2, 7.4, 7.7, 146, 161, 36/163, 88, 117.1, 117.4, 10
See application file for complete search history.

(56) References Cited

U.S. PATENT DOCUMENTS 597,524 A 1/1898 Molloy et al.

3,005,272 A 10/1961 Shelare et al.
4,263,728 A 4/1981 Frecentese (Continued)

FOREIGN PATENT DOCUMENTS

| EP | 0 679 377 | 11/1995 |
|---|---|---|
| EP | 0 864 263 | 9/1998 |
| WO | 9000358 | 1/1990 |

(Continued)

OTHER PUBLICATIONS

Converse advertisement in box of shoes purchased in 1999, *Coming Spring 2000—Helium Cross Training*, 1 page.
L.L. Bean Catalog, Summer 1992, p. 122, Catalog entry for Birkenstock Sandals for Men and Women.

(Continued)

*Primary Examiner*—Anthony D. Stashick
(74) *Attorney, Agent, or Firm*—Knoble Yoshida & Dunleavy, LLC

(57) ABSTRACT

This invention relates generally to footwear with a shoe sole, including at least one insertable midsole orthotic. The insertable midsole orthotic is removably inserted within the shoe upper, the sides of which hold it in position. The shoe sole includes a concavely rounded side or underneath portion, which may be formed in part by the insertable midsole orthotic. The insertable midsole orthotic may extend the length of the shoe sole or may form only a part of the shoe sole and can incorporate cushioning or structural compartments or components.

The insertable midsole orthotic permits replacement of midsole material which has degraded or has worn out in order to maintain optimal characteristics of the shoe sole and allows customization for the individual wearer to provide tailored cushioning or support characteristics for the purpose of orthopedic, podiatric, corrective, prescriptive, therapeutic and/or prosthetic purposes.

29 Claims, 63 Drawing Sheets

U.S. PATENT DOCUMENTS

| | | | |
|---|---|---|---|
| 4,506,461 A | | 3/1985 | Inohara |
| 4,510,700 A | | 4/1985 | Brown |
| 4,513,518 A | | 4/1985 | Jalbert et al. |
| 4,513,520 A | | 4/1985 | Koch |
| 4,597,196 A | | 7/1986 | Brown |
| 4,610,099 A | | 9/1986 | Signori |
| 4,615,126 A | | 10/1986 | Mathews |
| 4,669,142 A | | 6/1987 | Meyer |
| 4,709,316 A | * | 11/1987 | Tanzi ............................. 36/55 |
| D293,275 S | | 12/1987 | Bua |
| 4,718,179 A | | 1/1988 | Brown |
| 4,790,082 A | * | 12/1988 | Pozzebon ...................... 36/10 |
| 4,843,741 A | | 7/1989 | Yung-Mao |
| 4,845,863 A | | 7/1989 | Yung-Mao |
| 4,852,273 A | | 8/1989 | Hamy |
| 4,868,945 A | | 9/1989 | DeBettignies |
| 4,881,328 A | | 11/1989 | Yung-Mao |
| 4,934,072 A | | 6/1990 | Fredericksen et al. |
| 4,989,349 A | | 2/1991 | Ellis, III |
| 5,042,175 A | | 8/1991 | Ronen et al. |
| 5,152,081 A | | 10/1992 | Hallenbeck et al. |
| 5,315,767 A | * | 5/1994 | Bradbury ................... 36/7.1 R |
| 5,317,819 A | | 6/1994 | Ellis, III |
| RE34,890 E | * | 4/1995 | Sacre ............................. 36/55 |
| 5,410,821 A | | 5/1995 | Hilgendorf |
| 5,425,186 A | * | 6/1995 | Hoyt ........................ 36/7.1 R |
| 5,469,639 A | | 11/1995 | Sessa |
| 5,509,217 A | | 4/1996 | Condini |
| 5,544,429 A | | 8/1996 | Ellis, III |
| 5,659,979 A | | 8/1997 | Sileo |
| 5,727,334 A | | 3/1998 | Cougar |
| 5,813,142 A | | 9/1998 | Demon |
| 5,822,888 A | | 10/1998 | Terry |
| 5,855,079 A | * | 1/1999 | Herbert ......................... 36/10 |
| 5,893,222 A | * | 4/1999 | Donnelly ...................... 36/55 |
| 5,909,948 A | | 6/1999 | Ellis, III |
| 5,937,542 A | | 8/1999 | Bourdeau |
| 5,970,630 A | | 10/1999 | Gallegos |
| 6,000,704 A | * | 12/1999 | Balbinot ...................... 36/100 |
| 6,023,857 A | | 2/2000 | Vizy et al. |
| 6,092,311 A | | 7/2000 | MacNamara |
| 6,115,941 A | | 9/2000 | Ellis, III |
| 6,115,945 A | | 9/2000 | Ellis, III |
| 6,163,982 A | | 12/2000 | Ellis, III |

FOREIGN PATENT DOCUMENTS

| | | |
|---|---|---|
| WO | WO 91/00698 | 1/1991 |
| WO | 9103180 | 3/1991 |
| WO | 9104683 | 4/1991 |
| WO | 9105491 | 5/1991 |
| WO | 9110377 | 7/1991 |
| WO | 9111124 | 8/1991 |
| WO | 9111924 | 8/1991 |
| WO | 9119429 | 12/1991 |
| WO | 9207483 | 5/1992 |
| WO | 9218024 | 10/1992 |
| WO | 9403080 | 2/1994 |
| WO | WO 97/00029 | 1/1997 |
| WO | 9746127 | 12/1997 |
| WO | 9807341 | 2/1998 |
| WO | WO 00/64293 | 11/2000 |
| WO | WO 01/80678 | 11/2001 |

OTHER PUBLICATIONS

Runner's World, Apr. 1992, Advertisement for "Teva. The Sport Sandal.", 1 page.

L.L. Bean Catalog, 1992, Catalog entry for Cradlefoot Beach Sandal, 1 page.

* cited by examiner

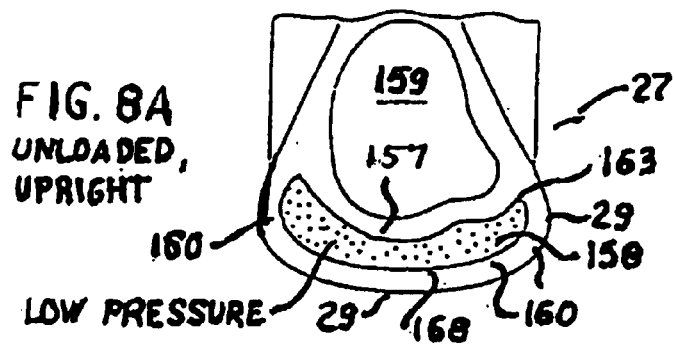
FIG. 8A UNLOADED, UPRIGHT
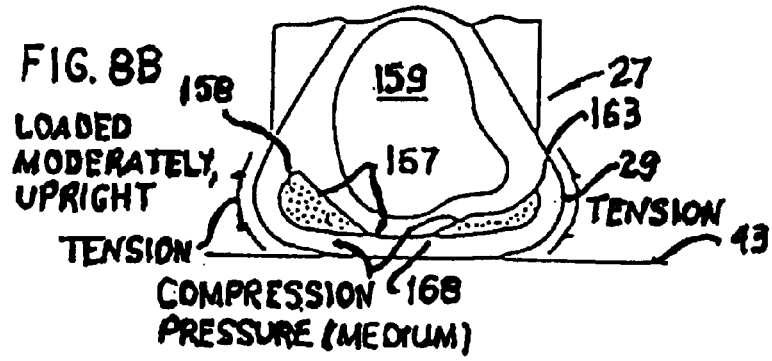
FIG. 8B LOADED MODERATELY, UPRIGHT
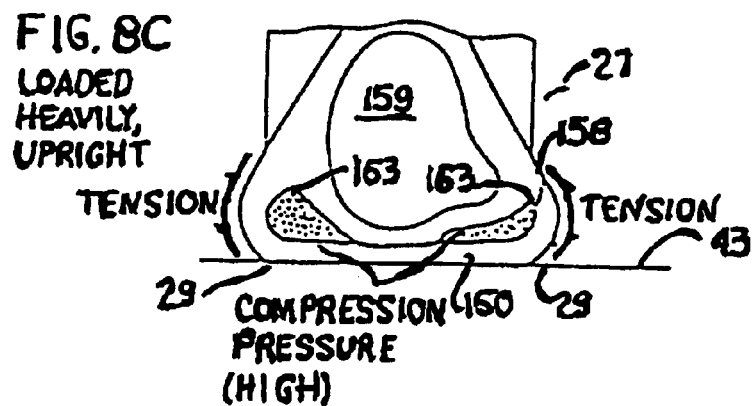
FIG. 8C LOADED HEAVILY, UPRIGHT
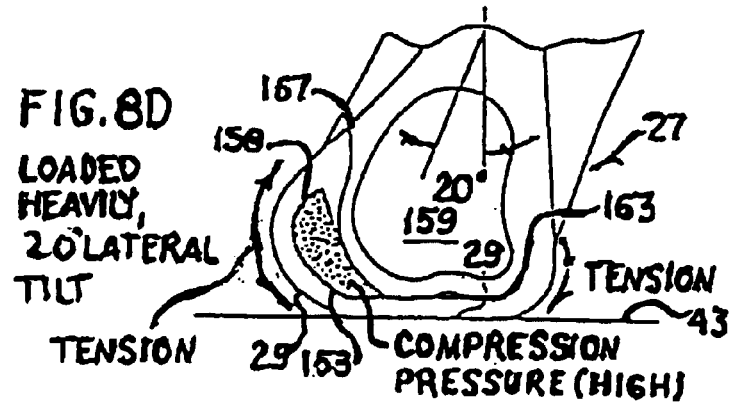
FIG. 8D LOADED HEAVILY, 20° LATERAL TILT

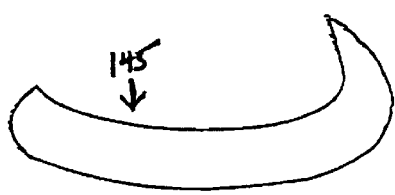
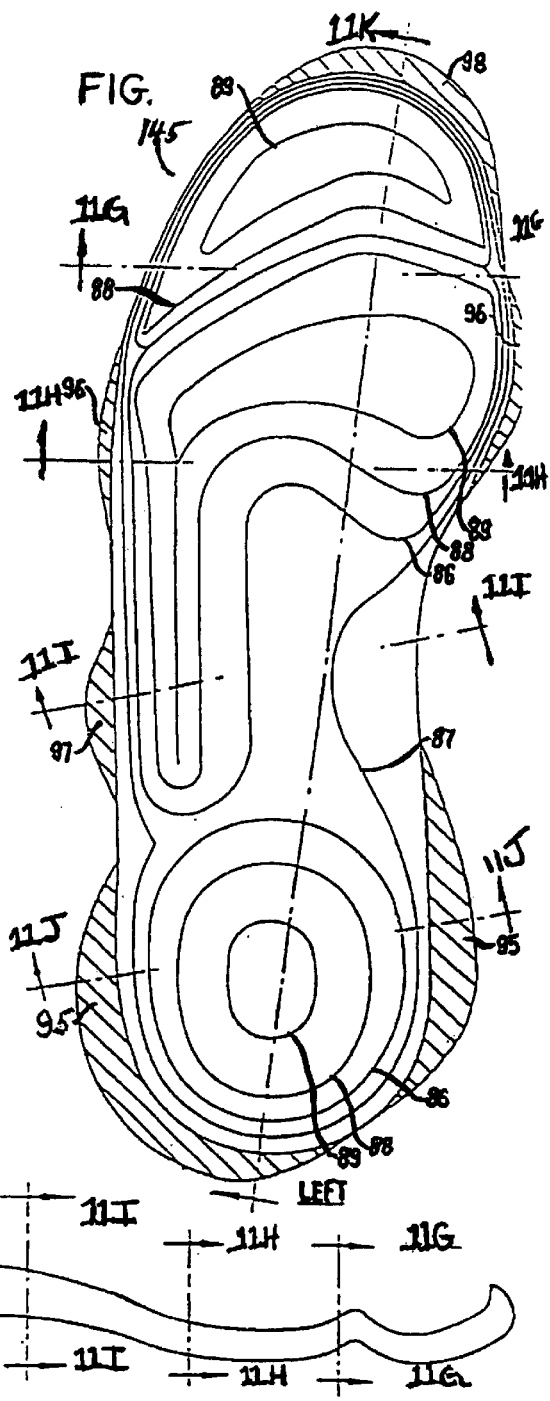
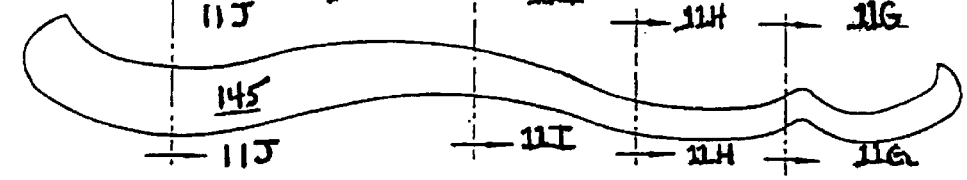

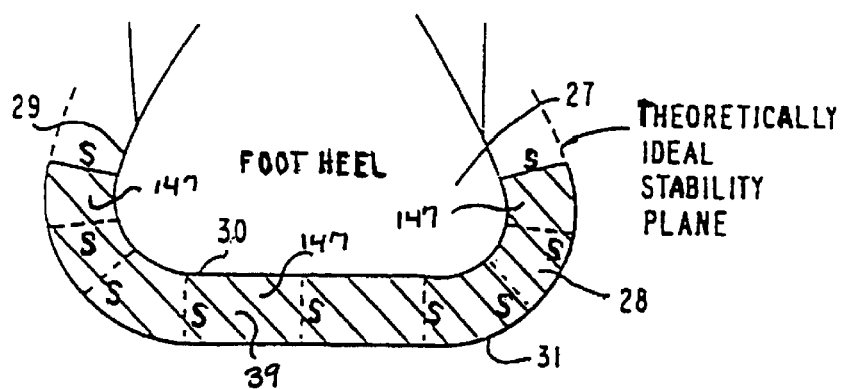
FIG. 29
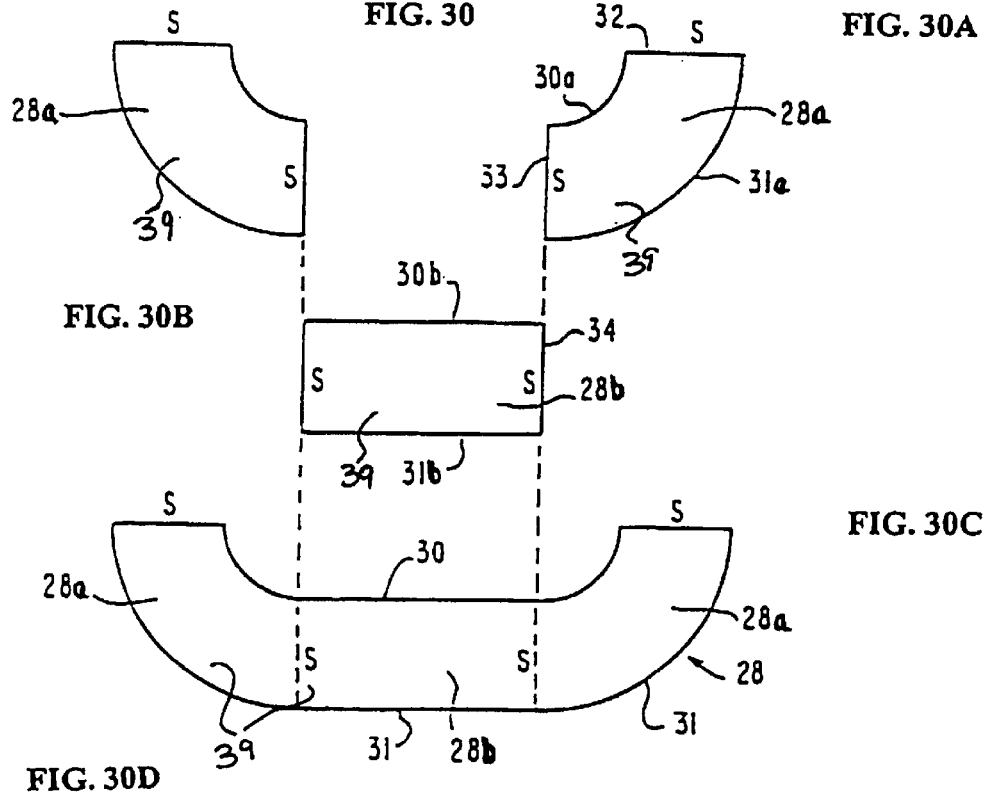
FIG. 30  FIG. 30A
FIG. 30B
FIG. 30C
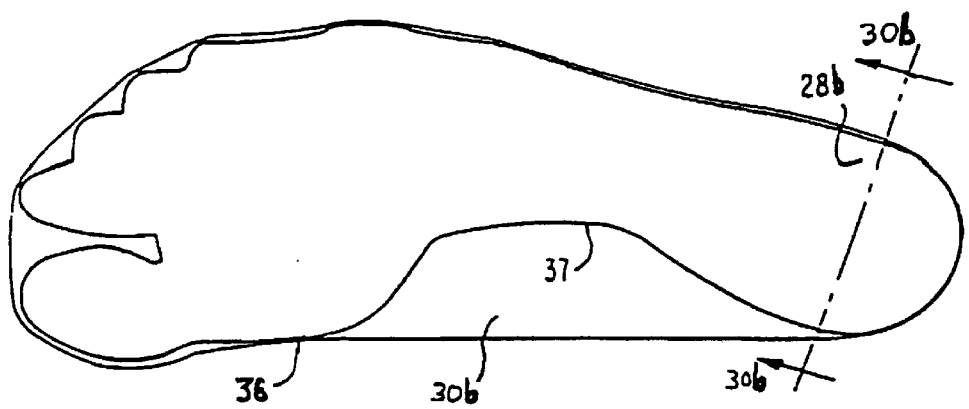
FIG. 30D FIG. 31
FIG. 31A
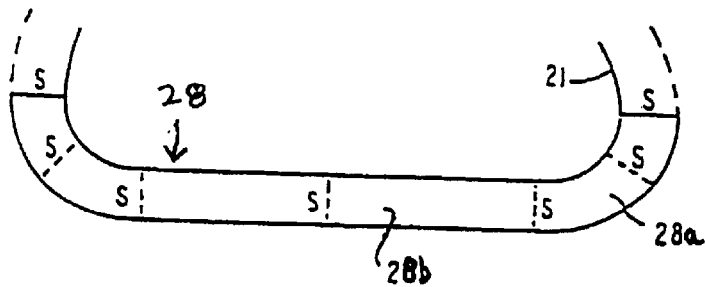
FIG. 31B
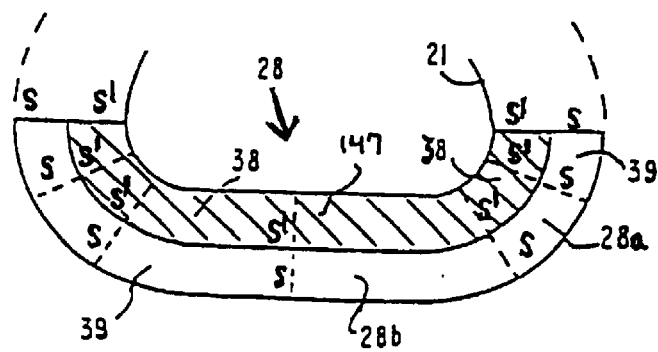
FIG. 32
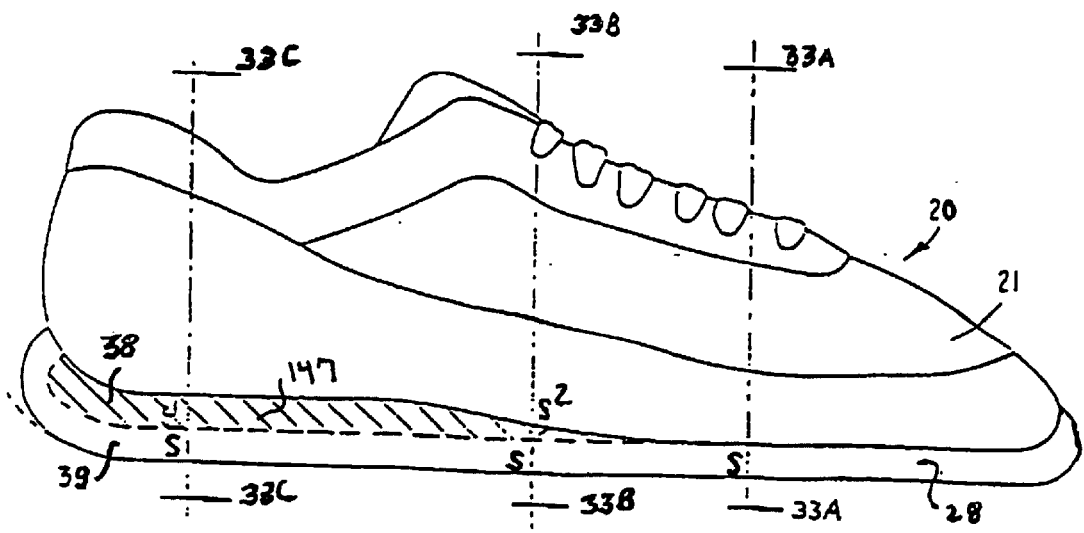

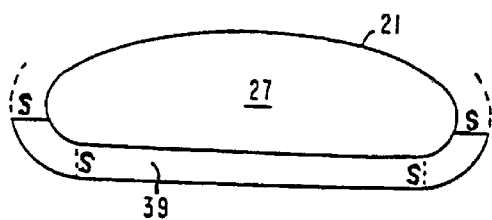
FIG. 33A
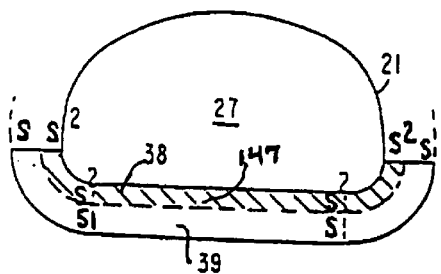
FIG. 33B
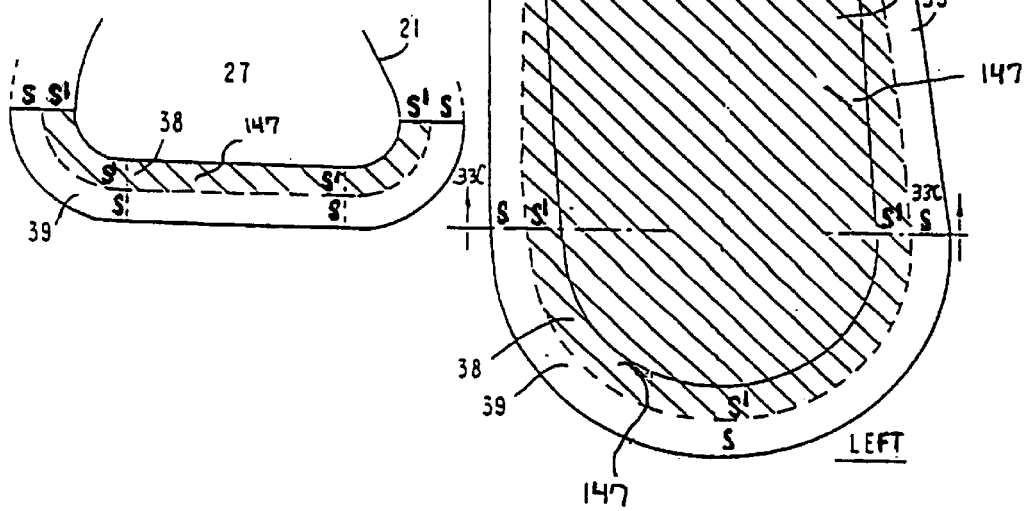
FIG. 33C
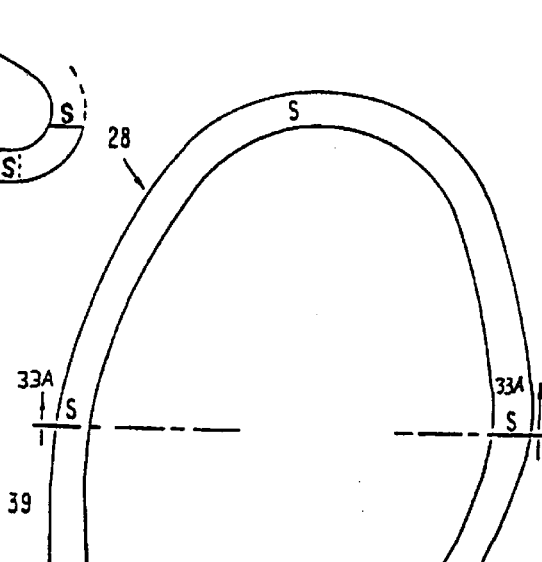
FIG. 33
FIG. 33D FIG. 34A
FIG. 34
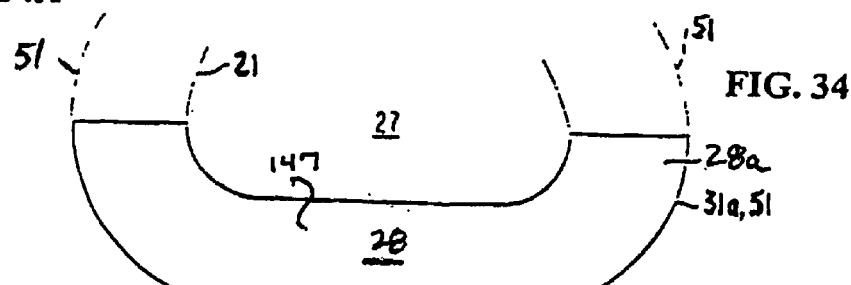
FIG. 34B
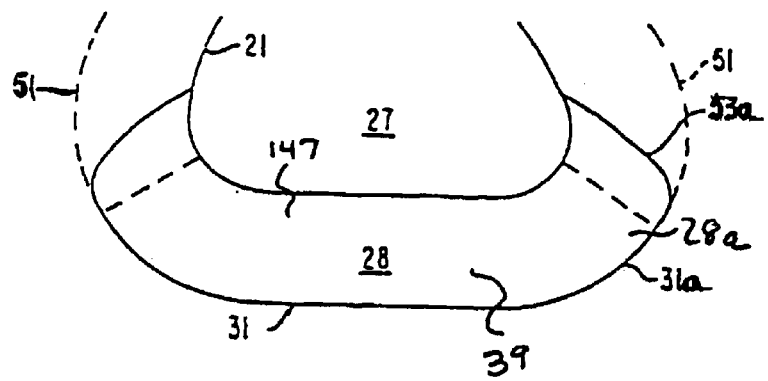
FIG. 34C
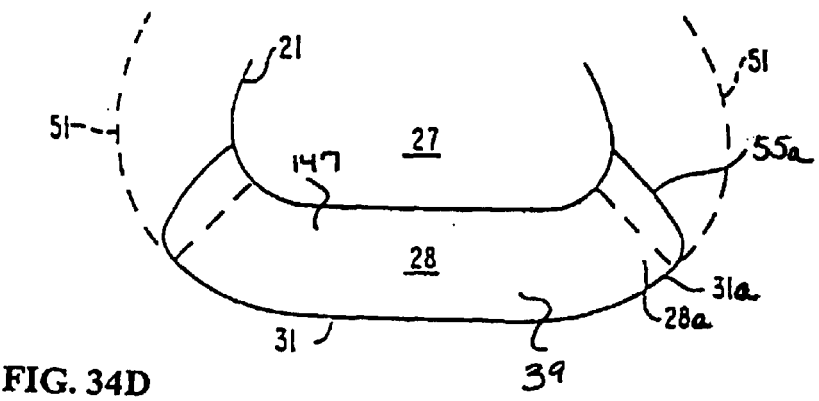
FIG. 34D
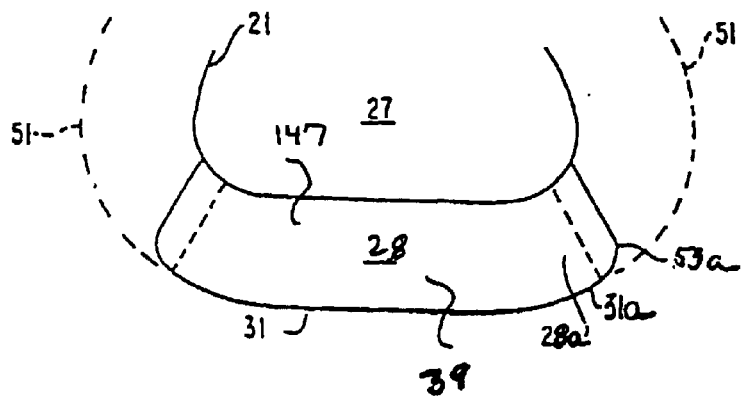

FIG. 35
FIG. 35A
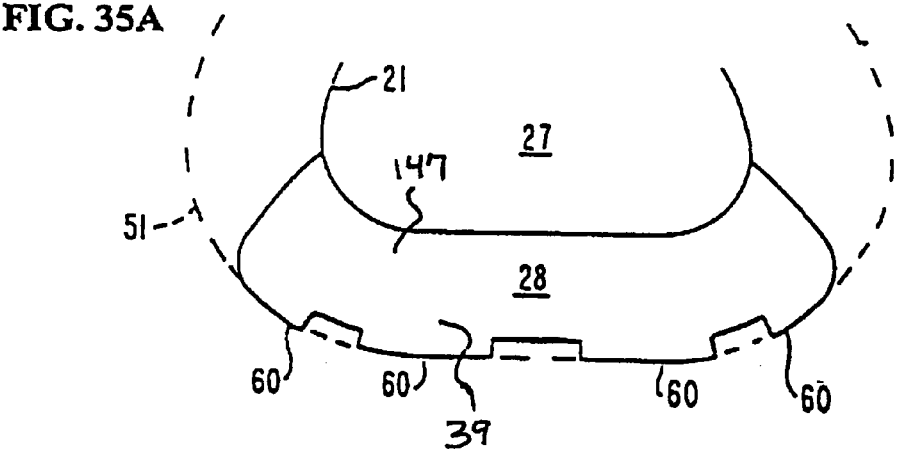
FIG. 35B
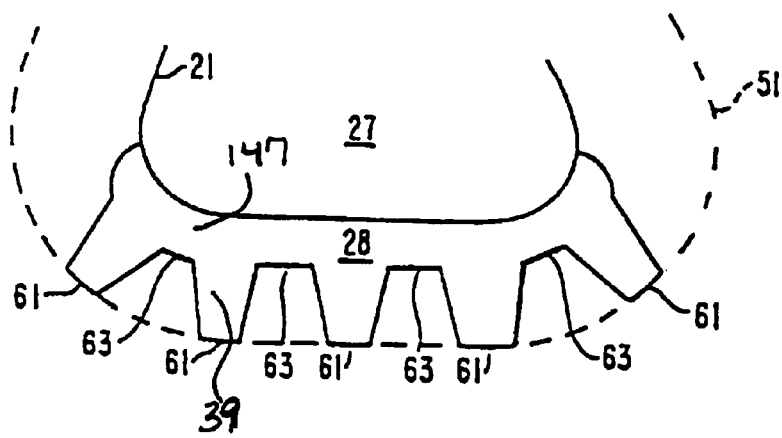
FIG. 35C
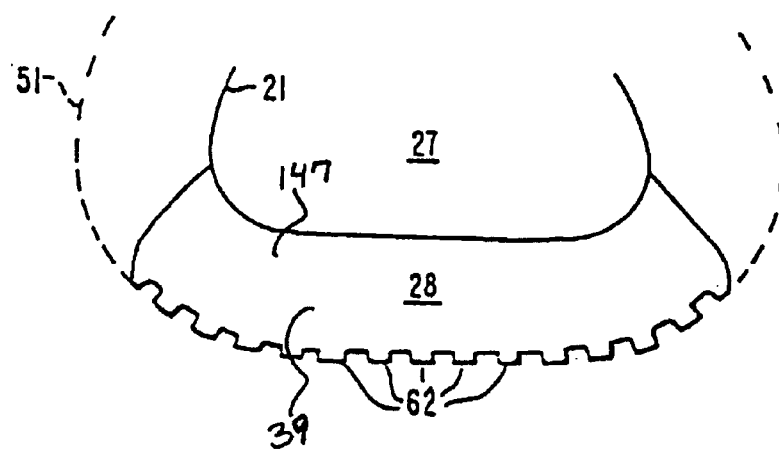

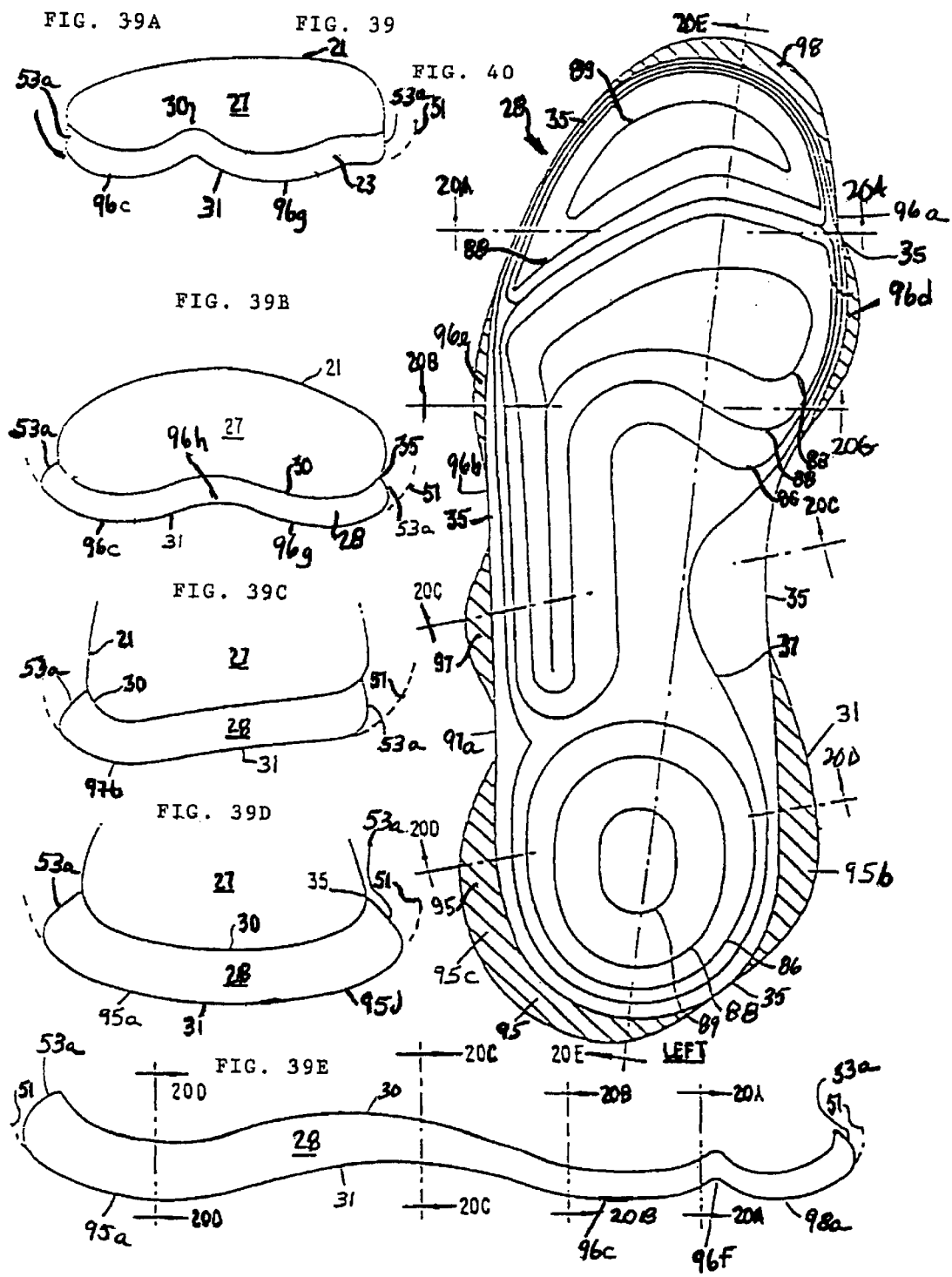

FIG. 41
FIG. 41A
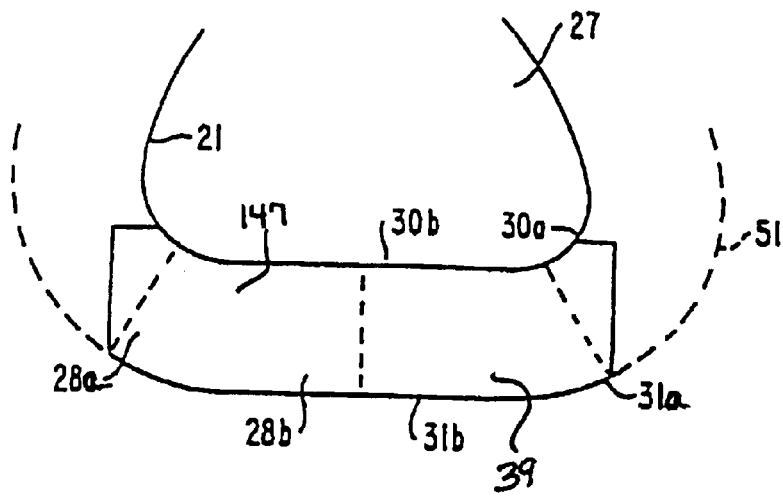
FIG. 41B
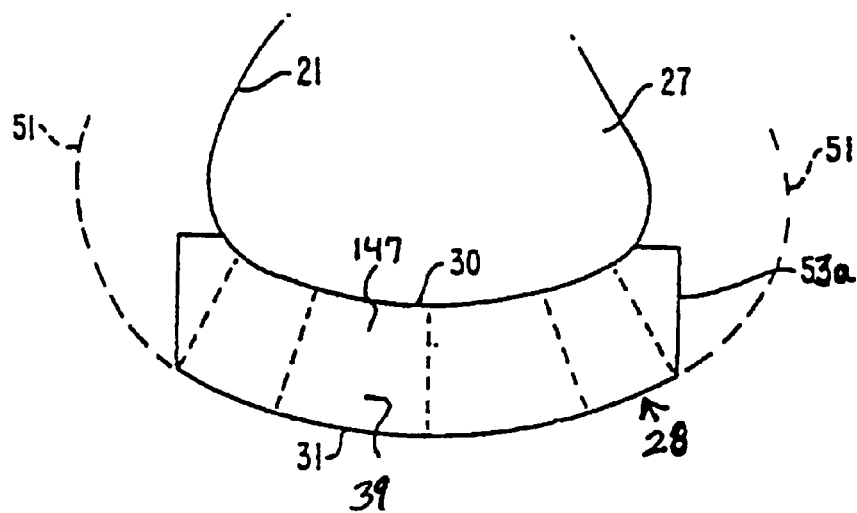

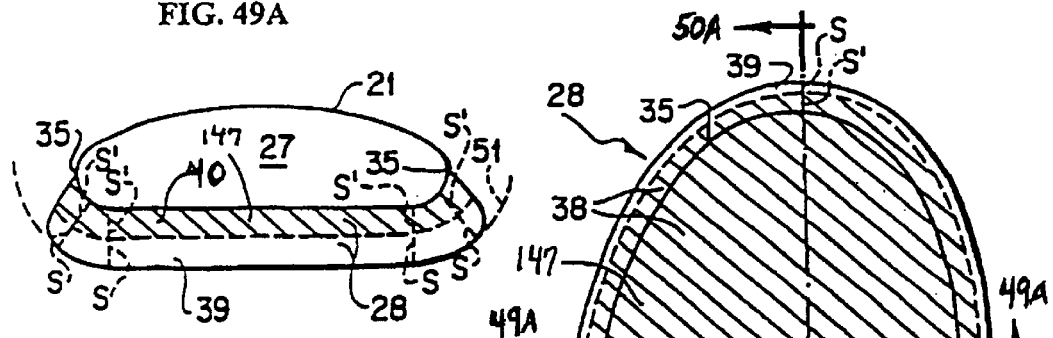
FIG. 49A
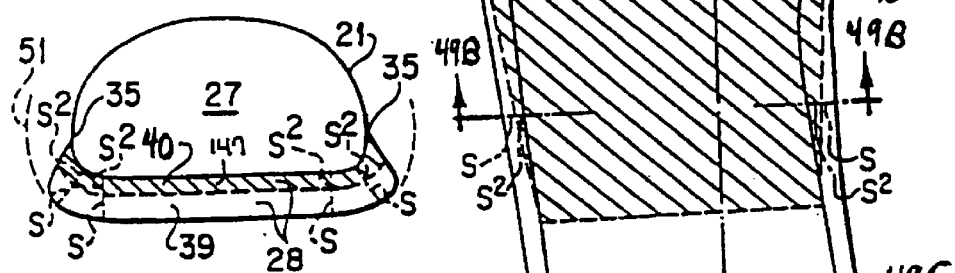
FIG. 49B
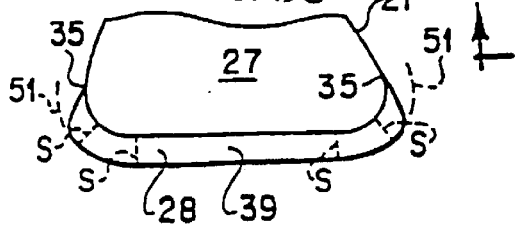
FIG. 49C
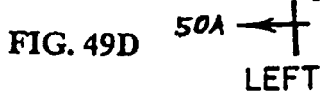
FIG. 49D  LEFT

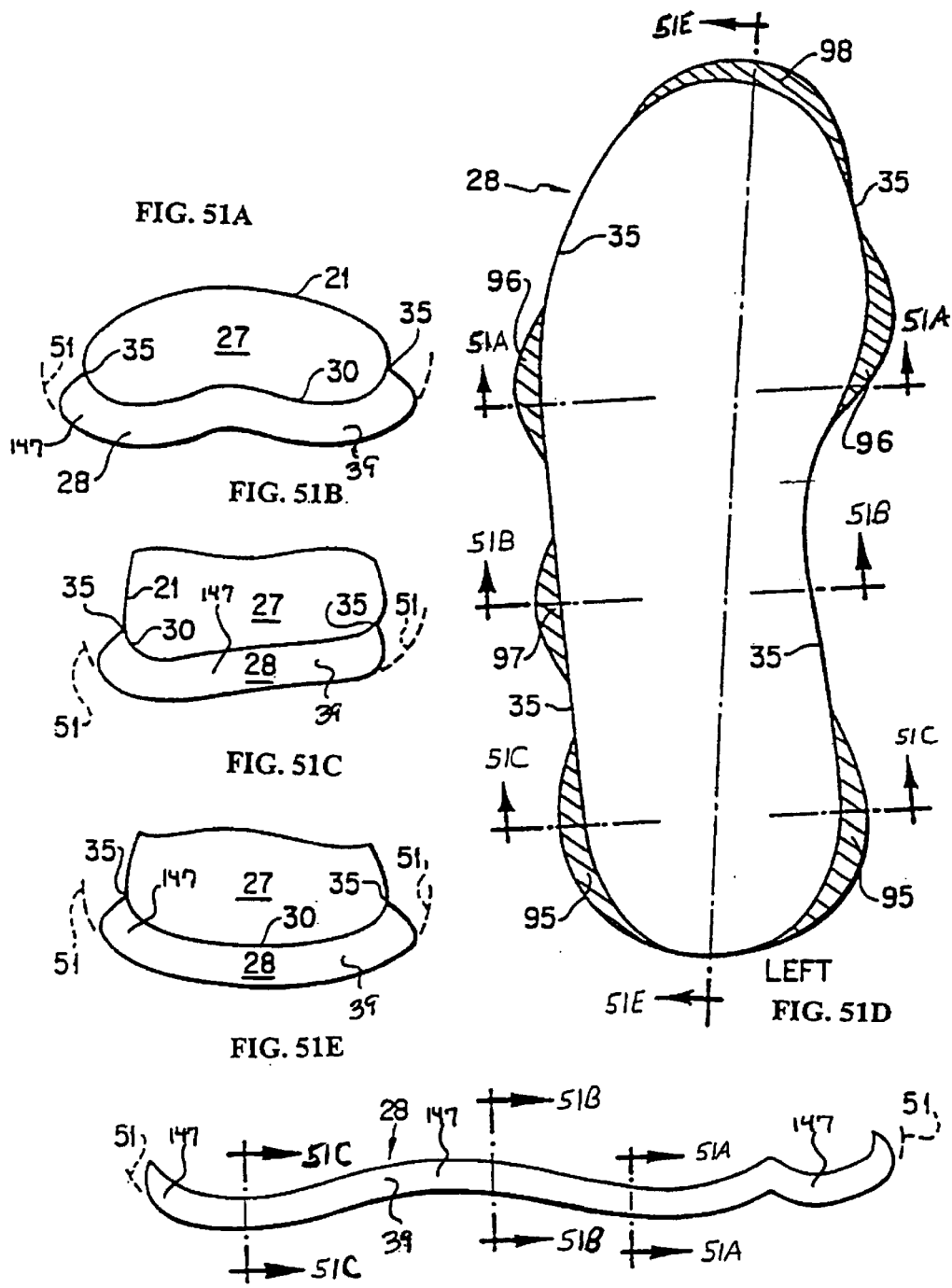

FLAT FOOTPRINT  TILTED OUT 20°  TILTED OUT 20°

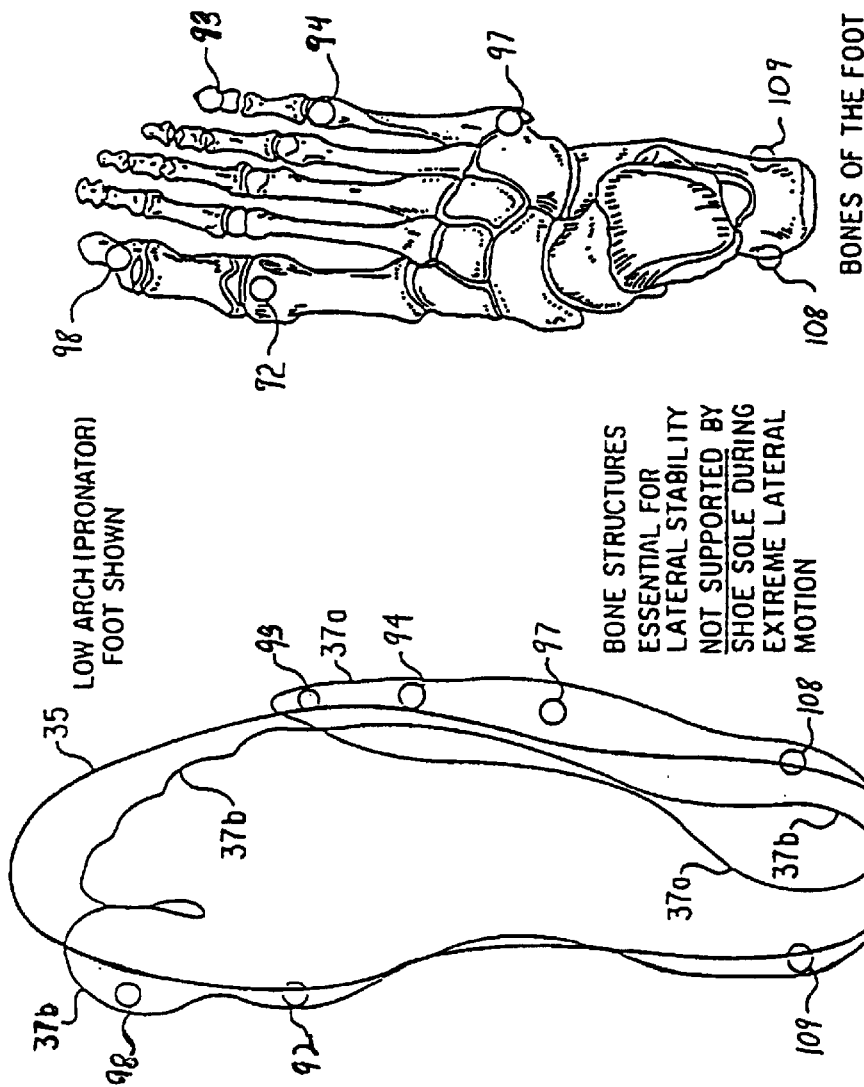

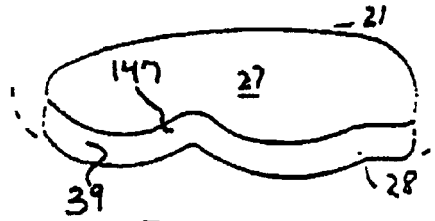
FIG. 67A
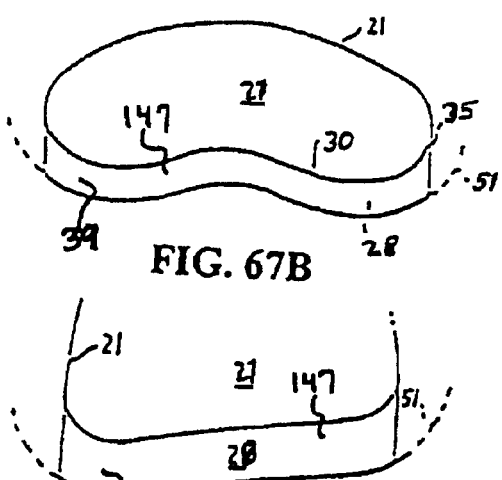
FIG. 68
FIG. 67B
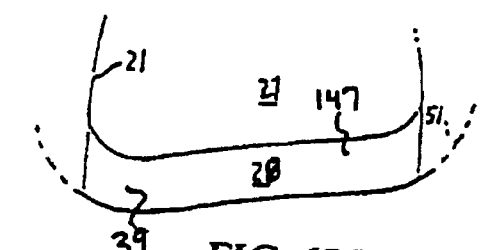
FIG. 67C
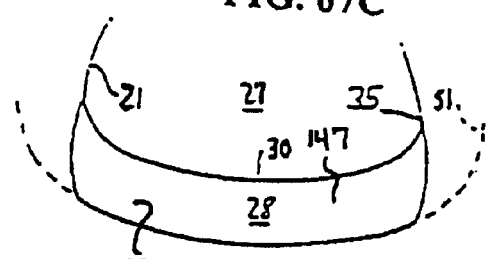
FIG. 67D
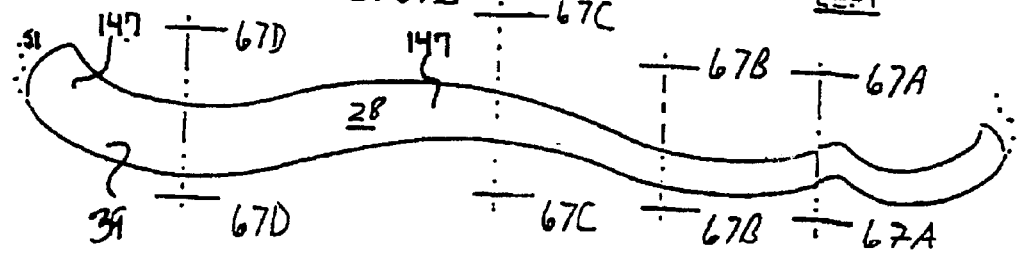
FIG. 67E

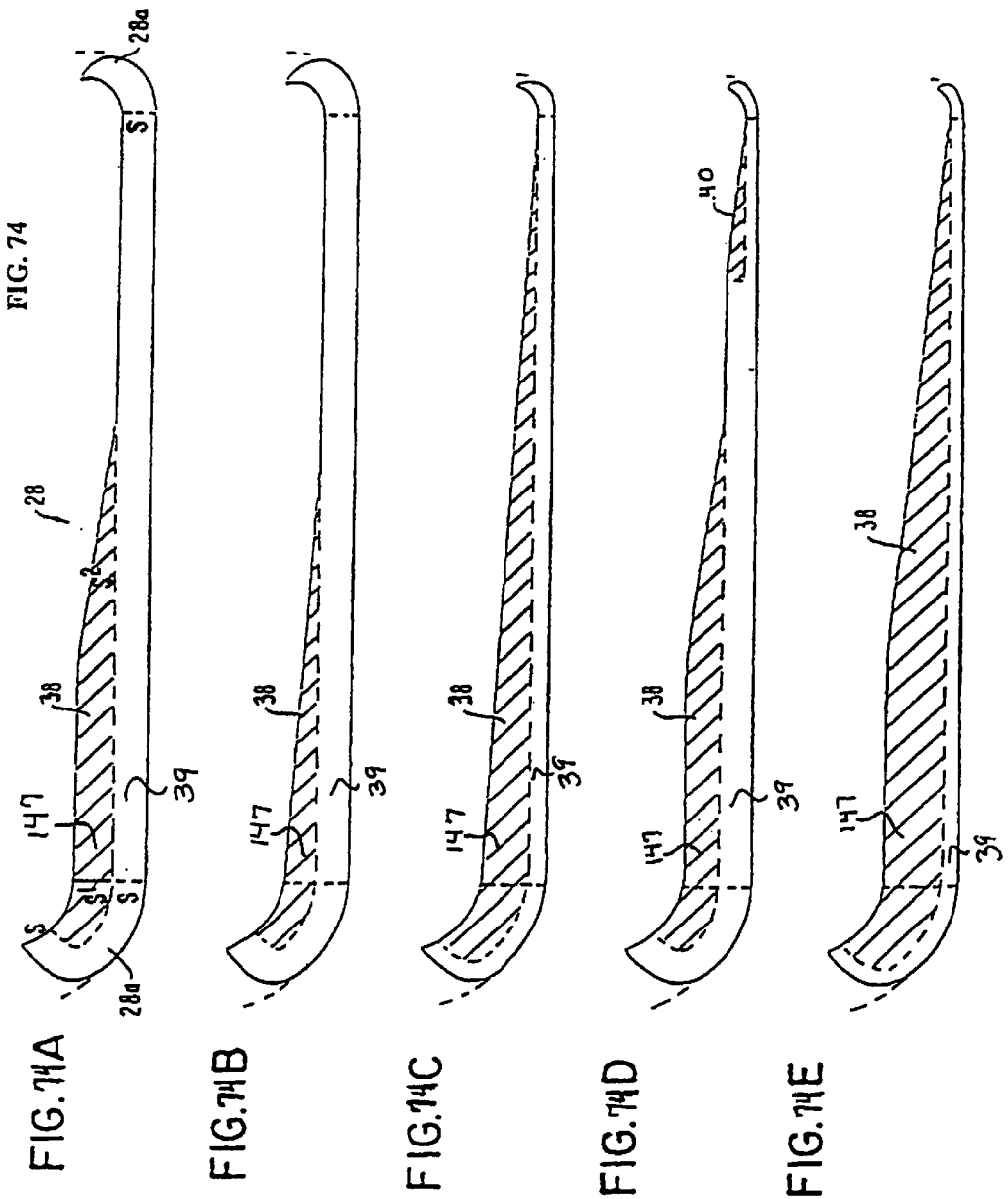

SHOE SOLE ORTHOTIC STRUCTURES AND COMPUTER CONTROLLED COMPARTMENTS

This application is a continuation-in-part of U.S. patent application Ser. No. 09/358,848, filed on Jul. 22, 1999, now abandoned which claims the benefit under 35 U.S.C. § 119(e) of U.S. provisional application No. 60/139,319, filed on Jun. 15, 1999, U.S. provisional application No. 60/138,624, filed on Jun. 11, 1999, U.S. provisional application No. 60/133,114, filed on May 7, 1999, U.S. provisional application No. 60/131,255, filed on Apr. 27, 1999, and U.S. provisional application No. 60/130,990, filed on Apr. 26, 1999.

BACKGROUND OF THE INVENTION

1. Field of the Invention

This invention relates generally to footwear such as a shoe, including an athletic shoe, with a shoe sole, including at least one orthotic insert formed at least in part by a midsole section (hereinafter referred to as an "insertable midsole orthotic"). The insertable midsole orthotic is preferably removable and is inserted within the shoe upper, the sides of which hold it in position, as may the bottom sole or other portion of the midsole. The shoe sole includes a concavely rounded side or underneath portion, which may be formed in part by the insertable midsole orthotic. The insertable midsole orthotic may extend the length of the shoe sole or may form only a part of the shoe sole and can incorporate cushioning or structural compartments or components. The insertable midsole orthotic provides the capability to permit replacement of midsole material which has degraded or has worn out in order to maintain optimal characteristics of the shoe sole. Also, the insertable midsole orthotic allows customization for the individual wearer to provide tailored cushioning or support characteristics for orthopedic, podiatric, corrective, prescriptive, therapeutic and/or prosthetic purposes. Finally, the insertable midsole orthotic can be employed or modified to provide an orthotic inner shoe.

The invention further relates to a shoe sole which includes at least one insertable midsole orthotic, at least one chamber or compartment containing a fluid, a flow regulator, a pressure sensor to monitor the compartment pressure, and a control system capable of automatically adjusting the pressure in the chamber or compartment(s) in response to the impact of the shoe sole with the ground surface, including embodiments which accomplish this function through the use of a computer such as a microprocessor.

2. Brief Description of the Prior Art

Many existing athletic shoes are unnecessarily unsafe. Many existing shoe designs seriously impair or disrupt natural human biomechanics. The resulting unnatural foot and ankle motion caused by such shoe designs leads to abnormally high levels of athletic injuries.

Proof of the unnatural effect of many existing shoe designs has come quite unexpectedly from the discovery that, at the extreme end of its normal range of motion, the unshod bare foot is naturally stable and almost impossible to sprain, while a foot shod with a conventional shoe, athletic or otherwise, is artificially unstable and abnormally prone to ankle sprains. Consequently, most ordinary ankle sprains must be viewed as largely an unnatural phenomena, even though such ankle sprains are fairly common. Compelling evidence demonstrates that the stability of bare feet is entirely different from, and far superior to, the stability of shod feet.

The underlying cause of the nearly universal instability of shoes is a critical but correctable design problem. That hidden problem, so deeply ingrained in existing shoe designs, is so extraordinarily fundamental that it has remained unnoticed until now. The problem is revealed by a novel biomechanical test, one that may be unprecedented in its extreme simplicity. The test simulates a lateral ankle sprain while standing stationary. It is easily duplicated and may be independently verified by anyone in a minute or two without any special equipment or expertise. The simplicity of the test belies its surprisingly convincing results. It demonstrates an obvious difference in stability between a bare foot and a foot shod with an athletic shoe, a difference so unexpectedly noticeable that the test proves beyond doubt that many existing shoes are unstable and thus unsafe.

The broader implications of this discovery are potentially far-reaching. The same fundamental problem in existing shoes that is glaringly exposed by the new test also appears to be the major cause of chronic overuse injuries, which are unusually common in running, as well as other chronic sport injuries. Existing shoe designs cause the chronic injuries in the same way they cause ankle sprains; that is, by seriously disrupting natural foot and ankle biomechanics.

The applicant has introduced into the art the concept of a Theoretically Ideal Stability Plane as a structural basis for shoe sole designs. That concept, as implemented into shoes such as street shoes and athletic shoes, is presented in U.S. Pat. No. 4,989,349, issued on Feb. 5, 1991; U.S. Pat. No. 5,317,819, issued Jun. 7, 1994; and U.S. Pat. No. 5,544,429, issued on Aug. 13, 1996, as well as in PCT Application No. PCT/US89/03076 filed on Jul. 14, 1989 and published as WO 90/00358, and many subsequent U.S. and PCT published applications.

The purpose of the Theoretically Ideal Stability Plane as described in these applications is primarily to provide a neutral shoe design that allows for natural foot and ankle biomechanics without the serious interference from the shoe design that is inherent in many existing shoes.

In a second aspect, the shoe sole designs in this application are based on a recognition that lifetime use of existing shoes, the unnatural design of which is innately and seriously problematic, has produced actual structural changes in the human foot and ankle. Existing shoes thereby have altered natural human biomechanics in many, if not most, individuals to an extent that must be compensated for in an enhanced and therapeutic design. The continual repetition of serious interference with natural biomechanics by existing shoes appears to have produced individual biomechanical changes that may be permanent, so simply removing the cause is not enough. Treating the residual effect must also be undertaken.

Some attempts have been made to provide footwear which is anatomically correct so as to increase the comfort of the wearer while at the same time minimizing fatigue and injuries caused by the design of many existing shoes. For example, orthotic devices are well known in the art and are exemplified by U.S. Pat. No. 4,803,707 issued to Brown and U.S. Pat. No. 4,868,945 issued to DeBettignies. Some of these designs are based on an analysis of the typical human gait. For example, U.S. Pat. No. 4,510,700 to Brown ("Brown '700") provides a detailed discussion of the various phases of the human gait. In Brown '700, a plurality of different types of orthotic devices are provided from which an appropriate device can be selected based on the particular foot disorder to be treated. Brown '700 accomplishes this with the provision of variably adjustable shoe inserts.

A number of other patents disclose orthotic devices which may be suitably positioned within the shoe. These devices include complex contours on their upper surfaces which are specially designed to address the peculiarities of a given foot. Examples of such devices are disclosed in U.S. Pat. Nos. 2,669,814; 2,680,919; and 3,922,801.

Accordingly, it is a general object of one or more embodiments of this it invention to elaborate upon the application of the principle of the natural basis for the support, stability, and cushioning of the barefoot to shoe designs.

It is still another object of one or more embodiments of the invention to provide a shoe having a sole with natural stability which puts the side of the shoe upper under tension in reaction to destabilizing sideways forces on a tilting shoe.

It is still another object of one or more embodiments of this invention to balance the tension force on the side of the shoe upper substantially in equilibrium to neutralize the destabilizing sideways motion by virtue of the tension in the sides of the shoe upper.

It is another object of one or more embodiments of the invention to create a shoe sole with support and cushioning which is provided by shoe sole compartments, filled with a pressure-transmitting medium like liquid, gas, or gel, that are similar in structure to the fat pads of the foot, which simultaneously provide both firm support and progressive cushioning.

A further object of one or more embodiments of the invention is to elaborate upon the application of the principle of the Theoretically Ideal Stability Plane to other shoe structures.

A still further object of one or more embodiments of the invention is to provide a shoe having a sole rounded which deviates in a constructive way from the Theoretically Ideal Stability Plane.

A still further object of one or more embodiments of this invention to provide a sole rounded having a shape naturally rounded to the shape of a human foot, but having a shoe sole thickness which is increased somewhat beyond the thickness specified by the Theoretically Ideal Stability Plane, either through most of the rounded of the sole, or at pre-selected portions of the sole.

It is yet another object of one or more embodiments of the invention to provide a naturally rounded shoe sole having a thickness which approximates a Theoretically Ideal Stability Plane, but which varies toward either a greater or lesser thickness throughout the sole or at pre-selected portions thereof.

It is another object of one or more embodiments of the present invention to implement one or more of the foregoing objects by employing a removable midsole orthotic.

It is yet another object of one or more embodiments of the present invention to combine one or more of the foregoing objects with the ability to customize the shoe design for a particular wearer's foot.

It is a still further object of one or more embodiments of the present invention to combine one or more of the foregoing objects with the ability to replace one or more portions of the shoe in order to substitute new portions for worn portions or for the purpose of customizing the shoe design for a particular activity.

It is a still further object of one or more embodiments of the present invention to provide the ability to automatically adjust various properties of the shoe or shoe sole using a computer controlled compartment system.

It is a still further object of one or more embodiments of the present invention to provide an orthotic inner shoe formed from a combination of one or more elements of the insertable midsole orthotic and/or computer controlled compartment system.

These and other objects of the invention will become apparent from the summary and detailed description of the invention which follow, taken with the accompanying drawings.

SUMMARY OF THE INVENTION

In one aspect, the present invention attempts, as closely as possible, to replicate the naturally effective structures of the bare foot that provide stability, support, and cushioning. More specifically, the invention relates to the structure of removable orthotic inserts formed at least in part by a midsole section and integrated into shoes such as athletic shoes. Even more specifically, this invention relates to the provision of a shoe having an anthropomorphic sole including a removable midsole orthotic that substantially copies the underlying support, stability and cushioning structures of the human foot. Natural stability is provided by balancing the tension force on the side of the upper in substantial equilibrium so that destabilizing sideways motion is neutralized by the tension.

Still more particularly, this invention relates to support and cushioning which is provided by shoe sole compartments filled with a pressure-transmitting medium like liquid, gas, or gel. Unlike similar existing systems, direct physical contact occurs between the upper surface and the lower surface of the compartments, providing firm, stable support. Cushioning is provided by the pressure-transmitting medium progressively causing tension in the flexible and semi-elastic sides of the shoe sole. The compartments providing support and cushioning are similar in structure to the fat pads of the foot, which simultaneously provide both firm support and progressive cushioning.

Directed to achieving the aforementioned objects and to overcoming problems with prior art shoes, a shoe according to one or more embodiments of the invention comprises a sole having at least a portion thereof which is naturally rounded whereby the upper surface of the sole does not provide an unsupported portion that creates a destabilizing torque and the bottom surface does not provide an unnatural pivoting edge.

In another aspect, the shoe includes a naturally rounded sole structure exhibiting natural deformation which closely parallels the natural deformation of a foot under the same load. The shoe sole is naturally rounded, paralleling the shape of the foot in order to parallel its natural deformation, and made from a material which, when under load and tilting to the side, deforms in a manner which closely parallels that of the foot of its wearer, while retaining nearly the same amount of contact of the shoe sole with the ground as in its upright state under load.

In another aspect, this invention relates to variations in the structure of such shoes having a sole contour which follows a Theoretically Ideal Stability Plane as a basic concept, but which deviates therefrom to provide localized variations in natural stability. This aspect of the invention may be employed to provide variations in natural stability for an individual whose natural foot and ankle biomechanical functioning have been degraded by a lifetime use of problematic existing shoes.

This new invention is a modification of the inventions disclosed and claimed in the applicant's previously mentioned prior patent applications and develops the application of the concepts disclosed therein to other shoe structures. In this respect, one or more of the features and/or concepts disclosed in the applicant's prior applications may be implemented in the present invention by the provision of a removable midsole orthotic. Alternatively, one or more of the features and/or concepts of the present invention may be combined with the provision of a removable midsole orthotic which itself may or may not implement one of the concepts disclosed in the applicant's prior applications. Further, the removable midsole orthotic of the present invention may be provided as a replacement for worn shoe portions and/or to customize the shoe design for a particular wearer, for a particular activity or both and, as such, may also be combined with one or more of the features or concepts disclosed in my prior applications.

These and other features of the invention will become apparent from the detailed description of the invention which follows.

BRIEF DESCRIPTION OF THE DRAWINGS

FIGS. 1–10 and 12–75 represent embodiments similar to those disclosed in applicant's issued U.S. patents and previous applications. FIG. 11 illustrates aspects of the concavely rounded insertable orthotic midsoles and compartments or bladders with microprocessor controlled variable pressure of the of the present invention.

FIG. 1 is a perspective view of a prior art conventional athletic shoe to which the present invention is applicable.

FIG. 2 illustrates in a close-up frontal plane cross section of the heel at the ankle joint the typical shoe known in the art, which does not deform as a result of body weight, when tilted sideways on the bottom edge.

FIG. 3 shows, in the same close-up cross section as FIG. 2, a naturally rounded shoe sole design, also tilted sideways.

FIG. 4 shows a rear view of a barefoot heel tilted laterally 20 degrees.

FIG. 5 shows, in a frontal plane cross section at the ankle joint area of the heel, tension stabilized sides applied to a naturally rounded shoe sole.

FIG. 6 shows, in a frontal plane cross section, the FIG. 5 design when tilted to its edge, but undeformed by load.

FIG. 7 shows, in frontal plane cross section at the ankle joint area of the heel, the FIG. 5 design when tilted to its edge and naturally deformed by body weight.

FIG. 8 is a sequential series of frontal plane cross sections of the barefoot heel at the ankle joint area.

FIG. 8A is an unloaded and upright barefoot heel.

FIG. 8B is a heel moderately loaded by full body weight and upright.

FIG. 8C is a heavily loaded heel at peak landing force while running and upright.

FIG. 8D is heavily loaded heel shown tilted out laterally by about 20 degrees, the maximum tilt for the heel.

FIG. 9 shows a sequential series of frontal plane cross sections of a shoe sole design of the heel at the ankle joint area that corresponds exactly to the FIG. 8 series described above.

FIG. 10 shows two perspective views and a close-up view of a part of a shoe sole with a structure like the fibrous connective tissue of the groups of fat cells of the human heel.

FIG. 11G is a frontal plane cross-section of an insertable orthotic midsole formed with asymmetric side height. FIGS. 11H–11J show other frontal plane sections. FIG. 11K shows a sagittal plane section and FIG. 11L shows a horizontal plane top view.

FIG. 11M–11O are frontal plane cross-sectional views showing three variations of insertable midsole orthotics with one or more pressure controlled encapsulated insertable midsole orthotics and a control system such as a microprocessor.

FIG. 29 is a frontal plane cross-section showing a shoe sole of uniform thickness that conforms to the natural shape of the human foot.

FIGS. 30A–30D show a load-bearing flat component of a shoe sole and a naturally rounded side component, as well as a preferred horizontal periphery of the flat load-bearing portion of the shoe sole.

FIGS. 31A–31B are diagrammatic sketches showing a rounded side sole design according to the invention with variable heel lift.

FIG. 32 is a side view of a stable rounded shoe according to the invention.

FIG. 33A is a cross-sectional view of the forefoot portion of a shoe sole taken along lines 33A of FIGS. 32 and 33D.

FIG. 33B is a cross-sectional view taken along lines 33B of FIGS. 32 and 33D.

FIG. 33C is a cross-sectional view of the heel portion taken along lines 33C in FIGS. 32 and 33D.

FIG. 33D is a top view of the shoe sole shown in FIG. 32

FIGS. 34A–34D are frontal plane cross-sectional views of a shoe sole according to the invention showing a Theoretically Ideal Stability Plane and truncations of the sole side rounded to reduce shoe bulk.

FIGS. 35A–35C show a rounded sole design according to the invention when applied to various tread and cleat patterns.

FIG. 39 illustrates a fully rounded shoe sole design extended to the bottom of the entire non-load bearing foot.

FIG. 40 shows a fully rounded shoe sole design abbreviated along the sides to only essential structural support and propulsion elements.

FIG. 41 illustrates a street shoe with a correctly rounded sole according to the invention and side edges perpendicular to the ground.

FIG. 49 shows the Theoretically Ideal Stability Plane concept applied to a negative heel shoe sole that is less thick in the heel area than in the rest of the shoe sole.

FIG. 49A is a cross sectional view of the forefoot portion taken along line 49A of FIG. 49D.

FIG. 49B is a view taken along line 49B of FIG. 49D.

FIG. 49C is a view of the heel along line 49C of FIG. 49D.

FIG. 49D is a top view of the shoe sole with a thicker forefoot section shown with cross-hatching.

FIG. 51 shows the use of the Theoretically Ideal Stability Plane concept applied to a flat shoe sole with no heel lift by maintaining the same thickness throughout and providing the shoe sole with rounded stability sides abbreviated to only essential structural support elements.

FIG. 51A is a cross sectional view of the forefoot portion taken along line 51A of FIG. 51D.

FIG. 51B is a view taken along line 51B of FIG. 51D.

FIG. 51C is a view taken along the heel along line 51C in FIG. 51D.

FIG. 51D is a top view of the shoe sole with sides that are abbreviated to essential structural support elements shown hatched.

FIG. 51E is a sagittal plane cross section of the shoe sole of FIG. 51D.

FIG. 53 shows the footprints of the natural barefoot sole and shoe sole.

FIG. 55 shows a shoe sole with a lateral stability sipe in the form of a vertical slit.

FIG. 61 shows a view of a bottom sole structure 149, but with no side sections.

FIG. 64 shows an upper surface between complementary and parallel to the flat ground and a lower surface of the rounded shoe sole side that is not in contact with the ground.

FIGS. 67–68 also shows a shoe sole without rounded stability sides.

FIGS. 69A–E show the implications of relative difference in range of motions between forefoot, midtarsal, and heel areas on the applicant's naturally rounded sides invention.

FIG. 72G shows a shoe sole combining additional stability corrections 96a, 96b, and 98, supporting the first and fifth metatarsal heads and distal phalange heads.

FIG. 72H shows a shoe sole with symmetrical stability additions 96a and 96b.

FIG. 74 shows, in FIGS. 74A–74E, a plurality of side sagittal plane cross-sectional views showing examples of variations in heel lift thickness similar to those shown in FIGS. 50A–E for the forefoot lift.

FIG. 75 shows, in FIGS. 75A–75C, a method for assembling the midsole shoe sole structure of the present invention.

DETAILED DESCRIPTION OF THE PREFERRED EMBODIMENTS

Figure 1:
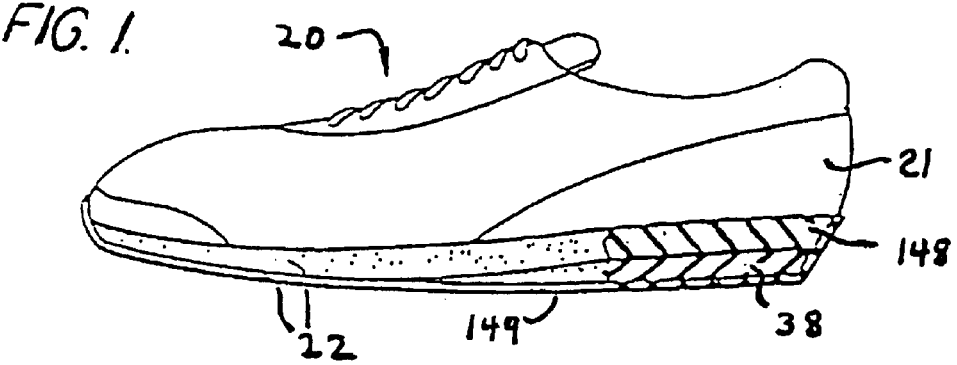

The present invention relates to the provision of an insertable midsole orthotic for a shoe sole which is formed at least in part by midsole material and may be removable from the shoe. The insertable midsole orthotic of the present invention is described more fully with reference to FIGS. 11A–11P below.

The insertable midsole orthotic, can be used in combination with, or to replace, any one or more features of the applicant's prior inventions as shown in the figures of this application. Such use of the insertable midsole orthotic can also include a combination of features shown in any other figures of the present application. For example, the insertable midsole orthotic of the present invention may replace all or any portion or portions of the various midsoles, insoles and bottom soles which are shown in the figures of the present application, and may be combined with or used to implement one or more of the various other features described in reference to any of these figures in any of these forms.

All reference numerals used in the figures contained herein are defined as follows:

| Ref. No. | Element Description |
|---|---|
| 2 | insole |
| 3 | attachment point of upper midsole and shoe upper |
| 4 | attachment point of bottom sole and shoe upper |
| 5 | attachment point of bottom sole and upper midsole |
| 6 | attachment point of bottom sole and lower midsole |
| 8 | lower surface interface with the upper surface of the bottom sole |
| 9 | interface line between encapsulated section and midsole sections |
| 11 | lateral stability sipe |
| 12 | medial stability sipe |
| 13 | interface between insole and shoe upper |
| 14 | medial origin of the lateral stability sipe |
| 16 | hatched area of decreased area of footprint due to pronation |
| 17 | footprint outline when tilted |
| 18 | inner footprint outline of low arched foot |
| 19 | hatched area of increased area of footprint due to pronation |
| 20 | athletic shoe |
| 21 | shoe upper |
| 21a | inner secondary shoe upper |
| 22 | conventional shoe sole |
| 23 | bottom outside edge of the shoe sole |
| 23a | lever arm |
| 26 | stabilizing quadrants |
| 27 | human foot |
| 28 | rounded shoe sole |
| 28a | rounded stability sides |
| 28b | load bearing shoe sole |
| 29 | outer surface of the foot |
| 30 | upper surface of the shoe sole |
| 30a | side or inner edge of the shoe sole stability side |
| 30b | upper shoe sole surface which contacts the wearer's foot |
| 31 | lower surface of the shoe sole |
| 31a | outer edge of rounded stability sides |
| 31b | lower surface of shoe sole parallel to 30b |
| 32 | outside and top edge of the stability side |
| 33 | inner edge of the naturally rounded stability side |
| 34 | perpendicular sides of the load-bearing shoe sole |
| 35 | peripheral extent of the upper surface of sole |
| 36 | shoe sole outline |
| 37 | foot outline |
| 37a | maximum supination position |
| 37b | maximum pronation position |
| 38 | heel lift |
| 39 | combined midsole and bottom sole |
| 40 | forefoot lift |
| 43 | ground |
| 51 | Theoretically Ideal Stability Plane |
| 51' | half of the Theoretically Ideal Stability Plane |
| 53a | top of rounded stability side |
| 60 | tread portion |
| 61 | cleated portion |
| 62 | alternative tread construction |
| 63 | surface which the cleat bases are affixed |
| 70 | curve of range of side to side motion |
| 71 | center of gravity |
| 80 | conventional wide heel flare curve |
| 82 | narrow rectangle the width of heel curve |
| 85 | rounded line of areas of shoe sole that are in contact with the ground |
| 86 | rounded line |
| 86 | rounded line |
| 87 | rounded line |
| 88 | rounded line |
| 89 | rounded line |
| 92 | head of first metatarsal |
| 93 | head of fifth distal phalange |
| 94 | head of fifth metatarsal |
| 95 | base and lateral tuberosity of the calcaneus |
| 96 | heads of the metatarsals |
| 96a | stability correction supporting fifth metatarsal and distal phalange heads |
| 96b | stability correction supporting first metatarsal and distal phalange heads |
| 97 | base of the fifth metatarsal |
| 98 | head of the first distal phalange |
| 98a | stability correction supporting first distal phalange |
| 98a' | stability correction supporting fifth distal phalange |
| 100 | straight line replacing indentation at the base of the fifth metatarsal |
| 104 | pressure sensing device |
| 108 | lateral calcaneal tuberosity |
| 109 | main base of the calcaneus |
| 111 | flexibility axis |
| 112 | flexibility axis |
| 113 | flexibility axis |
| 115 | center of rotation of radius r + r' |
| 119 | center of shoe sole support section |
| 120 | pressure sensing circuitry |
| 121 | main longitudinal arch (long arch) |
| 122 | flexibility axis |
| 123 | flexible connecting top layer of sipes |
| 124 | flexibility axis |
| 125 | base of the calcaneus (heel) |
| 126 | metatarsal heads (forefoot) |
| 129 | honeycombed portion |
| 145 | insertable midsole orthotic |
| 147 | upper midsole (upper areas of shoe midsole) |
| 148 | midsole |
| 149 | bottom or outer sole |
| 149a | secondary bottom sole |
| 150 | compression force |
| 151 | channels with parallel side walls |
| 155a | tension force along the top surface of the shoe sole |
| 155b | mirror image of tension force 155a |
| 158 | subcalcaneal fat pad |
| 159 | calcaneus |
| 160 | bottom sole of the foot |
| 161 | cushioning compartment |
| 162 | natural crease or upward taper |
| 163 | crease or taper in the human foot |
| 164 | chambers of matrix of elastic fibrous connective tissue |
| 165 | lower surface of the upper midsole |
| 166 | upper surface of the bottom sole |
| 167 | outer surface of the support structures of the foot |
| 168 | upper surface of the foot's bottom sole |
| 169 | shank |
| 170 | flexible material filling channels (sipes) |
| 176 | protrusions |
| 177 | recesses |
| 180 | mini-chambers |
| 181 | internal deformation slits (sipes) in the sagittal plane |
| 182 | internal deformation slits (sipes) in the horizontal plane |
| 184 | encapsulating outer midsole section |
| 185 | midsole sides |
| 187 | upper midsole section |
| 188 | bladder or encapsulated midsole section |
| 189 | central wall |
| 191 | fibrous capsule shell |
| 192 | subdivided cushioning compartments |
| 201 | horizontal line through lower most point of upper surface of the shoe sole |
| 206 | fluid duct |
| 210 | fluid valve |
| 300 | encapsulated midsole section control system |
| 301 | mechanical fasteners |
| 302 | adhesive |
| 303 | snap fit |

FIG. 1 shows a perspective view of a shoe, such as a typical athletic shoe according to the prior art, wherein the athletic shoe 20 includes an upper portion 21 and a sole 22.

Figure 2:
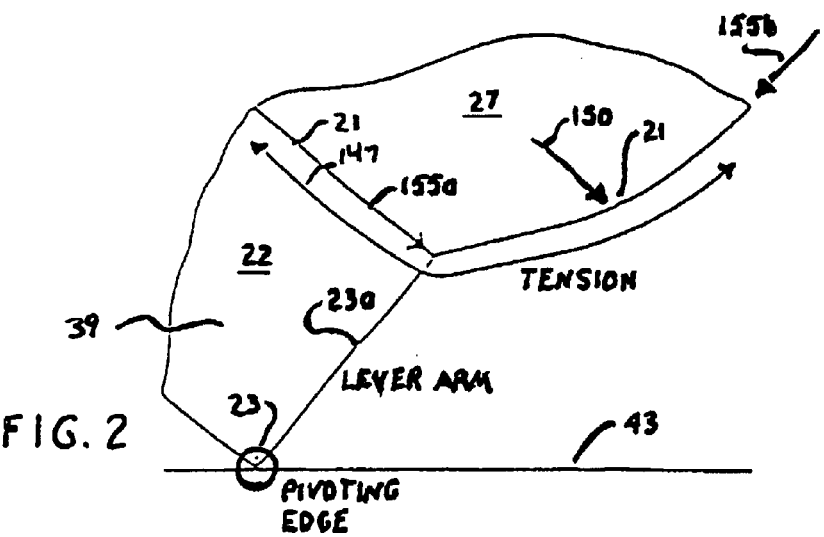

FIG. 2 illustrates, in a close-up, a cross-section of a typical shoe of existing art (underformed by body weight) on the ground 43 when tilted on the bottom outside edge 23 of the shoe sole 22, that an inherent stability problem remains in existing shoe designs, even when the abnormal torque producing rigid heel counter and other motion devices are removed. The problem is that the remaining shoe upper 21

(shown in the thickened and darkened line), while providing no lever arm extension, since it is flexible instead of rigid, nonetheless creates unnatural destabilizing torque on the shoe sole. The torque is due to the tension force 155a along the top surface of the shoe sole 22 caused by a compression force 150 (a composite of the force of gravity on the body and a sideways motion force) to the side by the foot 27, due simply to the shoe being tilted to the side, for example. The resulting destabilizing force acts to pull the shoe sole in rotation around a lever arm 23a that is the width of the shoe sole at the edge. Roughly speaking, the force of the foot on the shoe upper pulls the shoe over on its side when the shoe is tilted sideways. The compression force 150 also creates a tension force 155b, which is the mirror image of tension force 155a.

Figure 3:
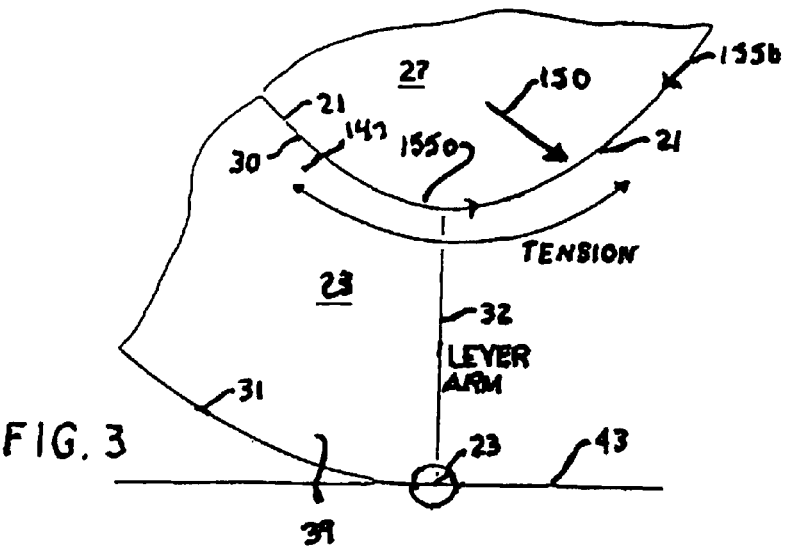

FIG. 3 shows, in a close-up cross section of a naturally rounded design shoe sole 28 (also shown undeformed by body weight) when tilted on the bottom edge, that the same inherent stability problem remains in the naturally rounded shoe sole design, though to a reduced degree. The problem is less since the direction of the force vector 150 along the lower surface of the shoe upper 21 is parallel to the ground 43 at the outer sole edge 32 edge, instead of angled toward the ground as in a conventional design like that shown in FIG. 2, so the resulting torque produced by a lever arm created by the outer sole edge 32 would be less, and the rounded shoe sole 28 provides direct structural support when tilted, unlike conventional designs.

Figure 4:
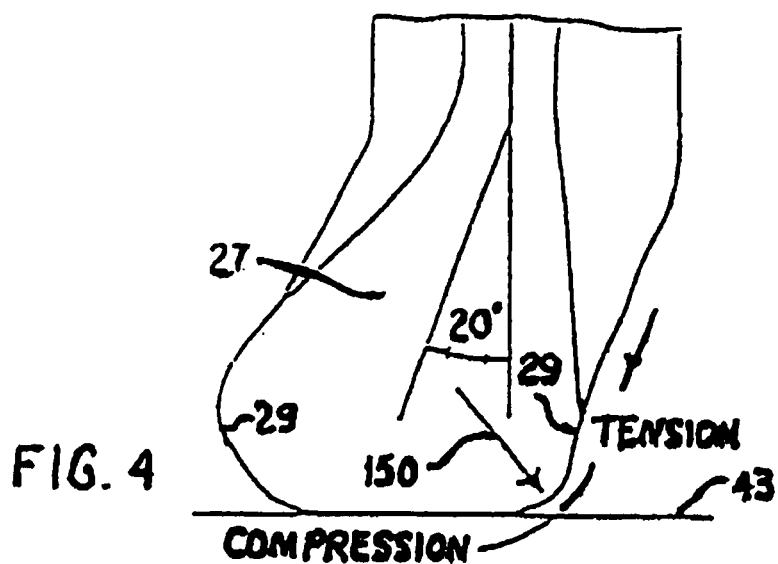

FIG. 4 shows (in a rear view) that, in contrast, the bare foot is naturally stable because, when deformed by body weight and tilted to its natural lateral limit of about 20 degrees, it does not create any destabilizing torque due to tension force. Even though tension paralleling that on the shoe upper is created on the outer surface 29, both the bottom and sides, of the bare foot by the compression force of weight-bearing, no destabilizing torque is created because the lower surface under tension (i.e. the foot's bottom sole, shown in the darkened line) is resting directly in contact with the ground. Consequently, there is no unnatural lever arm artificially created against which to pull. The weight of the body firmly anchors the outer surface of the sole underneath the foot so that even considerable pressure against the outer surface 29 of the side of the foot results in no destabilizing motion. When the foot is tilted, the supporting structures of the foot, like the calcaneus, slide against the side of the strong but flexible outer surface of the foot and create very substantial pressure on that outer surface at the sides of the foot. But that pressure is precisely resisted and balanced by tension along the outer surface of the foot, resulting in a stable equilibrium.

Figure 5A:
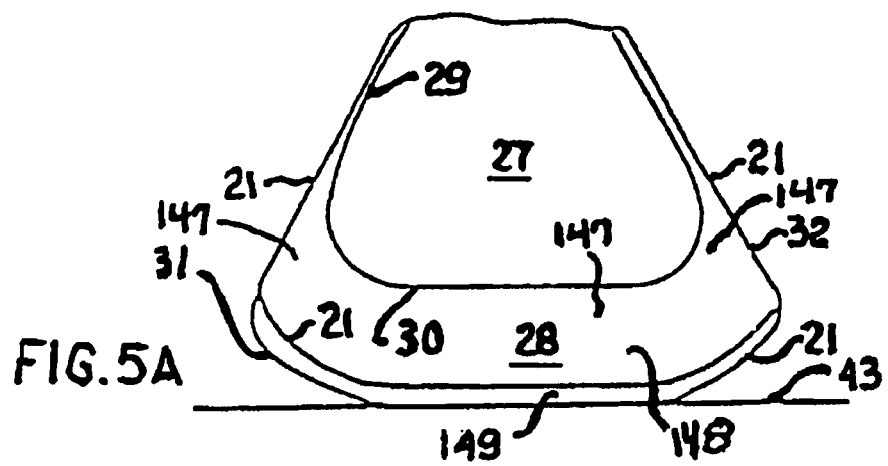
Figure 5B:
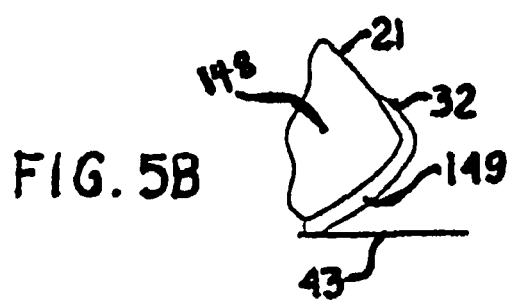

FIG. 5 shows, in cross section of the upright heel deformed by body weight, the principle of the tension-stabilized sides of the bare foot applied to the naturally rounded shoe sole design. The same principle can be applied to conventional shoes, but is not shown. The key change from the existing art of shoes is that the sides of the shoe upper 21 (shown as darkened lines) must wrap around the outside edges 32 of the rounded shoe sole 28, instead of attaching underneath the foot to the upper surface 30 of the shoe sole, as is done conventionally. The shoe upper sides can overlap and be attached to either the inner (shown on the left) or outer surface (shown on the right) of the bottom sole, since those sides are not unusually load-bearing, as shown. Alternatively, the bottom sole, optimally thin and tapering as shown, can extend upward around the outside edges 32 of the shoe sole to overlap and attach to the shoe upper sides (shown FIG. 5B). Their optimal position coincides with the Theoretically Ideal Stability Plane, so that the tension force on the shoe sides is transmitted directly all the way down to the bottom surface of the shoe, which anchors it on the ground with virtually no intervening artificial lever arm. For shoes with only one sole layer, the attachment of the shoe upper sides should be at or near the lower or bottom surface of the shoe sole.

The design shown in FIG. 5 is based on a fundamentally different conception: that the shoe upper is integrated into the shoe sole, instead of attached on top of it, and the shoe sole is treated as a natural extension of the foot sole, not attached to it separately.

The fabric (or other flexible material, like leather) of the shoe uppers would preferably be non-stretch or relatively so, so as not to be deformed excessively by the tension placed upon its sides when compressed as the foot and shoe tilt. The fabric can be reinforced in areas of particularly high tension, like the essential structural support and propulsion elements defined in the applicant's earlier applications (the base and lateral tuberosity of the calcaneus, the base of the fifth metatarsal, the heads of the metatarsals, and the first distal phalange). The reinforcement can take many forms, such as like that of corners of the jib sail of a racing sailboat or more simple straps. As closely as possible, it should have the same performance characteristics as the heavily callused skin of the sole of an habitually bare foot. Preferably, the relative density of the shoe sole is as described in FIG. 46 of the present application with the softest sole density nearest the foot sole, a progression through less soft sole density through the sole, to the firmest and least flexible at the outermost shoe sole layer. This arrangement allows the conforming sides of the shoe sole to avoid providing a rigid destabilizing lever arm.

The change from existing art to provide the tension-stabilized sides shown in FIG. 5 is that the shoe upper is directly integrated functionally with the shoe sole, instead of simply being attached on top of it. The advantage of the tension-stabilized sides design is that it provides natural stability as close to that of the bare foot as possible, and does so economically, with the minimum shoe sole side width possible.

Figure 6:
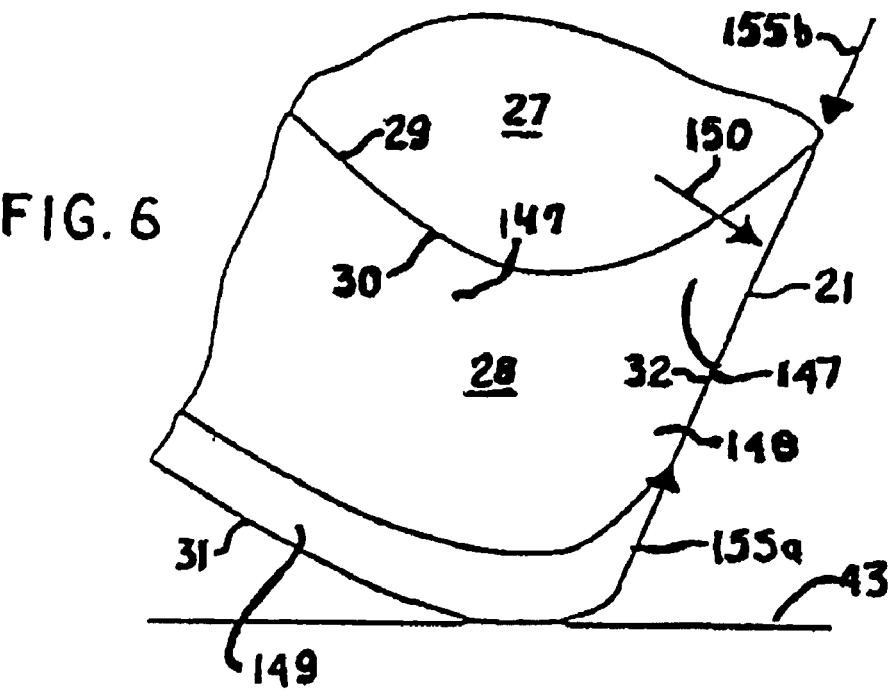

The result is a shoe sole that is naturally stabilized in the same way that the barefoot is stabilized, as seen in FIG. 6, which shows a close-up cross section of a naturally rounded shoe sole 28 (undeformed by body weight) when tilted to the edge. The same destabilizing force against the side of the shoe shown in FIG. 2 is now stably resisted by offsetting tension in the surface of the shoe upper 21 extended down the side of the shoe sole so that it is anchored by the weight of the body when the shoe and foot are tilted.

In order to avoid creating unnatural torque on the shoe sole, the shoe uppers may be joined or bonded only to the bottom sole, not the midsole, so that pressure shown on the side of the shoe upper produces side tension only and not the destabilizing torque from pulling similar to that described in FIG. 2. However, to avoid unnatural torque, the upper areas 147 of the shoe midsole, which form a sharp corner, should be composed of relatively soft midsole material. In this case, bonding the shoe uppers to the midsole would not create very much destabilizing torque. The bottom sole 149 is preferably thin, at least on the stability sides, so that its attachment overlap with the shoe upper sides coincides, as closely as possible, to the Theoretically Ideal Stability Plane, so that force is transmitted by the outer shoe sole surface to the ground.

In summary, the FIG. 5 design is for a shoe construction, including: a shoe upper that is composed of material that is flexible and relatively inelastic at least where the shoe upper contacts the areas of the structural bone elements of the human foot, and a shoe sole that has relatively flexible sides; and at least a portion of the sides of the shoe upper are attached directly to the bottom sole, while enveloping on the outside the other sole portions of the shoe sole. This construction can either be applied to conventional shoe sole structures or to the applicant's prior shoe sole inventions, such as the naturally rounded shoe sole conforming to the Theoretically Ideal Stability Plane.

Figure 7:
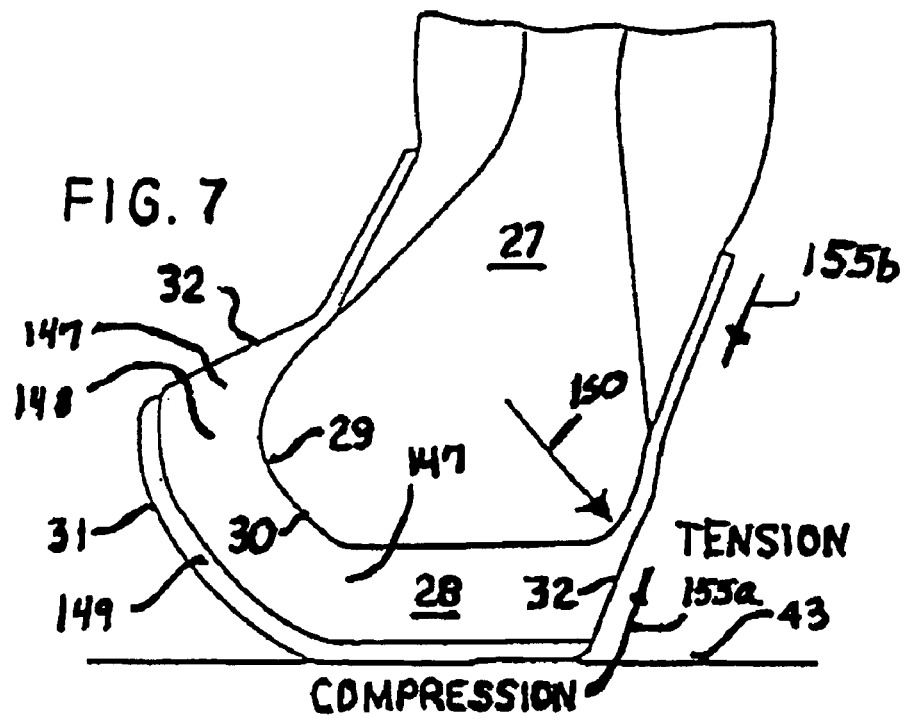

FIG. 7 shows, in cross-section at the heel, the tension-stabilized sides concept applied to naturally rounded shoe sole 28 when the shoe and foot are tilted out fully and are naturally deformed by body weight (although constant shoe sole thickness is shown undeformed). The figure shows that the shape and stability function of the shoe sole and shoe uppers mirror almost exactly that of the human foot.

FIGS. 8A–8D show the natural cushioning of the human bare foot 27, in cross sections at the heel. FIG. 8A shows the bare heel upright and unloaded, with little pressure on the subcalcaneal fat pad 158, which is evenly distributed between the calcaneus 159, which is the heel bone, and the bottom sole 160 of the foot.

FIG. 8B shows the bare heel upright but under the moderate pressure of full body weight. The compression of the calcaneus against the subcalcaneal fat pad produces evenly balanced pressure within the subcalcaneal fat pad because it is contained and surrounded by a relatively unstretchable fibrous capsule, the bottom sole of the foot. Underneath the foot, where the bottom sole is in direct contact with the ground, the pressure caused by the calcaneus on the compressed subcalcaneal fat pad is transmitted directly to the ground. Simultaneously, substantial tension is created on the sides of the bottom sole of the foot because of the surrounding relatively tough fibrous capsule. That combination of bottom pressure and side tension is the foot's natural shock absorption system for support structures like the calcaneus and the other bones of the foot that come in contact with the ground.

Of equal functional importance is that lower surface 167 of those support structures of the foot like the calcaneus and other bones make firm contact with the upper surface 168 of the foot's bottom sole underneath, with relatively little uncompressed fat pad intervening. In effect, the support structures of the foot land on the ground and are firmly supported; they are not suspended on top of springy material in a buoyant manner analogous to a water bed or pneumatic tire, as in some existing proprietary shoe sole cushioning systems. This simultaneously firm and yet cushioned support provided by the foot sole must have a significantly beneficial impact on energy efficiency, also called energy return, different from some conventional shoe sole designs which provide shock absorption cushioning during the landing and support phases of locomotion at the expense of firm support during the take-off phase.

The incredible and unique feature of the foot's natural system is that, once the calcaneus is in fairly direct contact with the bottom sole and therefore providing firm support and stability, increased pressure produces a more rigid fibrous capsule that protects the calcaneus and produces greater tension at the sides to absorb shock. So, in a sense, even when the foot's suspension system would seem in a conventional way to have bottomed out under normal body weight pressure, it continues to react with a mechanism to protect and cushion the foot even under very much more extreme pressure. This is seen in FIG. 8C, which shows the human heel under the heavy pressure of roughly three times body weight force of landing during routine running. This can be easily verified: when one stands barefoot on a hard floor, the heel feels very firmly supported and yet can be lifted and virtually slammed onto the floor with little increase in the feeling of firmness; the heel simply becomes harder as the pressure increases.

In addition, it should be noted that this system allows the relatively narrow base of the calcaneus to pivot from side to side freely in normal pronation/supination motion, without any obstructing torsion on it, despite the very much greater width of compressed foot sole providing protection and cushioning. This is crucially important in maintaining natural alignment of joints above the ankle joint such as the knee, hip and back, particularly in the horizontal plane, so that the entire body is properly adjusted to absorb shock correctly. In contrast, existing shoe sole designs, which are generally relatively wide to provide stability, produce unnatural frontal plane torsion on the calcaneus, restricting its natural motion, and causing misalignment of the joints operating above it, resulting in the overuse injuries unusually common with such shoes. Instead of flexible sides that harden under tension caused by pressure like that of the foot, some existing shoe sole designs are forced by lack of other alternatives to use relatively rigid sides in an attempt to provide sufficient stability to offset the otherwise uncontrollable buoyancy and lack of firm support of air or gel cushions.

FIG. 8D shows the bare foot deformed under full body weight and tilted laterally to roughly the 20 degree limit of normal movement range. Again it is clear that the natural system provides both firm lateral support and stability by providing relatively direct contact with the ground, while at the same time providing a cushioning mechanism through side tension and subcalcaneal fat pad pressure.

FIGS. 9A–9D show, also in cross-sections at the heel, a naturally rounded shoe sole design that parallels as closely as possible the overall natural cushioning and stability system of the barefoot described in FIG. 8, including a cushioning compartment 161 under support structures of the foot containing a pressure-transmitting medium like gas, gel, or liquid, like the subcalcaneal fat pad under the calcaneus and other bones of the foot. Consequently, FIGS. 9A–D directly correspond to FIGS. 8A–D. The optimal pressure-transmitting medium is that which most closely approximates the fat pads of the foot. Silicone gel is probably most optimal of materials currently readily available, but future improvements are probable. Since it transmits pressure indirectly, in that it compresses in volume under pressure, gas is significantly less optimal. The gas, gel, or liquid, or any other effective material, can be further encapsulated itself, in addition to the sides of the shoe sole, to control leakage and maintain uniformity, as is common conventionally, and can be subdivided into any practical number of encapsulated areas within a compartment, again as is common conventionally. The relative thickness of the cushioning compartment 161 can vary, as can the bottom sole 149 and the upper midsole 147, and can be consistent or differ in various areas of the shoe sole. The optimal relative sizes should be those that approximate most closely those of the average human foot, which suggests both smaller upper and lower soles and a larger cushioning compartment than shown in FIG. 9. The cushioning compartments or pads 161 can be placed anywhere from directly underneath the foot, like an insole, to directly above the bottom sole. Optimally, the amount of compression created by a given load in any cushioning compartment 161 should be tuned to approximate as closely as possible the compression under the corresponding fat pad of the foot.

The function of the subcalcaneal fat pad is not met satisfactorily with existing proprietary cushioning systems, even those featuring gas, gel or liquid as a pressure transmitting medium. In contrast to those artificial systems, the design shown in FIG. 9 conforms to the natural rounded of the foot and to the natural method of transmitting bottom pressure into side tension in the flexible but relatively non-stretching (the actual optimal elasticity will require empirical studies) sides of the shoe sole.

Figure 9A:
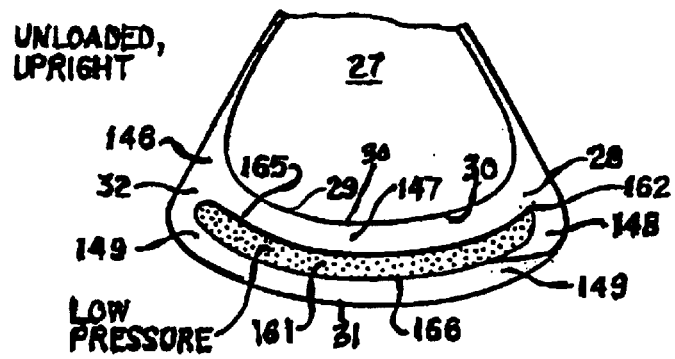
Figure 9B:
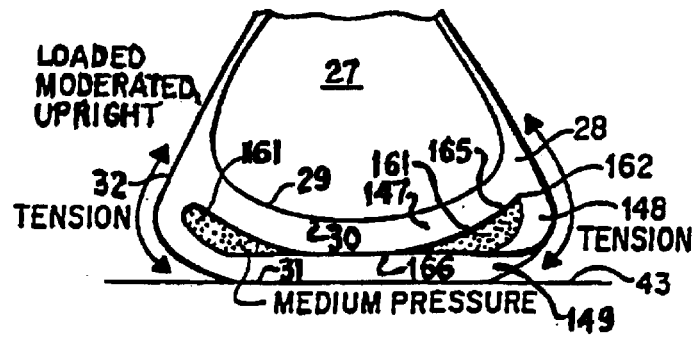
Figure 9C:
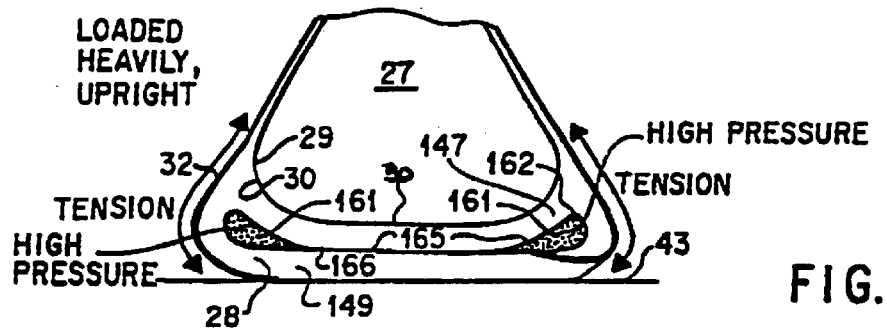

Some existing cushioning systems do not bottom out under moderate loads and rarely if ever do so under extreme loads. Rather, the upper surface of the cushioning device remains suspended above the lower surface. In contrast, the design in FIG. 9 provides firm support to foot support structures by providing for actual contact between the lower surface 165 of the upper midsole 147 and the upper surface 166 of the bottom sole 149 when fully loaded under moderate body weight pressure, as indicated in FIG. 9B, or under maximum normal peak landing force during running, as indicated in FIG. 9C, just as the human foot does in FIGS. 8B and 8C. The greater the downward force transmitted through the foot to the shoe, the greater the compression pressure in the cushioning compartment 161 and the greater the resulting tension on the shoe sole sides.

Figure 9D:
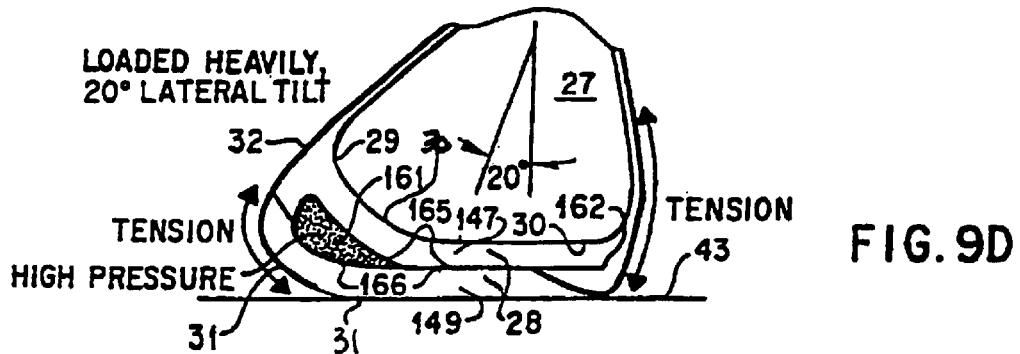

FIG. 9D shows the same shoe sole design when fully loaded and tilted to the natural 20 degree lateral limit, like FIG. 8D. FIG. 9D shows that an added stability benefit of the natural cushioning system for shoe soles is that the effective thickness of the shoe sole is reduced by compression on the side so that the potential destabilizing lever arm represented by the shoe sole thickness is also reduced, and thus foot and ankle stability is increased. Another benefit of the FIG. 9 design is that the upper midsole shoe surface can move in any horizontal direction, either sideways or front to back in order to absorb shearing forces. The shearing motion is controlled by tension in the sides. Note that the right side of FIGS. 9A–D is modified to provide a natural crease or upward taper 162, which allows complete side compression without binding or bunching between the upper and lower shoe sole layers 147, 148, and 149 . The shoe sole crease 162 parallels exactly a similar crease or taper 163 in the human foot. Further, 201 represents a horizontal line through the lower most point of the upper surface 30 of the shoe sole.

Another possible variation of joining shoe upper to shoe bottom sole is on the right (lateral) side of FIGS. 9A–D, which makes use of the fact that it is optimal for the tension absorbing shoe sole sides, whether shoe upper or bottom sole, to coincide with the Theoretically Ideal Stability Plane along the side of the shoe sole beyond that point reached when the shoe is tilted to the foot's natural limit, so that no destabilizing shoe sole lever arm is created when the shoe is tilted fully, as in FIG. 9D. The joint may be moved up slightly so that the fabric side does not come in contact with the ground, or it may be covered with a coating to provide both traction and fabric protection.

It should be noted that the FIG. 9 design provides a structural basis for the shoe sole to conform very easily to the natural shape of the human foot and to parallel easily the natural deformation flattening of the foot during load-bearing motion on the ground. This is true even if the shoe sole is made conventionally with a flat sole, as long as rigid structures such as heel counters and motion control devices are not used; though not optimal, such a conventional flat shoe made like FIG. 9 would provide the essential features of the invention resulting in significantly improved cushioning and stability. The FIG. 9 design could also be applied to intermediate-shaped shoe soles that neither conform to the flat ground or the naturally rounded foot. In addition, the FIG. 9 design can be applied to the applicant's other designs, such as those described in FIGS. 14–28 of the present application.

In summary, the FIG. 9 design shows a shoe construction for a shoe, including: a shoe sole with a compartment or compartments under the structural elements of the human foot, including at least the heel; the compartment or compartments contain a pressure-transmitting medium like liquid, gas, or gel; a portion of the upper surface of the shoe sole compartment firmly contacts the lower surface of said compartment during normal load-bearing; and pressure from the load-bearing is transmitted progressively at least in part to the relatively inelastic sides, top and bottom of the shoe sole compartment or compartments, producing tension.

Figure 10A:
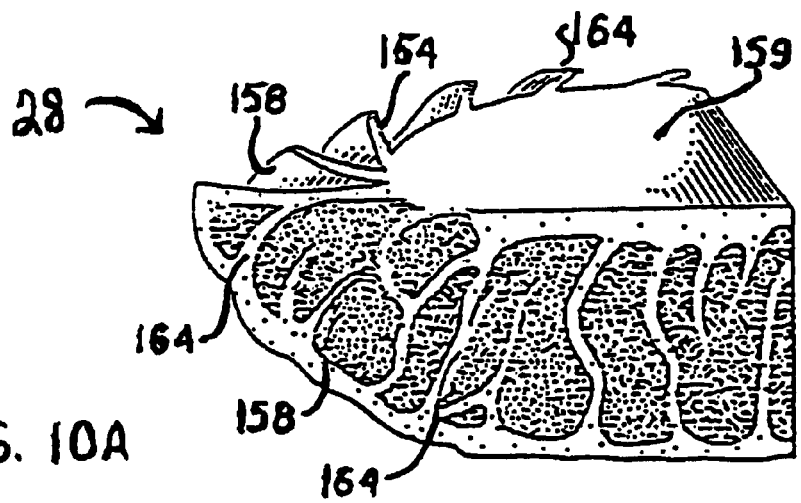
FIG. 10A shows a quartered section of a shoe sole with a structure comprising elements corresponding to the calcaneus with fat pad chambers below it.
Figure 10B:
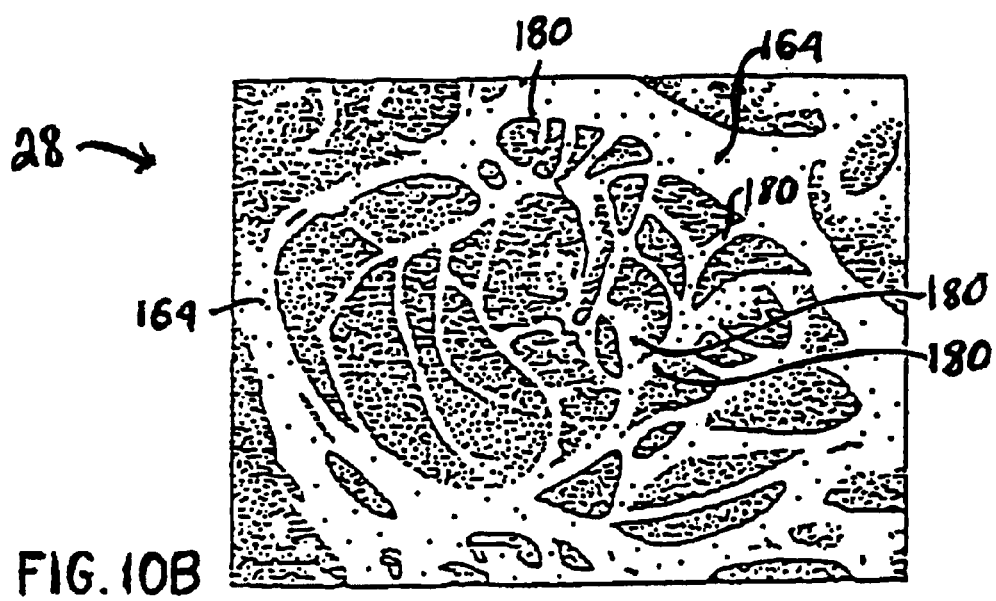
FIG. 10B shows a horizontal plane close-up of the inner structures of an individual chamber of a shoe sole.
Figure 10C:
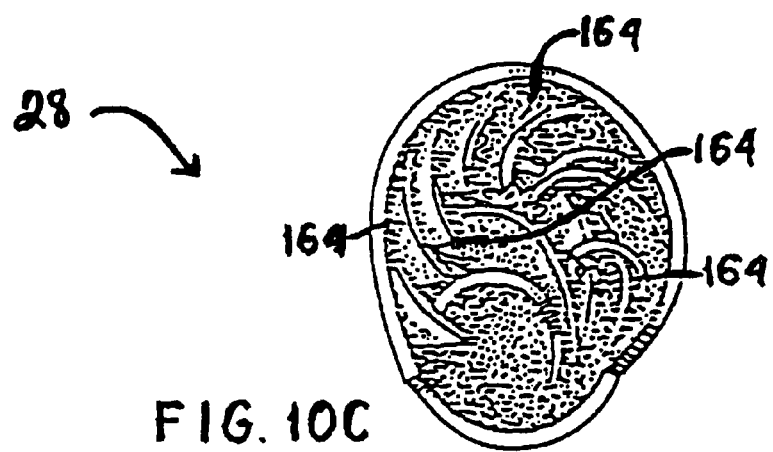
FIG. 10C shows a horizontal section of a shoe sole with a structure corresponding to the whorl arrangement of fat pad underneath the calcaneus.

While the FIG. 9 design copies in a simplified way the macro structure of the foot, FIGS. 10 A–C focus more on the exact detail of shoe soles modeled after the natural structures of the foot, including at the micro level. FIGS. 10A and 10C are perspective views of cross sections of a part of a rounded shoe sole 28 with a structure like the human heel, wherein elements of the shoe sole structure are similar to chambers of a matrix of elastic fibrous connective tissue which hold closely packed fat cells in the foot 164. The chambers in the foot are structured as whorls radiating out from the calcaneus. These fibrous-tissue strands are firmly attached to the under surface of the calcaneus and extend to the subcutaneous tissues. They are usually in the form of the letter U, with the open end of the U pointing toward the calcaneus.

As the most natural, an approximation of this specific chamber structure would appear to be the most optimal as an accurate model for the structure of the shoe sole cushioning compartments 161. The description of the structure of calcaneal padding provided by Erich Blechschmidt in Foot and Ankle, March, 1982, (translated from the original 1933 article in German) is so detailed and comprehensive that copying the same structure as a model in shoe sole design is not difficult technically, once the crucial connection is made that such copying of this natural system is necessary to overcome inherent weaknesses in the design of existing shoes. Other arrangements and orientations of the whorls are possible, but would probably be less optimal.

Pursuing this nearly exact design analogy, the lower surface 165 of the upper midsole 147 would correspond to the outer surface 167 of the calcaneus 159 and would be the origin of the U shaped whorl chambers 164 noted above.

FIG. 10B shows a close-up of the interior structure of the large chambers of a rounded shoe sole 28 as shown in FIGS. 10A and 10C, with mini-chambers 180 similar to mini-chambers in the foot. It is clear from the fine interior structure and compression characteristics of the mini-chambers 180 in the foot that those directly under the calcaneus become very hard quite easily, due to the high local pressure on them and the limited degree of their elasticity, so they are able to provide very firm support to the calcaneus or other bones of the foot sole. By virtue of their being fairly inelastic, the compression forces on those compartments are dissipated to other areas of the network of fat pads under any given support structure of the foot, like the calcaneus. Consequently, if a cushioning compartment 161, such as the compartment under the heel shown in FIG. 9, is subdivided into smaller chambers, like those shown in FIG. 10, then actual contact between the lower surface of the upper midsole 165 and the upper surface of the bottom sole 166 would no longer be required to provide firm support, so long as those compartments and the pressure-transmitting medium contained in them have material characteristics similar to those of the foot, as described above. The use of gas may not be satisfactory in this approach, since its compressibility may not allow adequate firmness.

In summary, the FIG. 10 design shows a shoe construction including: a shoe sole with a compartments under the structural elements of the human foot, including at least the heel; the compartments containing a pressure-transmitting medium like liquid, gas, or gel; the compartments having a whorled structure like that of the fat pads of the human foot sole; load-bearing pressure being transmitted progressively at least in part to the relatively inelastic sides, top and bottom of the shoe sole compartments, producing tension therein; the elasticity of the material of the compartments and the pressure-transmitting medium are such that normal weight-bearing loads produce sufficient tension within the structure of the compartments to provide adequate structural rigidity to allow firm natural support to the foot structural elements, like that provided by the fat pads of the bare foot. That shoe sole construction can have shoe sole compartments that are subdivided into mini-chambers like those of the fat pads of the foot sole.

Since the bare foot that is never shod is protected by very hard calluses (called a "Seri boot") which the shod foot lacks, it seems reasonable to infer that natural protection and shock absorption system of the shod foot is adversely affected by its unnaturally undeveloped fibrous capsules (surrounding the subcalcaneal and other fat pads under foot bone support structures). A solution would be to produce a shoe intended for use without socks (i.e. with smooth surfaces above the foot bottom sole) that uses insoles that coincide with the foot bottom sole, including its sides. The upper surface of those insoles, which would be in contact with the bottom sole of the foot (and its sides), would be coarse enough to stimulate the production of natural barefoot calluses. The insoles would be removable and available in different uniform grades of coarseness, as is sandpaper, so that the user can progress from finer grades to coarser grades as his foot soles toughen with use.

Similarly, socks could be produced to serve the same function, with the area of the sock that corresponds to the foot bottom sole (and sides of the bottom sole) made of a material coarse enough to stimulate the production of calluses on the bottom sole of the foot, with different grades of coarseness available, from fine to coarse, corresponding to feet from soft to naturally tough. Using a tube sock design with uniform coarseness, rather than conventional sock design assumed above, would allow the user to rotate the sock on his foot to eliminate any "hot spot" irritation points that might develop. Also, since the toes are most prone to blistering and the heel is most important in shock absorption, the toe area of the sock could be relatively less abrasive than the heel area.

Orthotics are well known in the art and are exemplified by U.S. Pat. No. 4,803,747 issued to Brown and U.S. Pat. No. 4,868,945 issued to DeBettignies.

Figure 11A:
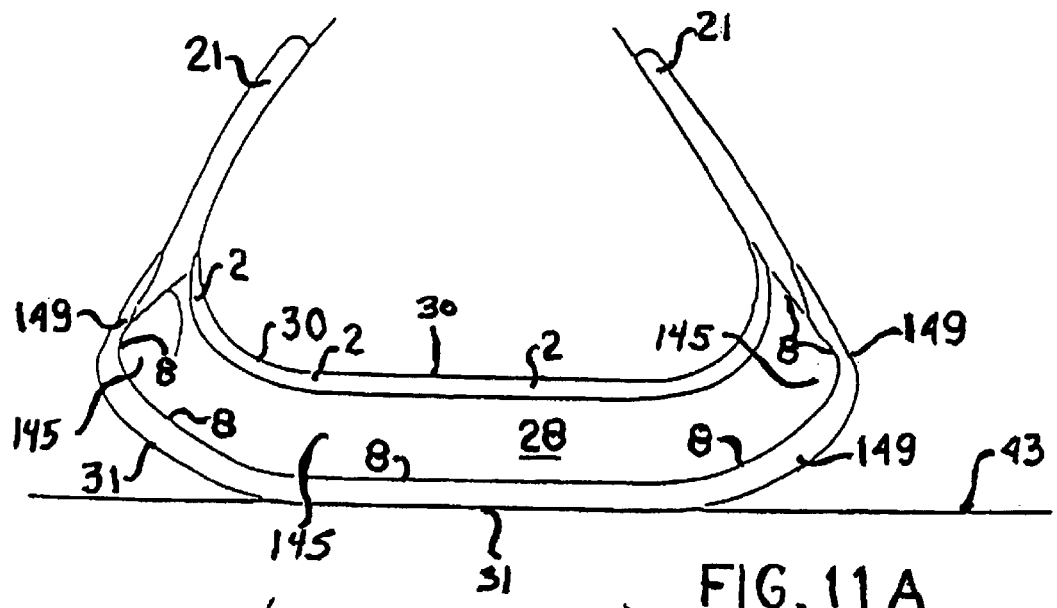
FIGS. 11A–11C are frontal plane cross-sectional views showing three different variations of insertable orthotic midsoles in accordance with the present invention.
Figure 11Q:
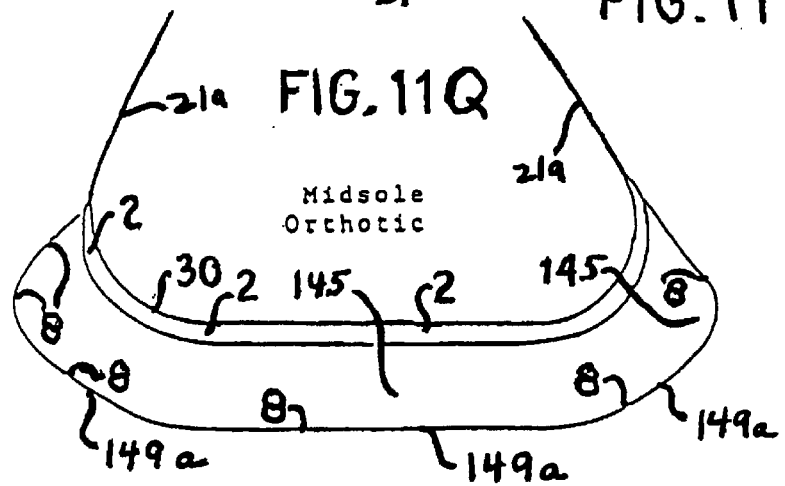
FIGS. 11Q–11R are frontal plane cross-sectional views showing two variations of orthotic inner shoes in accordance with the present invention.
Figure 11R:
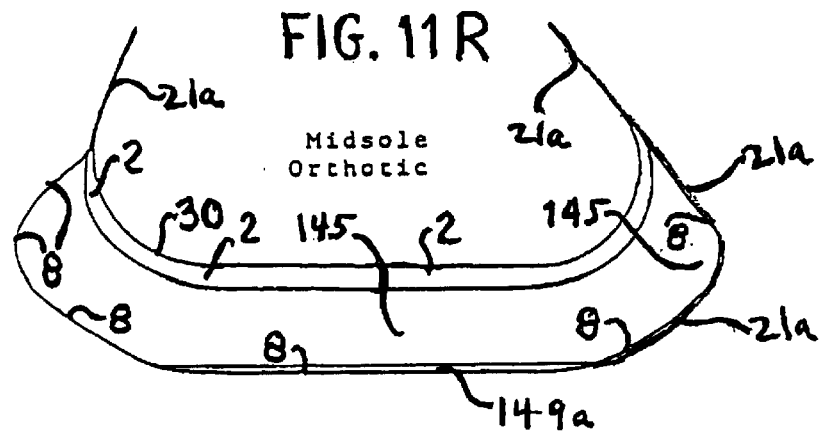
Figure 11B:
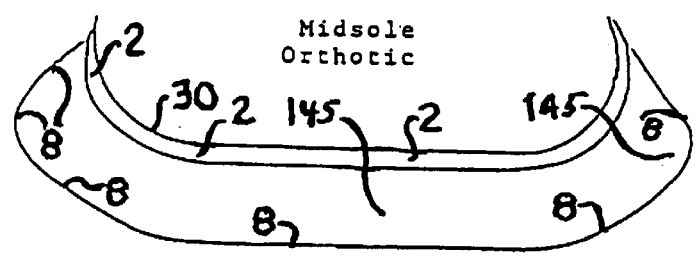
Figure 11C:
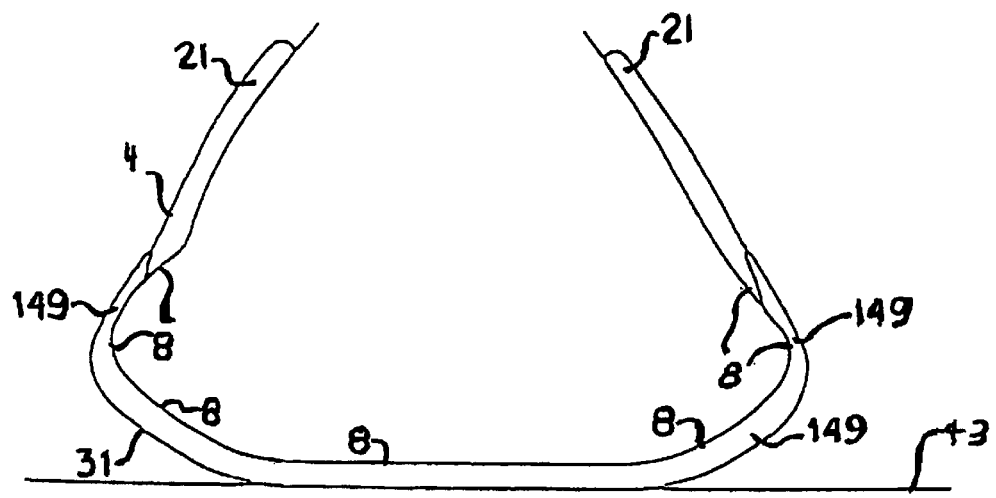

The invention shown in FIGS. 11A–11C includes a removable, and reinsertable, insertable midsole orthotic 145 which is formed at least in part by midsole material. Alternatively, the insertable midsole orthotic 145 can be attached permanently to adjoining portions of the rounded shoe sole 28 after initial insertion using glue or other common forms or attachment. The rounded shoe sole 28 has an upper surface 30 and a lower surface 31 with at least a part of both surfaces being concavely rounded, as viewed in a frontal plane from inside the shoe when in an unloaded and upright condition. Preferably, all or a part of the insertable midsole orthotic 145 can be removable through any practical number of insertion/removal cycles. The insertable midsole orthotic 145 can also, optionally, include a concavely rounded side, as shown in FIG. 11A, or a concavely rounded underneath portion or be conventionally formed, with other portions of the shoe sole including concave rounding on the side or underneath portion or portions. All or part of the preferred insole 2 can also be removable or can be integrated into the upper portion of the insertable midsole orthotic 145.

The removable portion or portions of the insertable midsole orthotic 145 can include all or part of the heel lift (not shown) of the rounded shoe sole 28, or all or part of the heel lift 38 can be incorporated into the bottom sole 149 permanently, either using bottom sole material, midsole material, or other suitable material. Heel lift 38 is typically formed from cushioning material such as the midsole materials described herein or may be integrated with the upper midsole 147 or midsole 148 or any portion thereof, including the insertable midsole orthotic 145.

The removable portion of the insertable midsole orthotic 145 can extend the entire length of the shoe sole, as shown in FIGS. 11K and 11L, or only a part of the length, such as a heel area as shown in cross section in FIG. 11G, a midtarsal area as shown in cross section in FIG. 11H, a forefoot area as shown in cross section FIGS. 11I and 11J, or some portion or combination of those areas. The removable portion and/or insertable midsole orthotic 145 may be fabricated in any suitable, conventional manner employed for the fabrication of midsoles or other, similar structures.

The insertable midsole orthotic 145, as well as other midsole sections of the shoe sole such as the midsole 148 and the upper midsole 147, can be fabricated from any suitable material such as elastomeric foam materials. Examples of current art for elastomeric foam materials include polyether urethane, polyester urethane foams, ethylene vinyl acetate, ethylene vinyl acetate/polyethylene copolymers, polyester elastomers such as Hytrel® fluoroelastomers, chlorinated polyethylene, chlorosulfonated polyethylene, acrylonitrile rubber, ethylene vinyl acetate/polypropylene copolymers, polyethylene, polypropylene, neoprene, natural rubber, Dacron® polyester, polyvinyl chloride, thermoplastic rubbers, nitrile rubber, butyl rubber, sulfide rubber, polyvinyl acetate, methyl rubber, buna N, buna S, polystyrene, ethylene propylene polymers, polybutadiene, butadiene styrene rubber, and silicone rubbers. The most preferred elastomeric foam materials in the current art of the shoe sole midsole materials are polyurethanes, ethylene vinyl acetate, ethylene vinyl acetate/polyethylene copolymers, ethylene vinyl acetate/polypropylene copolymers, neoprene and polyester elastomers. Suitable materials are selected on the basis of durability, flexibility and resiliency for cushioning and supporting the foot, among other properties, such as protecting and insulating.

Figure 11D:
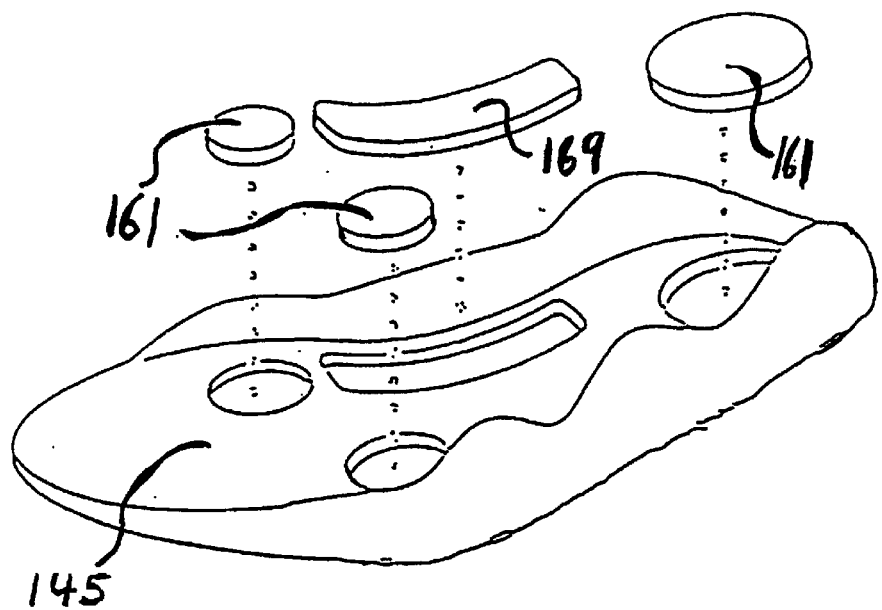
FIG. 11D is an exploded view of an embodiment of an insertable orthotic midsole in accordance with the present invention.

As shown in FIG. 11D, the insertable midsole orthotic 145 itself can incorporate cushioning or structural compartments or components. FIG. 11D shows cushioning compartments or chambers 161 encapsulated in part of the insertable midsole orthotic 145, as well as bottom sole 149, as viewed in a frontal plane cross-section. FIG. 11D is a perspective view indicating the placement of disks or capsules of cushioning material. The disks or capsules of cushioning material may be made from any of the midsole materials mentioned above, and preferably include a flexible, resilient midsole material such as ethyl vinyl acetate (EVA), that may be softer or firmer than other sole material or may be provided with special shock absorption, energy efficiency, wear, or stability characteristics. The disks or capsules may include a gas, gel, liquid or any other suitable cushioning material. The cushioning material may optionally be encapsulated itself using a film made of a suitable material such as polyurethane film. Other similar materials may also be employed. The encapsulation can be used to form the cushioning material into an insertable capsule in a conventional manner. The example shown in FIG. 11D shows such cushioning disks 161 located in the heel area and the lateral and medial forefoot areas, proximate to the heads of the first and fifth metatarsal bones of a wearer's foot. The cushioning material, for example disks or compartments 161, may form part of the upper surface of the upper portion of the insertable midsole orthotic 145 as shown in FIG. 11D. A cushioning compartment or disk 161 can generally be placed anywhere in the insertable midsole orthotic 145 or in only a part of the insertable midsole orthotic 145. A part of the cushioning compartment or disk 161 can extend into the outer sole 149 or other sole portion or, alternatively, one or more compartments or disks 161 may constitute all or substantially all of the insertable midsole orthotic 145. As shown in FIG. 11L, cushioning disks or compartments 161 may also be suitably located at other essential support elements like the base of the fifth metatarsal 97, the head of the first distal phalange 98, or the base and lateral tuberosity of the calcaneus 95, among other suitable conventional locations. In addition, structural components like a shank 169 can also be incorporated partially or completely in an insertable midsole orthotic 145, such as in the medial midtarsal area, as shown in FIG. 11D, under the main longitudinal arch of a wearer's foot, and/or under the base of the wearer's fifth metatarsal bone, or other suitable alternative locations.

In one embodiment, the FIG. 11D invention can be made of all mass-produced standard size components, rather than custom fit, but can be individually tailored for the right and left shoe with variations in the firmness of the material in compartments 161 for special applications such as sport shoes, golf shoes or other shoes which may require differences between firmness of the left and right shoe sole.

One of the advantages provided by the insertable midsole orthotic 145 of the present invention is that it allows replacement of foamed plastic portions of the midsole which degrade quickly with wear, losing their designed level of resilience, with new midsole material as necessary over the life of the shoe to thereby maintain substantially optimal shock absorption and energy return characteristics of the rounded shoe sole 28.

The insertable midsole orthotic 145 can also be transferred from one pair of shoes composed generally of shoe uppers and bottom sole like FIG. 11C to another pair like FIG. 11C, providing cost savings.

Besides using the insertable midsole orthotic 145 to replace worn components with new components, the replacement insertable midsole orthotic 145 can provide another advantage of allowing the use of different cushioning or support characteristics in a single shoe or pair of shoes made like FIG. 11C, such as firmer or softer portions of the midsole or thicker or thinner portions of the midsole, or entire midsoles that are firmer, softer, thicker or thinner, either as separate layers or as an integral part of insertable midsole orthotic 145. In this manner, a single pair of shoes can be customized to provide the desired cushioning or support characteristics for a particular activity or different levels of activity, such as running, training or racing shoes. FIG. 11D shows an example of such insertable portions of the midsole in the form of disks or capsules 161, but midsole or insole layers or the entire midsole section can be removed and replaced temporarily or permanently.

Such insertable midsole orthotics 145 can be made to include density or firmness variations like those shown in FIGS. 21–23 and 25. The midsole density or firmness variations can differ between a right foot shoe and a left foot shoe, such as FIG. 21 as a left shoe and FIG. 22 as a right shoe, showing equivalent portions.

Such replacement insertable midsole orthotics 145 can be made to include thickness variations, including those shown in FIGS. 17–20, 24, 27, or 28. Combinations of density or firmness variations and thickness variations shown above can also be made in the insertable midsole orthotics 145.

Replacement insertable midsole orthotics 145 may be held in position at least in part by enveloping sides of the shoe upper 21 and/or bottom sole 149. Alternatively, a portion of the midsole material may be fixed in the shoe sole and extend up the sides to provide support for holding insertable midsole orthotics 145 in place. If the associated rounded shoe sole 28 has one or more of the abbreviated sides shown in FIG. 11L, then the insertable midsole orthotic 145 can also be held in position against relative motion in the sagittal plane by indentations formed between one or more concavely rounded sides and the adjacent abbreviations. Combinations of these various embodiments may also be employed.

The insertable midsole orthotic 145 has a lower surface interface 8 with the upper surface of the bottom sole 149. The interface 8 would typically remain unglued, to facilitate repeated removal of the insertable midsole orthotic 145, or could be affixed by a weak glue, like that of self-stick removable paper notes, that does not permanently fix the position of the insertable midsole orthotic 145 in place.

The interface 8 can also be bounded by non-slip or controlled slippage surfaces. The two surfaces which form the interface 8 can have interlocking complementary geometries as shown, for example, in FIGS. 11E–11F, such as mating protrusions and indentations, or the insertable midsole orthotic 145 may be held in place by other conventional temporary attachments, such as, for example Velcro® strips. Conversely, providing no means to restrain slippage between the surfaces of interface 8 may, in some cases, provide additional injury protection. Thus, controlled facilitation of slippage at the interface 8 may be desirable in some instances and can be utilized within the scope of the invention.

It is presently contemplated that the insertable midsole orthotics 145, particularly including those involving more complex midsole variations, such as those involving material or structural asymmetry between right and left shoes, would necessarily be prescribed by health care professionals, such as podiatrists or orthopedic or other physicians, in order to provide the maximum benefits and safety of such midsole sections. Such complex midsole variations can also be prescribed for corrective, therapeutic, prosthetic and other purposes by health care professionals.

The insertable midsole orthotic 145 of the present invention may be inserted and removed in the same manner as conventional removable insoles or conventional midsoles, that is generally in the same manner as the wearer inserts his foot into the shoe. Insertion of the insertable midsole orthotic 145 may, in some cases, require loosening of the shoe laces or other mechanisms for securing the shoe to a wearer's foot. For example, the insertable midsole orthotic 145 may be inserted into the interior cavity of the shoe upper and affixed to or abutted against the top side of the shoe sole 28. In a particularly preferred embodiment, a bottom sole 149 is first inserted into the interior cavity of the shoe upper 21 as indicated by the arrow in FIG. 75A. The bottom sole 149 is inserted into the cavity so that any rounded stability sides 28a are inserted into and protrude out of corresponding openings in the shoe upper 21. The bottom sole 149 is then attached to the shoe upper 21, preferably by a stitch that weaves around the outer perimeter of the openings thereby connecting the shoe upper 21 to the bottom sole 149. In addition, an adhesive can be applied to the surface of the shoe upper 21 which will contact the bottom sole 149 before the bottom sole 149 is inserted into the shoe upper 21.

Figure 75A:
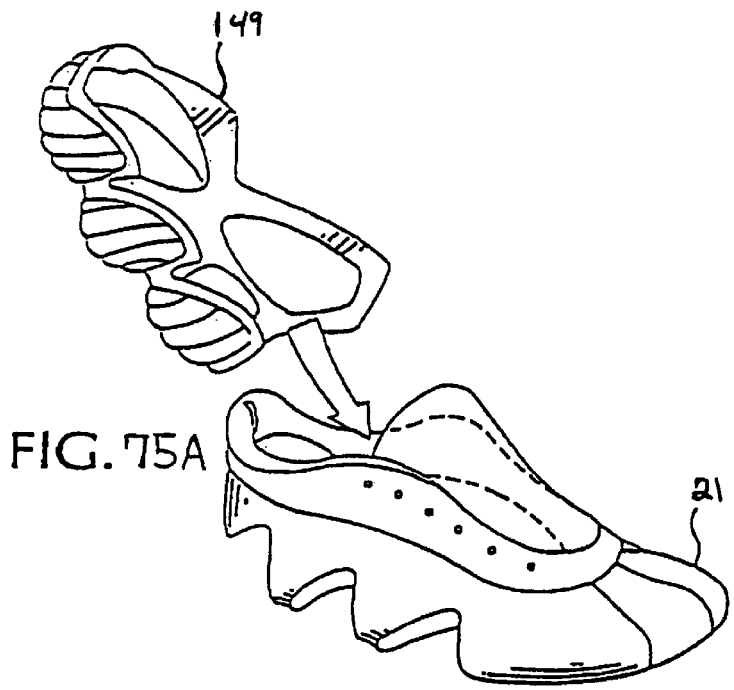
Figure 75B:
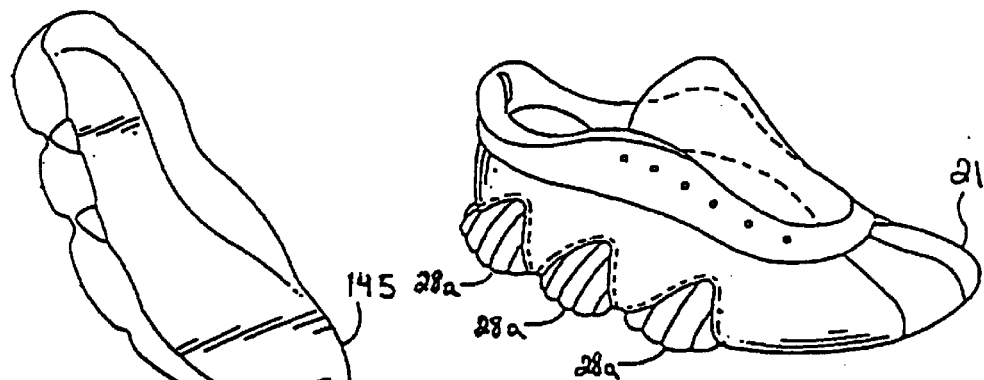
Figure 75C:
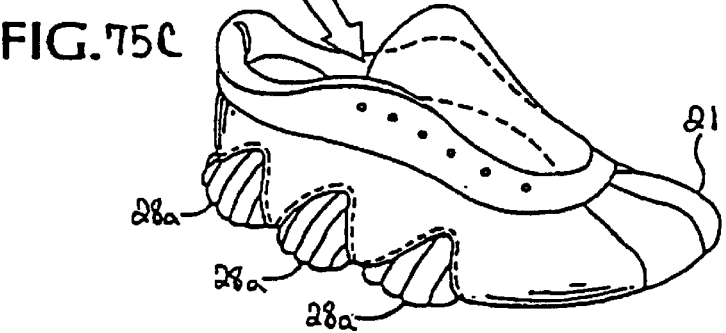

Once the bottom sole 149 is attached, the insertable midsole orthotic 145 may then be inserted into the interior cavity of the shoe upper 21 and affixed to the top side of the bottom sole 149, as shown in FIG. 75C. The insertable midsole orthotic 145 can be releasably secured in place by any suitable method, including mechanical fasteners 301, adhesives 302, snap-fit arrangements 303, reclosable compartments, interlocking geometries 176, 177, and other similar structures. Additionally, the insertable midsole orthotic 145 preferably includes protrusions 176 placed in an abutting relationship with the bottom sole 149 so that the protrusions 176 occupy corresponding recesses 177 in the bottom sole 149.

Alternatively, the insertable midsole orthotic 145 may be glued to affix the insertable midsole orthotic 145 in place on the bottom sole 149. In such an embodiment, an adhesive can be used on the bottom side of the insertable midsole orthotic 145 to secure the midsole to the bottom sole 149.

Replacement insertable midsole orthotics 145 with concavely rounded sides that provide support for only a narrow range of sideways motion or with higher concavely rounded sides that provide for a very wide range of sideways motion can be used to adapt the same shoe for different sports, like running or basketball, for which lessor or greater protection against ankle sprains may be considered necessary, as shown in FIG. 11G. Different insertable midsole orthotics 145 may also be employed on the left or right side, respectively. Replacement insertable midsole orthotics 145 with higher curved sides that provide for an extra range of motion for sports which tend to encourage pronation-prone wearers on the medial side, or on the lateral side for sports which tend to encourage supination-prone wearers are other potentially beneficial embodiments.

Individual insertable midsole orthotics 145 can be custom made for a specific class of wearer or can be selected by the health professional from mass-produced standard sizes with standard variations in the height of the concavely rounded sides, for example.

FIGS. 11M–11P show shoe soles with one or more encapsulated midsole sections or chambers such as bladders 188 for containing fluid such as a gas, liquid, gel or other suitable materials, and with a duct, a flow regulator, a sensor, and a control system such as a microcomputer. The existing art is described by U.S. Pat. No. 5,813,142 by Demon, issued Sep. 29, 1998 and by the references cited therein.

Figure 11E:
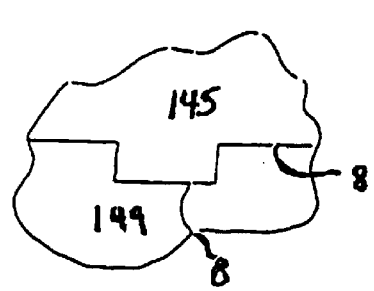
FIGS. 11E–11F are cross-sectional views of alternative embodiments of interlocking interfaces for releasably securing the insertable orthotic midsole of the present invention.
Figure 11S:
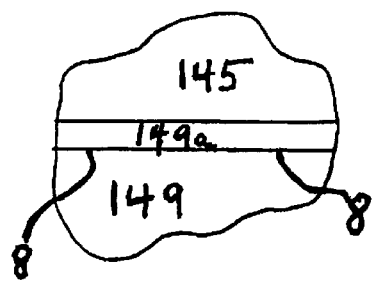
FIG. 11S is a cross-sectional view of an embodiment of an interface for increasing the stability of the insertable orthotic midsole of the present invention
Figure 11F:
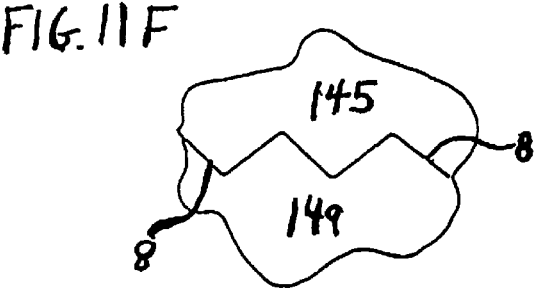
Figure 11M:
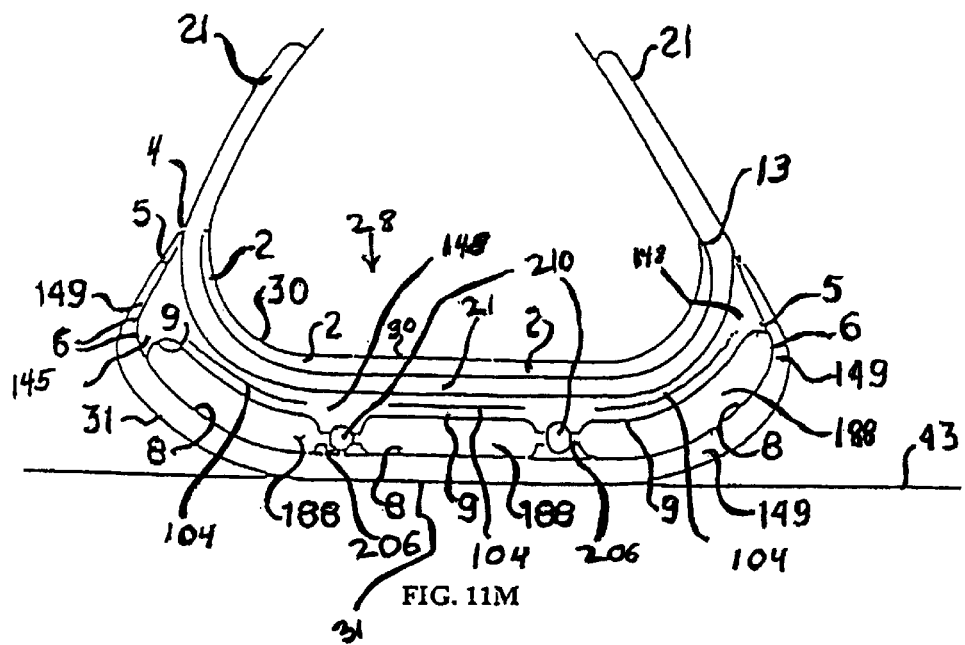
Figure 11N:
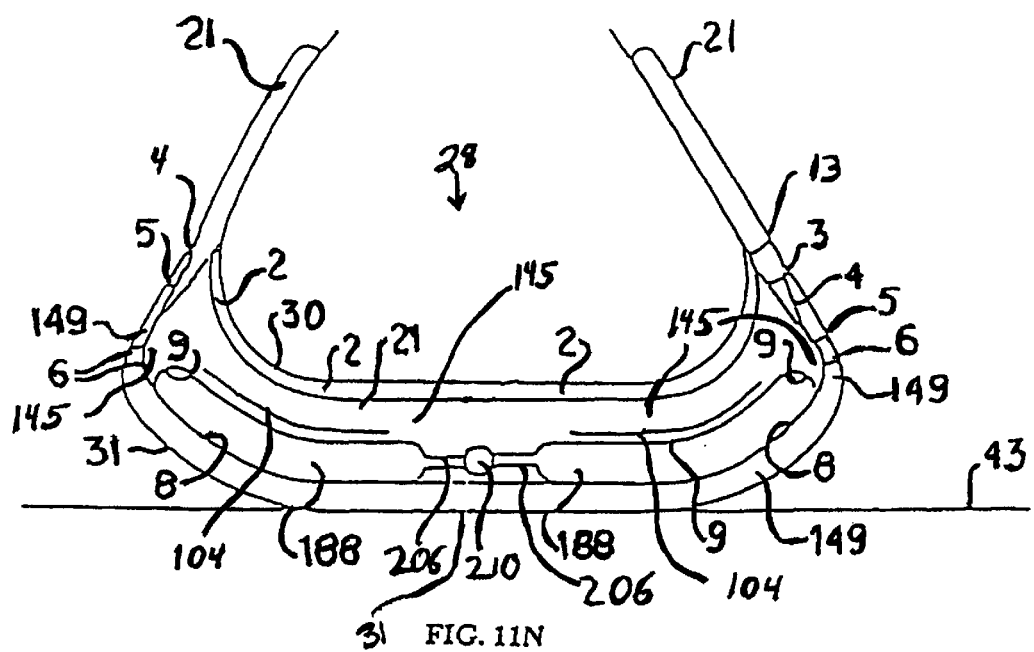
Figure 110:
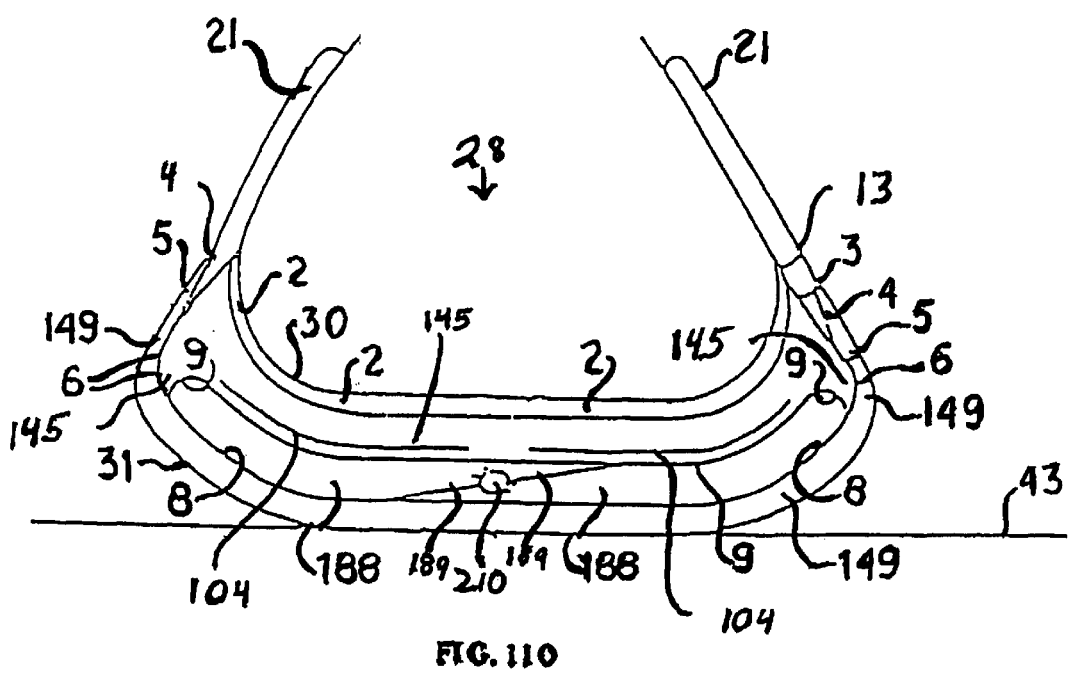
Figure 11P:
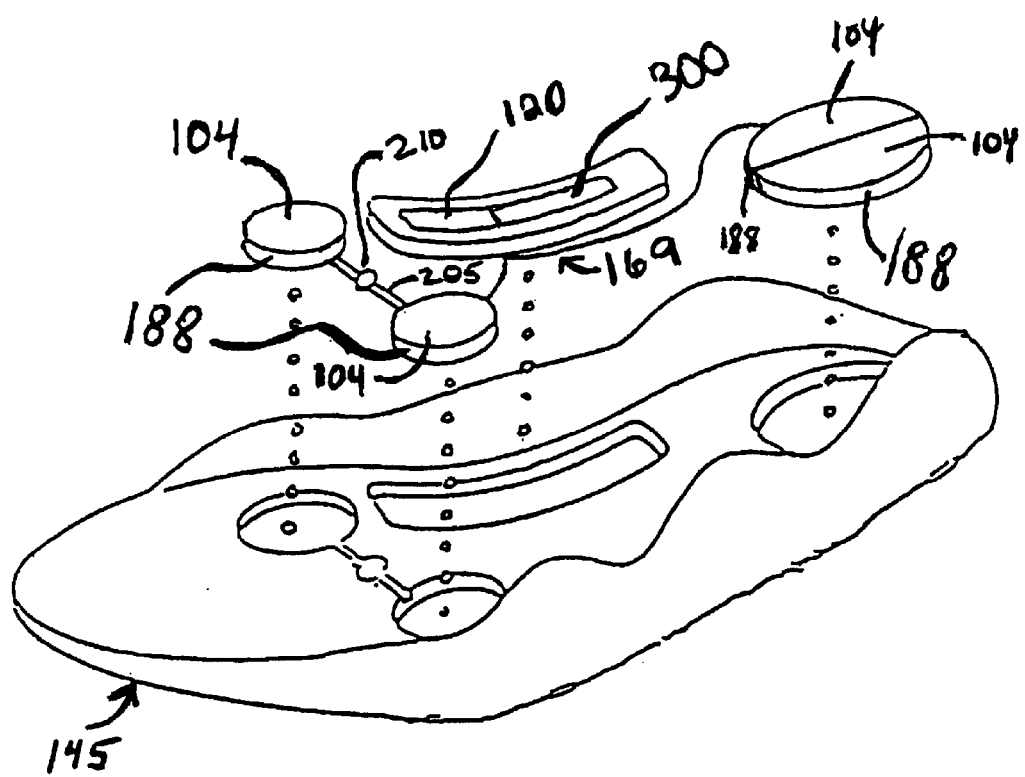
FIG. 11P is an exploded view of an embodiment of a removable insertable midsole orthotic with pressure controlled encapsulated midsole sections and a control system such as a microprocessor.

FIGS. 11M–11P also include the inventor's concavely rounded sides as described elsewhere in this application, such as FIGS. 11A–11L (and/or concavely rounded underneath portions). In addition, FIGS. 11M–11P show ducts that communicate between encapsulated midsole sections or bladders 188 or within portions of the encapsulated midsole section chambers or bladders 188. Other suitable conventional embodiments can also be used in combination with the applicant's concavely rounded portions. Also, FIGS. 11N–11P show insertable midsole orthotics 145. FIG. 11M shows a non-removable midsole 148 in combination with the pressure controlled bladder or encapsulated section 188 of the invention. The bladders or sections 188 can be any size relative to the midsole encapsulating them, including replacing the encapsulating midsole substantially or entirely.

Also, included in the applicant's invention, but not shown, is the use of a piezo-electric effect controlled by the microprocessor control system to affect the hardness or firmness of the material contained in the encapsulated midsole section, bladder, or other encapsulated midsole section 188. For example, a disk-shaped midsole or other suitable material section 161 may be controlled by electric current flow instead of fluid flow with common electrical components replacing those described below which are used for conducting and controlling fluid flow under pressure.

FIG. 11M shows a shoe sole with the applicant's concavely rounded sides, invention described in earlier figures including both concavely rounded sole inner and outer surfaces, with a bladder or an encapsulated midsole section 188 in both the medial and lateral sides and in the middle or underneath portion between the sides. An embodiment with a bladder or encapsulated midsole section 188 located in only a single side and the middle portion is also possible, but not shown, as is an embodiment with a bladder or encapsulated midsole section 188 located in both the medial and lateral sides without one in the middle portion. Each of the sections or bladders 188 is connected to an adjacent bladder(s) 188 by a fluid duct 206 passing through a fluid valve 210, located in midsole 148, although the location could be anywhere in a single or multi-layer rounded shoe sole 28. FIG. 11M is based on the left side of FIG. 13A. In a piezo-electric embodiment using bladders or encapsulated midsole sections 188, the fluid duct between sections would be replaced by a suitable wired or wireless connection, not shown. A combination of one or more bladders 188 with one or more encapsulate midsole sections 188 is also possible but not shown.

One advantage of the applicant's invention, as shown in the applicant's FIG. 11M, is to provide better lateral or side-to-side stability through the use of rounded sides, to compensate for excessive pronation or supination or both when standing or during locomotion. The FIG. 11M embodiment also shows a fluid containment system that is fully enclosed and which uses other bladders 188 as reservoirs to provide unique advantage. The advantage of FIG. 11M embodiment is to provide a structural means by which to change the hardness or firmness of each of the shoe sole sides and of the middle or underneath sole portion relative to the hardness or firmness of each of the other sides or sole portion, as seen for example in a frontal plane, as shown, or in a sagittal plane (not shown).

Although FIG. 11M shows communication between each bladder or section within a frontal plane (or sagittal plane), which is a highly effective embodiment, communication might also be between only two adjacent or non-adjacent bladders or encapsulated midsole sections 188 due to cost, weight, or other design considerations. The operation of the applicant's invention, beyond that described herein with the exceptions specifically indicated, is as is known in the prior art, specifically the Demon '142 patent, the relevant portions of which, such as the disclosure of a suitable system and electronic shown in schematic representations in FIGS. 2, 6 and 7 of the Demon '142 patent and the pressure sensitive variable capacitor shown in FIG. 5, as well as the textual specification associated with those figures, are hereby incorporated by reference.

Each fluid bladder or encapsulated midsole section 188 may be provided with an associated pressure sensing device that measures the pressure exerted by the user's foot on the fluid bladder or encapsulated midsole section 188. As the pressure increases above a threshold, a control system opens (perhaps only partially) a flow regulator to allow fluid to escape from the fluid bladder 188. Thus, the release of fluid from the fluid bladders 188 may be employed to reduce the impact of the user's foot on the ground. Point pressure under a single bladder 188, for example, can be reduced by a controlled fluid outflow to any other single bladder or any combination of other bladders.

Preferably, the sole of the shoe is divided into zones which roughly correspond to the essential structural support and propulsion elements of the intended wearer's foot, including the base of the calcaneus, the lateral tuberosity of the calcaneus 95, the heads of the metatarsals 96 (particularly the first and fifth), the base of the fifth metatarsal, the main longitudinal arch (optional), and the head of the first distal phalange 98. The zones under each individual element can be merged with adjacent zones, such as a lateral metatarsal head zone 96e and a medial metatarsal head zone 96d.

The pressure sensing system preferably measures the relative change in pressure in each of the zones. The fluid pressure system thereby reduces the impact experienced by the user's foot by regulating the escape of a fluid from a fluid bladder or encapsulated midsole section 188 located in each zone of the sole. The control system 300 receives pressure data from the pressure sensing system and controls the fluid pressure system in accordance with predetermined criteria which can be implemented via electronic circuitry, software or other conventional means.

The pressure sensing system may include a pressure sensing device 104 disposed in the sole of the shoe at each zone. In a preferred embodiment, the pressure sensing device 104 is a pressure sensitive variable capacitor which may be formed by a pair of parallel flexible conductive plates disposed on each side of a compressible dielectric. The dielectric, which can be made from any suitable material such as rubber or another suitable elastomer. The outside of flexible conductive plates are preferably covered by a flexible sheath (such as rubber) for added protection.

Since the capacitance of a parallel plate capacitor is inversely proportional to the distance between the plates, compressing the dielectric by applying greater pressure increases the capacitance of pressure sensitive variable capacitor. When the pressure is released, the dielectric expands substantially to its original thickness so that the pressure sensitive variable capacitor returns substantially to its original capacitance. Consequently, the dielectric must have a relatively high compression limit and a high degree of elasticity to provide ideal function under variable loading.

The pressure sensing system also includes pressure sensing circuitry 120 which converts the change in pressure detected by the variable capacitor into digital data. Each variable capacitor forms part of a conventional frequency-to-voltage converter (FVC) which outputs a voltage proportional to the capacitance of variable capacitor. An adjustable reference oscillator may be electrically connected to each FVC. The voltage produced by each of the FVC's is provided as an input to a multiplexer which cycles through the channels sequentially connecting the voltage from each FVC to an analog-to-digital (A/D) converter to convert the analog voltages into digital data for transmission to control system 300 via data lines, each of which is connected to control system 300. The control system 300 can control the multiplexer to selectively receive data from each pressure sensing device in any desirable order. These components and circuitry are well known to those skilled and the art and any suitable component or circuitry might be used to perform the same function.

The fluid pressure system selectively reduces the impact of the user's foot in each of the zones. Associated with each pressure sensing device 104 in each zone, and embedded in the shoe sole, is at least one bladder or encapsulated midsole section 188 which forms part of the fluid pressure system. A fluid duct 206 is connected at its first end to its respective bladder or encapsulated midsole section 188 and is connected at its other end to a fluid reservoir. In this embodiment, fluid duct 206 connects bladder or encapsulated midsole section 188 with ambient air, which acts as a fluid reservoir, or in a different embodiment, with another bladder 188 also acting as a fluid reservoir. A flow regulator, which in this embodiment is a fluid valve 210, is disposed in fluid duct 206 to regulate the flow of fluid through fluid duct 206. Fluid valve 210 is adjustable over a range of openings (i.e., variable metering) to control the flow of fluid exiting bladder or section 188 and may be any suitable conventional valve such as a solenoid valve as in this embodiment.

Control system 300, which preferably includes a programmable microcomputer having conventional RAM and/or ROM, receives information from the pressure sensing system indicative of the relative pressure sensed by each pressure sensing device 104. Control system 300 receives digital data from pressure sensing circuitry 120 proportional to the relative pressure sensed by pressure sensing devices 104. Control system 300 is also in communication with fluid valves 210 to vary the opening of fluid valves 210 and thus control the flow of fluid. As the fluid valves of this embodiment are solenoids (and thus electrically controlled), control system 300 is in electrical communication with fluid valves 210. An analog electronic control system 300 with other components being analog is also possible.

The preferred programmable microcomputer of control system 300 selects (via a control line) one of the digital-to-analog (D/A) converters to receive data from the microcomputer to control fluid valves 210. The selected D/A converter receives the data and produces an analog voltage proportional to the digital data received. The output of each D/A converter remains constant until changed by the microcomputer (which can be accomplished using conventional data latches, which is not shown). The output of each D/A converter is supplied to each of the respective fluid valves 210 to selectively control the size of the opening of fluid valves 210.

Control system 300 also can include a cushion adjustment control to allow the user to control the level of cushioning response from the shoe. A control device on the shoe can be adjusted by the user to provide adjustments in cushioning ranging from no additional cushioning (fluid valves 210 never open) to maximum cushioning (fluid valves 210 open wide). This is accomplished by scaling the data to be transmitted to the D/A converters (which controls the opening of fluid valves 210) by the amount of desired cushioning as received by control system 300 from the cushioning adjustment control. However, any suitable conventional means of adjusting the cushioning could be used.

An illuminator, such as a conventional light emitting diode (LED), can be mounted to the circuit board that houses the electronics of control system 300 to provide the user with an indication of the state of operation of the apparatus.

The operation of this embodiment of the present invention is most useful for applications in which the user is either walking or running for an extended period of time during which weight is distributed among the zones of the foot in a cyclical pattern. The system begins by performing an initialization process which is used to set up pressure thresholds for each zone.

During initialization, fluid valves 210 are fully closed while the bladders or sections 188 are in their uncompressed state (e.g., before the user puts on the shoes). In this configuration, no fluid, including a gas like air, can escape the bladders or encapsulated midsole sections 188 regardless of the amount of pressure applied to the bladders or sections 188 by the user's foot. As the user begins to walk or run with the shoes on, control system 300 receives and stores measurements of the change in pressure of each zone from the pressure sensing system. During this period, fluid valves 210 are kept closed.

Next, control system 300 computes a threshold pressure for each zone based on the measured pressures for a given number of strides. In this embodiment, the system counts a predetermined number of strides, i.e. ten strides (by counting the number of pressure changes), but another system might simply store data for a given period of time (e.g. twenty seconds). The number of strides are preprogrammed into the microcomputer but might be inputted by the user in other embodiments. Control system 300 then examines the stored pressure data and calculates a threshold pressure for each zone. The calculated threshold pressure, in this embodiment, will be less than the average peak pressure measured and is in part determined by the ability of the associated bladder or section 188 to reduce the force of the impact as explained in more detail below.

After initialization, control system 300 will continue to monitor data from the pressure sensing system and compare the pressure data from each zone with the pressure threshold of that zone. When control system 300 detects a measured pressure that is greater than the pressure threshold for that zone, control system 300 opens the fluid valve 210 (in a manner as discussed above) associated with that pressure zone to allow fluid to escape from the bladder or section 188 into the fluid reservoir at a controlled rate. In this embodiment, air escapes from bladder or section 188 through fluid duct 206 (and fluid valve 210 disposed therein) into ambient air. The release of fluid from the bladder or section 188 allows the bladder or section 188 to deform and thereby lessens the "push back" of the bladder. The user experiences a "softening" or enhanced cushioning of the sole of the shoe in that zone, which reduces the impact on the user's foot in that zone.

The size of the opening of fluid valve 210 should allow fluid to escape the bladder or section 188 in a controlled manner. The fluid should not escape from bladder or section 188 so quickly that the bladder or section 188 becomes fully deflated (and can therefore supply no additional cushioning) before the peak of the pressure exerted by the user. However, the fluid must be allowed to escape from the bladder or section 188 at a high enough rate to provide the desired cushioning. Factors which will bear on the size of the opening of the flow regulator include the viscosity of the fluid, the size of the fluid bladder, the pressure exerted by fluid in the fluid reservoir, the peak pressure exerted and the length of time such pressure is maintained.

As the user's foot leaves the traveling surface, a fluid like air is forced back into the bladder or section 188 by a reduction in the internal air pressure of the bladder or section 188 (i.e., a vacuum is created) as the bladder or section 188 returns to its non-compressed size and shape. After control system 300 receives pressure data from the pressure sensing system indicating that no pressure (or minimal pressure) is being applied to the zones over a predetermined length of time (long enough to indicate that the shoe is not in contact with the traveling surface and that the bladders or sections 188 have returned to their non-compressed size and shape), control system 300 again closes all fluid valves 210 in preparation for the next impact of the user's foot with the traveling surface.

Pressure sensing circuitry 120 and control system 300 are mounted to the shoe and are powered by a common, conventional battery supply. As pressure sensing device 104 and the fluid system are generally located in the sole of the shoe, the described electrical connections are preferably embedded in the upper and the sole of the shoe.

The FIG. 11M embodiment can also be modified to omit the be applicant's concavely rounded sides and can be combined with the various features of any one or more of the other figures included in this application, as can the features of FIGS. 11N–11P. Pressure sensing devices 104 are also shown in FIG. 11M. A control system 300, such as a microprocessor as described above, forms part of the embodiment shown in FIG. 11M (and FIGS. 11N–11O) embodiments, but is not shown in the frontal plane cross section.

FIG. 11N shows the application of the FIG. 11M concept as described above in combination with an insertable midsole orthotic 145 invention. One significant advantage of this embodiment, besides improved lateral stability, is that the potentially most expensive component of the shoe sole, the insertable midsole orthotic 145, can be moved to other pairs of shoe upper/bottom shoes, whether new or having a different style or function. Separate removable insoles can be useful in this case, especially in changing from athletic shoes to dress shoes for function and/or style. FIG. 11N shows a simplified embodiment of only two bladders 188 or encapsulated midsole sections 188, each of which extends from a concavely rounded side to the central portion. FIG. 11N is based on the right side of FIG. 13A.

The FIG. 11O embodiment is similar to the FIG. 11N embodiment, except that only one bladder or encapsulated midsole section 188 is shown, separated centrally by a wall 189 containing a fluid valve communicating between the two separate parts of the section or bladder 188. The angle of the separating wall 189 provides a gradual transition from the pressure of the left compartment to the pressure of the right compartment, but is not required. Other structures may be present within or outside the section or bladder 188 for support or other purposes, as is known in the art.

FIG. 11P is a perspective view of the applicant's invention, including the control system 300, such as a microprocessor, and pressure-sensing circuitry 120, which can be located anywhere in the insertable midsole orthotic 145 shown, in order for the entire unit to be removable as a single piece, with placement in the shank shown proximate the main longitudinal arch of the wearer's foot shown in this figure, or alternatively, located elsewhere in the shoe, potentially with a wired or wireless connection and potentially separate means of attachment. The heel bladder 188 shown in FIG. 11P is similar to that shown in FIG. 11O with both lateral and medial chambers.

Like FIG. 11M, FIGS. 11N–11P operate in the manner known in the art as described above, except as otherwise shown or described herein by the applicant, with the applicant's depicted embodiments being preferred but not required.

The embodiments shown in FIGS. 11M–11P can also include the capability to function sufficiently rapidly to sense an unstable shoe sole condition such as, for example, that initiating a slip, trip, or fall, and to react to the unstable shoe condition in order to promote a stable or more stable shoe sole condition. In this manner, the system can attempt to prevent a fall or at least attempt to reduce associated injuries, for example, by rapidly reducing high point pressure in one zone of the shoe sole so that pressures in all zones are quickly equalized to restore the stability of the shoe sole.

The insertable midsole orthotic 145 invention, for example as shown in FIG. 11A–11P, can also be used in combination with, or to implement, one or more features of any of the applicant's prior inventions shown in the other figures in this application. Such use can also include a combination of features shown in any other figures of the present application. For example, the insertable midsole orthotic 145 of the present invention may replace all or any portion or portions of the various midsoles, insoles and bottom soles which are shown in the figures of the present application, and may be combined with the various other features described in reference to any of these figures in any of these forms.

The insertable midsole orthotic 145 shown in FIGS. 11A–11P can be integrated into, or may replace an orthotic or other podiatric, orthopedic, corrective, therapeutic, prosthetic, prescriptive, or similar device for use inside the wearer's shoe. Such devices can be rigid, but flexible devices are preferred. A more conventional device such as an orthotic without concavely rounded sides or lower surface can be placed on top of the midsole, or between the midsole and an insole, on top of the midsole, or in any other suitable location. Other portions of the shoe sole 28 may include the concavely rounded side or sides or underneath portions.

If the insertable midsole orthotic 145 is used to replace an orthotic, for example, then any of the features of an orthotic can be provided by an equivalent feature, structural support, cushioning or otherwise, in the insertable midsole orthotic 145. If a midsole is integrated with an insertable midsole orthotic 145, for example, then the midsole might be a mass-produced lower layer providing cushioning and support, as well as heel lift, while the insertable midsole orthotic 145 might be rounded to the exact shape of the individual wearer's foot and could provide other structural or functional corrections specific to the individual wearer. Alternatively, part of the correction might be made in the midsole, such as, for example, the provision of a medial side increase in material firmness to compensate for an individual wearer's excessive pronation.

As shown in FIGS. 11Q and 11R, the insertable midsole orthotic 145 can include its own integral inner or secondary upper 21a, such as a bootie or slipper incorporating stretchable fabric, i.e. elastic or Spandex®, non-stretchable fabric or both, with typical attachment means such as laces, straps, Velcro® and zippers, or simply be a slip-on structure, like a slipper or loafer or pull-on boot.

FIGS. 11Q and 11R also show the insertable midsole orthotic 145 with its own thin outer sole 149a such as of rubber or other suitable, typical material for wear protection of the midsole and for traction, so that the insertable midsole orthotic 145 can be worn indoors, for example, without the shoe upper 21 and outer sole 149, but can also be inserted into, for example, the FIG. 11C upper and sole for heavier use, such as walking outdoors or engaging in athletics. Separate components or an entire outer sole 149 can also be affixed directly to the insertable midsole orthotic 145 with a sufficiently durable secondary upper 21a using conventional means for affixing it, such as the interface surface 8 of the outer soles 149 and 149a interlocking geometrically, as shown in FIGS. 11E and 11F, in conjunction with straps, or with straps alone, roughly in the manner of sandals. Similarly, all or part of the shoe upper 21 can be affixed through conventional means to the secondary shoe upper 21a, independently of the outer sole 149 or in combination with it.

FIGS. 11Q–11S show an embodiment of an orthotic inner shoe in accordance with the present invention. FIG. 11Q shows, in frontal plane cross section, an embodiment with a very thin coat of traction material such as latex rubber forming a secondary outer sole 149a which provides traction to prevent slipping and also protects the insertable midsole orthotic 145 underneath from wear, and a lowtop slipper inner upper 21a. Such a latex rubber coat can be applied in a continuous manner over part or all of the outer surface of the secondary outer sole 149a or can be applied in a regular pattern, like dots or circles, as is typical to provide better grip for gloves, or can even be applied in a random pattern.

FIG. 11R shows, in frontal plane cross section, another embodiment with a secondary bottom or outer sole 149a of a rubber material that might be as thin as 1 millimeter, for example, to protect just that part of the insertable midsole orthotic 145 which makes contact with the ground 43 when the intended wearer's foot is upright and therefore that midsole part which would wear most quickly due to a high level of ground contact. Other suitable outsole material can be used. Although not shown, the secondary outer sole 149a can id extend part or all the way up either or both of the rounded shoe sole lateral and medial sides.

FIG. 11R also shows a lowtop slipper inner secondary upper 21a which can envelop all or a portion of the midsole sides, including joining with the secondary outer sole 149a, such as overlapping it on the inside between the insertable midsole orthotic 145 and the outer sole 149a. FIG. 11Q shows the secondary upper 21a connecting to the insole 2. The secondary upper 21a can also envelop the insole, although not shown.

FIG. 11S shows in close-up cross section the interface surface 8 between the bottom sole 149 and the secondary bottom sole 149a of the insertable midsole orthotic 145. Direct contact, as shown of the rubber or rubber-like materials or 149 and 149a, provides an excellent means inside the shoe sole to prevent internal slipping due to shear forces at the interface surface 8, thereby increasing the stability of the shoe sole. Therefore, removal of typical materials other than those of 149 and 149a, such as board last material, increases stability.

This can be accomplished by outright removal of a board last after the upper to which it is attached has been assembled on a last or assembling without a lasting board. Alternatively, by using a board last with holes or sections removed so that direct contact can occur at 149 and 149a; such holes or sections can be random or regular, including simply a very loose weave fabric, or can coincide with some or all of the essential support and propulsion elements of the foot described earlier, such as the pattern shown in FIG. 70.

In an advantageous embodiment, most or all of the corrective portion of the insertable midsole orthotic 145, such as special shaping or increased density inserts to compensate for an individual wearer's structural defects, is located in the upper portion of the insertable midsole orthotic 145 where it is accessible through the opening of the secondary upper 21a for alteration so that it can be modified to better compensate for defects based on testing and usage of the intended wearer.

In another advantageous embodiment, only this uppermost corrective portion is the insertable midsole orthotic 145, while the lower portion of the midsole is fixed in a conventional manner in the shoe sole. Such an embodiment can still be constructed using the embodiments described above, including FIGS. 11A–11S, especially including FIGS. 11Q–11R, and the compartments with computer control mechanisms, particularly as shown in FIG. 11P. The uppermost insertable midsole orthotic 145 might include the relatively expensive computer microprocessor and associated memory, for example, which might communicate with the remaining portions of the compartment pressure controlling system using a wireless communication system.

In one advantageous embodiment, the thickness of the uppermost portion of the insertable midsole orthotic 145 as described in FIGS. 11A–11S can be any thickness less than half of the thickness of the shoe sole, including, but not limited to, in a comparison of median thicknesses. In other embodiments, the thickness may be substantially less than half, for example, 40% of the total thickness, 30% of the total thickness or even up to 20% of the total thickness.

Figure 11T:
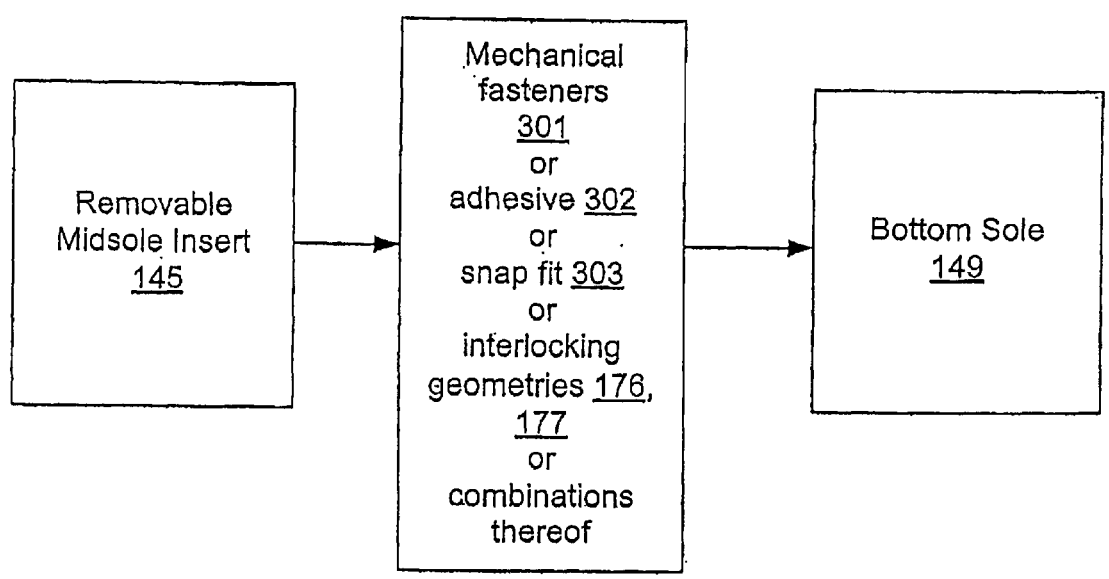
FIG. 11T is a schematic representation of various mechanisms for removably securing the insertable midsole orthotic to the shoe.

FIG. 11T is a schematic representation of various means for releasably securing the insertable midsole orthotic 145 of the present invention to the bottom sole 149. More specifically, FIG. 11T shows the alternatives of releasably securing the removable midsole insert 145 to the bottom sole via mechanical fasteners 301, adhesive 302, snap fit 303, interlocking geometries 176, 177 or combinations thereof.

Figure 12A:
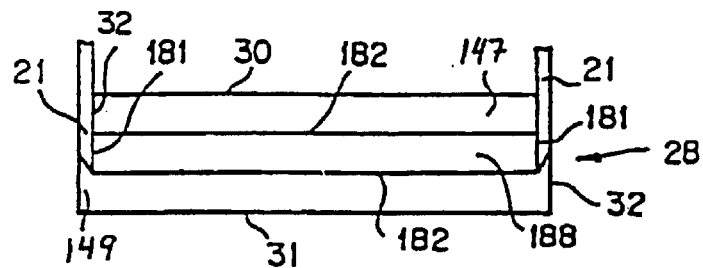
FIGS. 12A–12C show a series of conventional shoe sole cross sections in the frontal plane at the heel utilizing both sagittal plane and horizontal plane sipes, and in which some or all of the sipes do not originate from any outer shoe sole surface, but rather are entirely internal
Figure 12B:
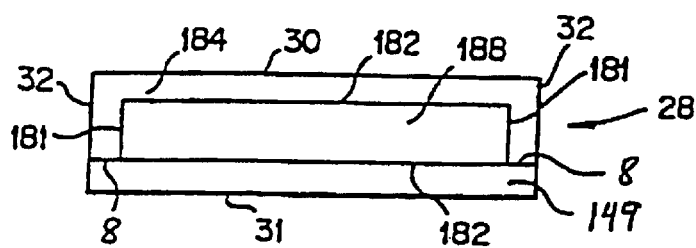
Figure 12C:
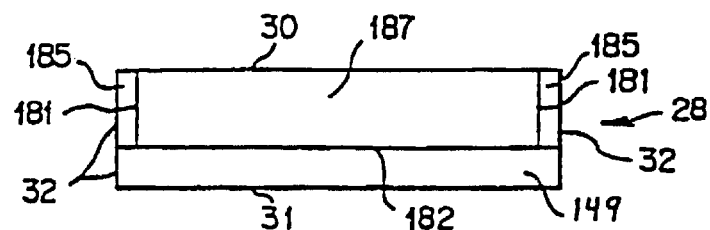

FIGS. 12A–C show a series of conventional shoe sole cross sections in the frontal plane at the heel utilizing both sagittal plane 181 and horizontal plane sipes 182, and in which some or all of the sipes do not originate from any outer shoe sole surface, but rather are entirely internal. Relative motion between internal surfaces is thereby made possible to facilitate the natural deformation of the shoe sole.

FIG. 12A shows a group of three midsole section or lamination layers. Preferably, the central layer 188 is not glued to the other surfaces in contact with it. Instead, those surfaces are internal deformation sipes in the sagittal plane 181 and in the horizontal plane 182, which encapsulate the central layer 188, either completely or partially. The relative motion between midsole section layers at the deformation sipes 181 and 182 can be enhanced with lubricating agents, either wet like silicone or dry like Teflon, of any degree of viscosity. Shoe sole materials can be closed cell if necessary to contain the lubricating agent or a non-porous surface coating or layer of lubricant can be applied. The deformation sipes can be enlarged to channels or any other practical geometric shape as sipes defined in the broadest possible terms.

The relative motion can be diminished by the use of roughened surfaces or other conventional methods of increasing the coefficient of friction between midsole section layers. If even greater control of the relative motion of the central layer 188 is desired, as few as one or many more points can be glued together anywhere on the internal deformation sipes 181 and 182, making them discontinuous, and the glue can be any degree of elastic or inelastic.

In FIG. 12A, the outside structure of the sagittal plane deformation sipes 181 is the shoe upper 21, which is typically flexible and relatively elastic fabric or leather. In the absence of any connective outer material like the shoe upper shown in FIG. 12A, just the outer edges of the horizontal plane deformation sipes 182 can be glued together.

FIG. 12B shows another conventional shoe sole in frontal plane cross section at the heel with a combination similar to FIG. 12A of both horizontal and sagittal plane deformation sipes that encapsulate a central section 188. Like FIG. 12A, the FIG. 12B structure allows the relative motion of the central section 188 with its encapsulating outer midsole section 184, which encompasses its sides as well as the top surface, and bottom sole 149, both of which are attached at their common boundaries 8.

This FIG. 12B approach is analogous to the applicant's fully rounded shoe sole invention with an encapsulated midsole chamber of a pressure-transmitting medium like silicone; in this conventional shoe sole case, however, the pressure-transmitting medium is a more conventional section of a typical shoe cushioning material like PV or EVA, which also provides cushioning.

FIG. 12C is another conventional shoe sole shown in frontal plane cross section at the heel with a combination similar to FIGS. 12A and 12B of both horizontal and sagittal plane deformation sipes. However, instead of encapsulating a central section 188, in FIG. 12C an upper section 187 is partially encapsulated by deformation sipes so that it acts much like the central section 188, but is more stable and more closely analogous to the actual structure of the human foot.

The upper section 187 would be analogous to the integrated mass of fatty pads, which are U-shaped and attached to the calcaneus or heel bone. Similarly, the shape of the deformation sipes is U-shaped in FIG. 12C and the upper section 187 is attached to the heel by the shoe upper, so it should function in a similar fashion to the aggregate action of the fatty pads. The major benefit of the FIG. 12C invention is that the approach is so much simpler and therefore easier and faster to implement than the highly complicated anthropomorphic design shown in FIG. 10 above. The midsole sides 185 shown in FIG. 12C are like the side portion of the encapsulating midsole 184 in FIG. 12B.

Figure 12D:
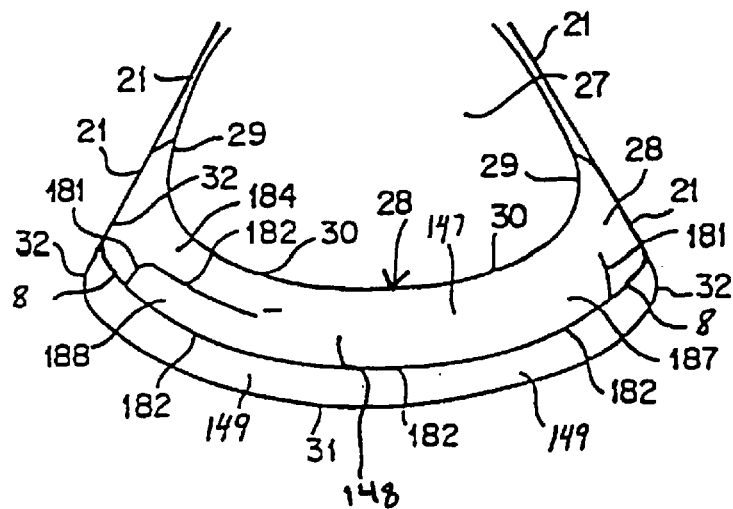
FIG. 12D shows a similar approach as is shown in FIGS. 12A–12C applied to the fully rounded design.

FIG. 12D shows in a frontal plane cross section at the heel a similar approach applied to the applicant's fully rounded design. FIG. 12D shows a design including an encapsulating chamber and a variation of the attachment for attaching the shoe upper to the bottom sole.

The left side of FIG. 12D shows a variation of the encapsulation of a central section 188 shown in FIG. 12B, but the encapsulation is only partial, with a center upper section of the central section 188 either attached or continuous with the encapsulating outer midsole section 184.

The right side of FIG. 12D shows a structure of deformation sipes like that of FIG. 12C, with the upper midsole section 187 provided with the capability of moving relative to both the bottom sole and the side of the midsole. The FIG. 12D structure varies from that of FIG. 12C also in that the deformation sipe 181 in roughly the sagittal plane is partial only and does not extend to the upper surface 30 of the midsole 147, as it does FIG. 12C.

Figure 13A:
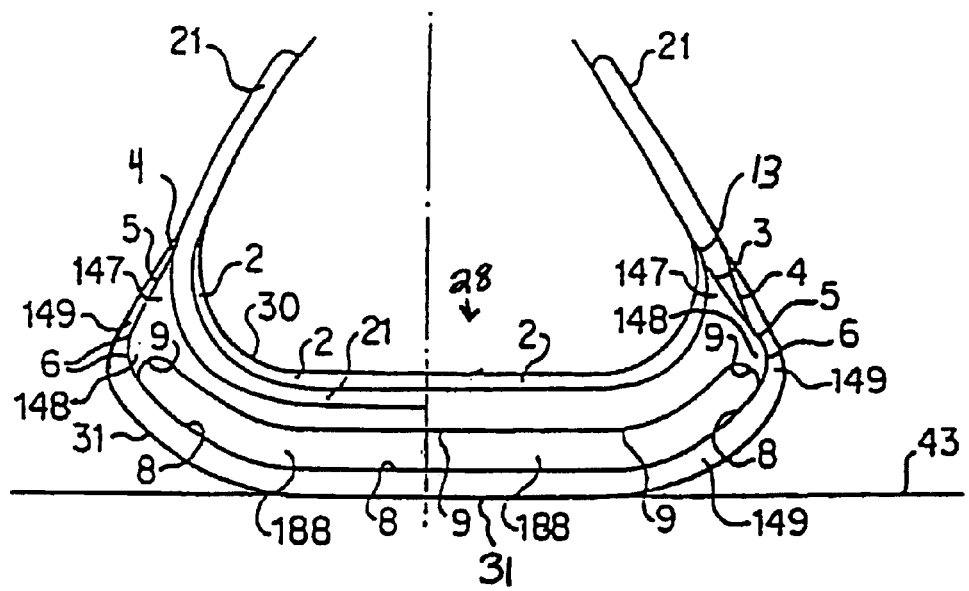
FIGS. 13A–13B show, in frontal plane cross section at the heel area, shoe sole structures similar to those shown in FIGS. 5A–B, but in more detail and with the bottom sole extending relatively farther up the side of the midsole.
Figure 13B:
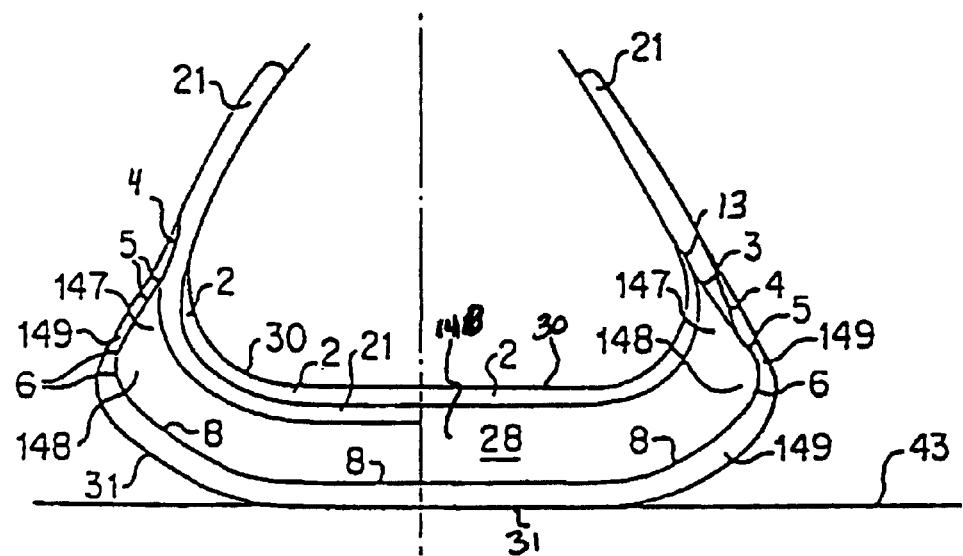

FIGS. 13A&13B show, in frontal plane cross section at the heel area, shoe sole structures like FIGS. 5A&B, but in more detail and with the bottom sole 149 extending relatively farther up the side of the midsole.

The right side of FIGS. 13A&13B show the preferred embodiment, which is a relatively thin and tapering portion of the bottom sole extending up most of the midsole and is attached to the midsole and to the shoe upper 21, which is also attached preferably first to the upper midsole 147 where both meet at 3 and then attached to the bottom sole where both meet at 4. The bottom sole is also attached to the upper midsole 147 where they join at 5 and to the midsole 148 at 6.

The left side of FIGS. 13A&13B show a more conventional attachment arrangement, where the shoe sole is attached to a fully lasted shoe upper 21. The bottom sole 149 is attached to: the midsole 148 where their surfaces coincide at 6, the upper midsole 147 at 5, and the shoe upper 21 at 4.

FIG. 13A shows a shoe sole with another variation of an encapsulated section 188. The encapsulated section 188 is shown bounded by the bottom sole 149 at line 8 and by the rest of the midsole 147 and 148 at line 9. FIG. 13A shows more detail than prior figures, including an insole (also called sock liner) 2, which is rounded to the shape of the wearer's foot sole, just like the rest of the shoe sole, so that the foot sole is supported throughout its entire range of sideways motion, from maximum supination to maximum pronation.

The insole 2 overlaps the shoe upper 21 at 13. This approach ensures that the load-bearing surface of the wearer's foot sole does not come in contact with any seams which could cause abrasions. Although only the heel section is shown in this figure, the same insole structure would preferably be used elsewhere, particularly the forefoot. Preferably, the insole would coincide with the entire load-bearing surface of the wearer's foot sole, including the front surface of the toes, to provide support for front-to-back motion as well as sideways motion.

The FIG. 13 design provides firm flexibility by encapsulating fully or partially, roughly the middle section of the relatively thick heel of the shoe sole (or of other areas of the sole, such as any or all of the essential support elements of the foot, including the base of the fifth metatarsal, the heads of the metatarsals, and the first distal phalange). The outer surfaces of that encapsulated section or sections are allowed to move relatively freely by not gluing the encapsulated section to the surrounding shoe sole.

Firmness in the FIG. 13 design is provided by the high pressure created under multiples of body weight loads during locomotion within the encapsulated section or sections, making it relatively hard under extreme pressure, roughly like the heel of the foot. Unlike conventional shoe soles, which are relatively inflexible and thereby create local point pressures, particularly at the outside edge of the shoe sole, the FIG. 13 design tends to distribute pressure evenly throughout the encapsulated section, so the natural biomechanics of the wearer's foot sole are maintained and shearing forces are more effectively dealt with.

In the FIG. 13A design, firm flexibility is provided by encapsulating roughly the middle section of the relatively thick heel of the shoe sole or other areas of the sole, while allowing the outer surfaces of that section to move relatively freely by not conventionally gluing the encapsulated section to the surrounding shoe sole. Firmness is provided by the high pressure created under body weight loads within the encapsulated section, making it relatively hard under extreme pressure, roughly like the heel of the foot, because it is surrounded by flexible but relatively inelastic materials, particularly the bottom sole 149 (and connecting to the shoe sole upper, which also can be constructed by flexible and relatively inelastic material. The same U-shaped structure is thus formed on a macro level by the shoe sole that is constructed on a micro level in the human foot sole, as described definitively by Erich Blechschmidt in Foot and Ankle, March, 1982.

In summary, the FIG. 13A design shows a shoe construction for a shoe, comprising: a shoe sole with at least one compartment under the structural elements of the human foot; the compartment containing a pressure-transmitting medium composed of an independent section of midsole material that is not firmly attached to the shoe sole surrounding it; pressure from normal load-bearing is transmitted progressively at least in part to the relatively inelastic sides, top and bottom of said shoe sole compartment, producing tension.

The FIG. 13A design can be combined with the designs shown in FIGS. 58–60 so that the compartment is surrounded by a reinforcing layer of relatively flexible and inelastic fiber.

FIGS. 13A&13B shows constant shoe sole thickness in frontal plane cross-sections, but that thickness can vary somewhat (up to roughly 25% in some cases) in frontal plane cross-sections. FIG. 13B shows a design just like FIG. 13A, except that the encapsulated section is reduced to only the load-bearing boundary layer between the midsole 148 and the bottom sole 149. In simple terms, then, most or all of the upper surface of the bottom sole and the lower surface of the midsole are not attached, or at least not firmly attached, where they coincide at line 8. The bottom sole and midsole are firmly attached only along the non-load-bearing sides of the midsole. This approach is simple and easy. The load-bearing boundary layer 8 is like the internal horizontal sipe described in FIG. 12 above. The sipe can be a channel filled with flexible material or it can simply be a thinner chamber.

The boundary area 8 can be unglued, so that relative motion between the two surfaces is controlled only by their structural attachment together at the sides. In addition, the boundary area can be lubricated to facilitate relative motion between surfaces or lubricated by a viscous liquid that restricts motion. Or the boundary area 8 can be glued with a semi-elastic or semi-adhesive glue that controls relative motion but still permits some motion. The semi-elastic or semi-adhesive glue would then serve a shock absorption function as well.

In summary, the FIG. 13B design shows a shoe construction for a shoe, comprising: a shoe upper and a shoe sole that has a bottom portion with sides that are relatively flexible and inelastic; at least a portion of the bottom sole sides firmly attach directly to the shoe upper; a shoe upper that is composed of material that is flexible and relatively inelastic at least where the shoe upper is attached to Ed the bottom sole; the attached portions enveloping the other sole portions of the shoe sole; and the shoe sole having at least one horizontal boundary area serving as a sipe that is contained internally within the shoe sole. The FIG. 13B design can be combined with FIGS. 58–60 to include a shoe sole bottom portion composed of material reinforced with at least one fiber layer that is relatively flexible and inelastic and that is oriented in the horizontal plane.

Figure 14:
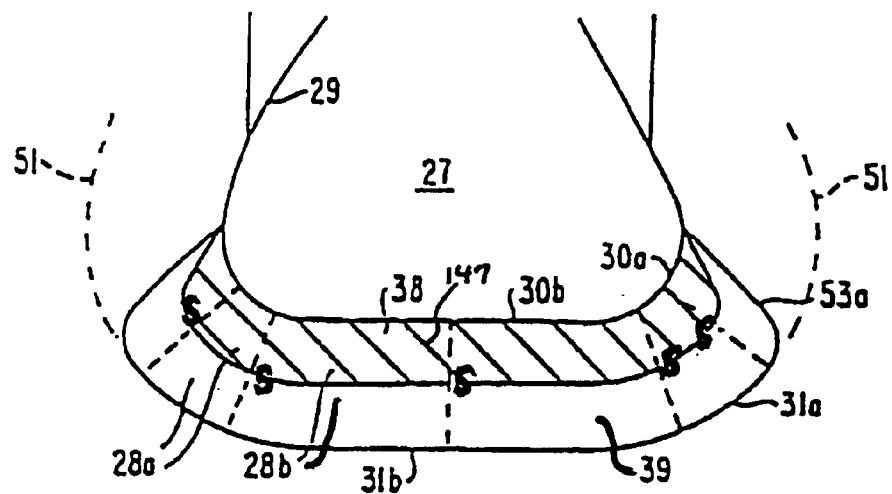
FIG. 14 shows, in frontal plane cross section at the heel portion of a shoe, a shoe sole with naturally rounded sides based on a Theoretically Ideal Stability Plane.
Figure 15:
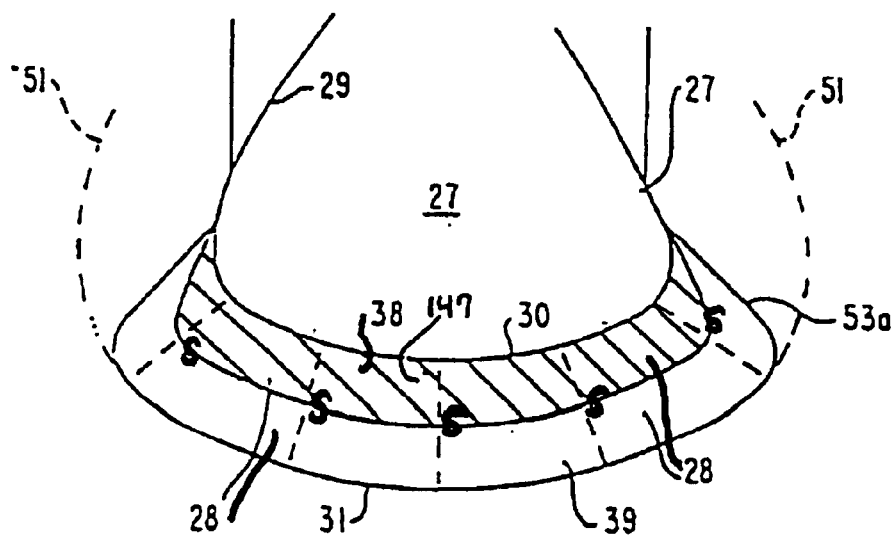
FIG. 15 shows, in frontal plane cross section, the most general case of a fully rounded shoe sole that follows the natural rounded of the bottom of the foot as well as its sides, also based on the Theoretically Ideal Stability Plane.
Figure 16A:
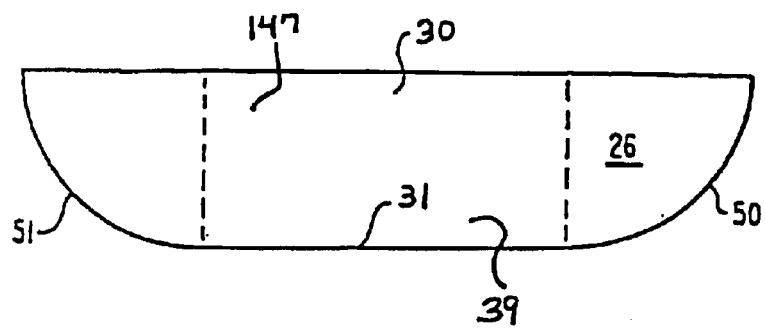
FIGS. 16A–16C show, in frontal plane cross section at the heel, a quadrant-sided shoe sole, based on a Theoretically Ideal Stability Plane.
Figure 16B:
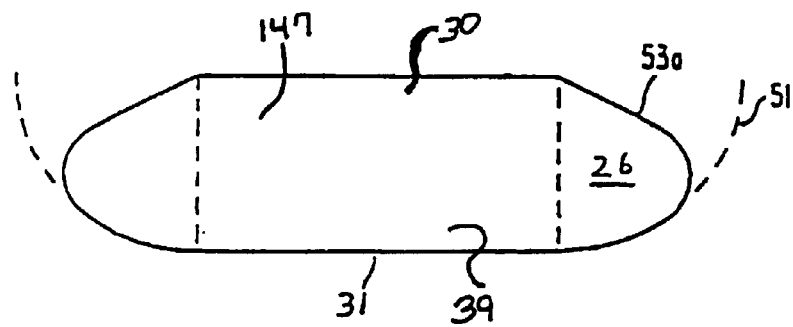
Figure 16C:
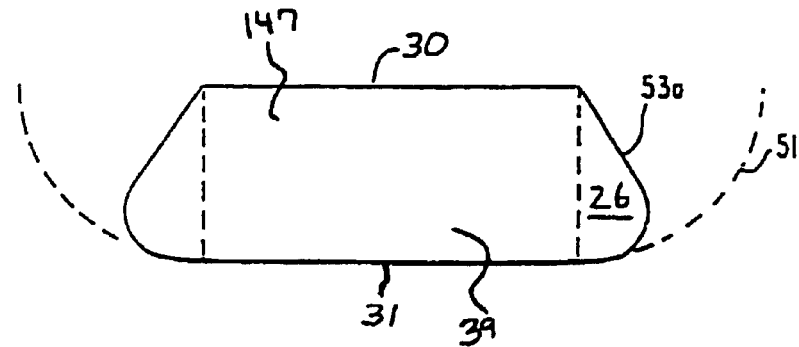
Figure 17:
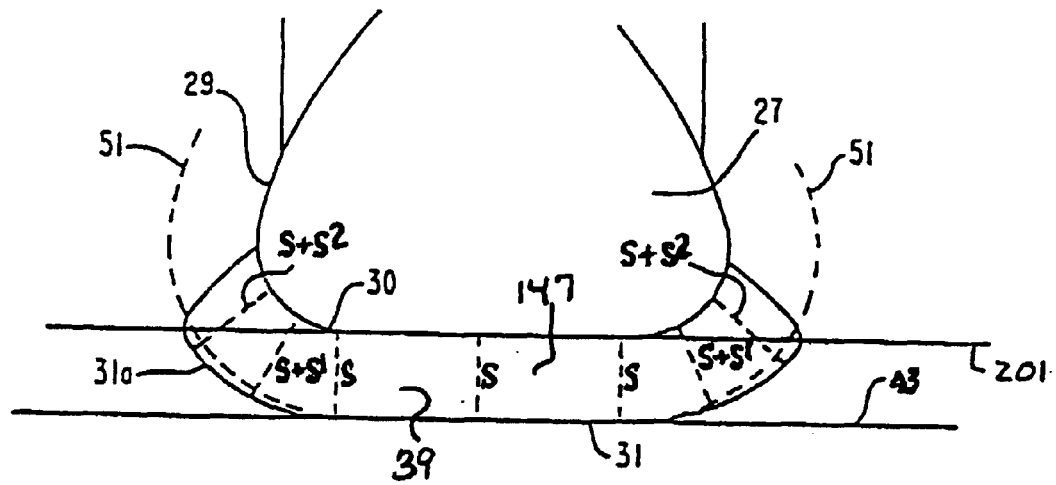
FIG. 17 shows a frontal plane cross section at the heel portion of a shoe with naturally rounded sides like those of FIG. 14, wherein a portion of the shoe sole thickness is increased beyond the Theoretically Ideal Stability Plane.

FIGS. 14, 15, and 16 show frontal plane cross sectional views of a shoe sole according to the applicant's prior inventions based on the Theoretically Ideal Stability Plane, taken at about the ankle joint to show the heel section of the shoe. FIGS. 17 through 26 show the same view of the applicant's enhancement of that invention. In the figures, a foot 27 is positioned in a naturally rounded shoe having an upper 21 and a rounded shoe sole 28. The shoe sole normally contacts the ground 43 at about the lower central heel portion thereof., as shown in FIG. 17. The concept of the Theoretically Ideal Stability Plane defines the plane 51 in terms of a locus of points determined by the thickness(es) of the sole.

FIG. 14 shows, in a rear cross sectional view, the inner surface of the shoe sole conforming to the natural rounded of the foot and the thickness of the shoe sole remaining constant in the frontal plane, so that the outer surface coincides with the Theoretically Ideal Stability Plane.

FIG. 15 shows a fully rounded shoe sole design that follows the natural rounded of all of the foot, the bottom as well as the sides, while retaining a constant shoe sole thickness in the frontal plane.

The fully rounded shoe sole assumes that the resulting slightly rounded bottom when unloaded will deform under load and flatten just as the human foot bottom is slightly rounded unloaded but flattens under load. Therefore, the shoe sole material must be of such composition as to allow the natural deformation following that of the foot. The design applies particularly to the heel, but to the rest of the shoe sole as well. By providing the closest match to the natural shape of the foot, the fully rounded design allows the foot to function as naturally as possible. Under load, FIG. 15 would deform by flattening to look essentially like FIG. 14. Seen in this light, the naturally rounded side design in FIG. 14 is a more conventional, conservative design that is a special case of the more general fully rounded design in FIG. 15, which is the closest to the natural form of the foot, but the least conventional. The amount of deformation flattening used in the FIG. 14 design, which obviously varies under different loads, is not an essential element of the applicant's invention.

FIGS. 14 and 15 both show in frontal plane cross-sections the Theoretically Ideal Stability Plane, which is also theoretically ideal for efficient natural motion of all kinds, including running, jogging or walking. FIG. 15 shows the most general case, the fully rounded design, which conforms to the natural shape of the unloaded foot. For any given individual, the Theoretically Ideal Stability Plane 51 is determined, first, by the desired shoe sole thickness(es) in a frontal plane cross section, and, second, by the natural shape of the individual's foot surface 29.

For the special case shown in FIG. 14, the Theoretically Ideal Stability Plane for any particular individual (or size average of individuals) is determined, first, by the given frontal plane cross section shoe sole thickness(es); second, by the natural shape of the individual's foot; and, third, by the frontal plane cross-section width of the individual's load-bearing footprint 30b, which is defined as the upper surface of the shoe sole that is in physical contact with and supports the human foot sole.

The Theoretically Ideal Stability Plane for the special case is composed conceptually of two parts. Shown in FIG. 14, the first part is a line segment 31b of equal length and parallel to line 30b at a constant distance(s) equal to shoe sole thickness. This corresponds to a conventional shoe sole directly underneath the human foot, and also corresponds to the flattened portion of the bottom of the load-bearing shoe sole 28b. The second part is the naturally rounded stability side outer edge 31a located at each side of the first part, line segment 31b. Each point on the rounded side outer edge 31a is located at a distance which is exactly the shoe sole thickness (s) from the closest point on the rounded side inner edge 30a.

In summary, the Theoretically Ideal Stability Plane is used to determine a geometrically precise bottom contour of the shoe sole based on a top contour that conforms to the contour of the foot.

It can be stated unequivocally that any shoe sole contour, even of similar contour, that exceeds the Theoretically Ideal Stability Plane will restrict natural foot motion, while any less than that plane will degrade natural stability, in direct proportion to the amount of the deviation. The theoretical ideal was taken to be that which is closest to natural.

FIG. 16 illustrates in frontal plane cross-section another variation of a shoe sole that uses stabilizing quadrants 26 at the outer edge of a conventional shoe sole 28b illustrated generally at the reference numeral 28. The stabilizing quadrants would be abbreviated in actual embodiments.

FIG. 17 illustrates the shoe sole side thickness increasing beyond the Theoretically Ideal Stability Plane to increase stability somewhat beyond its natural level. The unavoidable trade-off which results is that natural motion would be restricted somewhat and the weight of the shoe sole would increase somewhat.

FIG. 17 shows a situation wherein the thickness of the sole at each of the opposed sides is thicker at the portions of the sole 31a by a thickness which gradually varies continuously from a thickness (s) through a thickness (s+s1), to a thickness (s+s2). These designs recognize that lifetime use of existing shoes, the design of which has an inherent problem that continually disrupts natural human biomechanics, has produced thereby actual structural changes in a human foot and ankle to an extent that must be compensated for. Specifically, one of the most common of the abnormal effects of the inherent existing problem is a weakening of the long arch of the foot, increasing pronation. These designs therefore provide greater than natural stability and should be particularly useful to individuals, generally with low arches, prone to pronate excessively, and could be used only on the medial side. Similarly, individuals with high arches and a tendency to over supinate and who are vulnerable to lateral ankle sprains would also benefit, and the design could be used only on the lateral side. A shoe for the general population that compensates for both weaknesses in the same shoe would incorporate the enhanced stability of the design compensation on both sides.

FIG. 17, like FIGS. 14 and 15, shows an embodiment which allows the shoe sole to deform naturally, closely paralleling the natural deformation of the bare foot under load. In addition, shoe sole material must be of such composition as to allow natural deformation similar to that of the foot.

This design retains the concept of contouring the shape of the shoe sole to the shape of the human foot. The difference is that the shoe sole thickness in the frontal plane is allowed to vary rather than remain uniformly constant. More specifically, FIGS. 17, 18, 19, 20, and 24 show, in frontal plane cross sections at the heel, that the shoe sole thickness can increase beyond the Theoretically Ideal Stability Plane 51, in order to provide greater than natural stability. Such variations (and the following variations) can be consistent through all frontal plane cross sections, so that there are proportionately equal increases to the Theoretically Ideal Stability Plane 51 from the front of the shoe sole to the back. Alternatively, the thickness can vary, preferably continuously, from one frontal plane to the next.

The exact amount of the increase in shoe sole thickness beyond the Theoretically Ideal Stability Plane is to be determined empirically. Ideally, right and left shoe soles would be custom designed for each individual based on a biomechanical analysis of the extent of his or her foot and ankle dysfunction in order to provide an optimal individual correction. If epidemiological studies indicate general corrective patterns for specific categories of individuals or the population as a whole, then mass-produced corrective shoes with soles incorporating rounded sides having a thickness exceeding the Theoretically Ideal Stability Plane would be possible. It is expected that any such mass-produced corrective shoes for the general population would have thicknesses exceeding the Theoretically Ideal Stability Plane by an amount up to 5 or 10 percent, while more specific groups or individuals with more severe dysfunction could have an empirically demonstrated need for greater corrective thicknesses on the order of up to 25 percent more than the Theoretically Ideal Stability Plane. The optimal rounded for the increased thickness may also be determined empirically.

Figure 18:
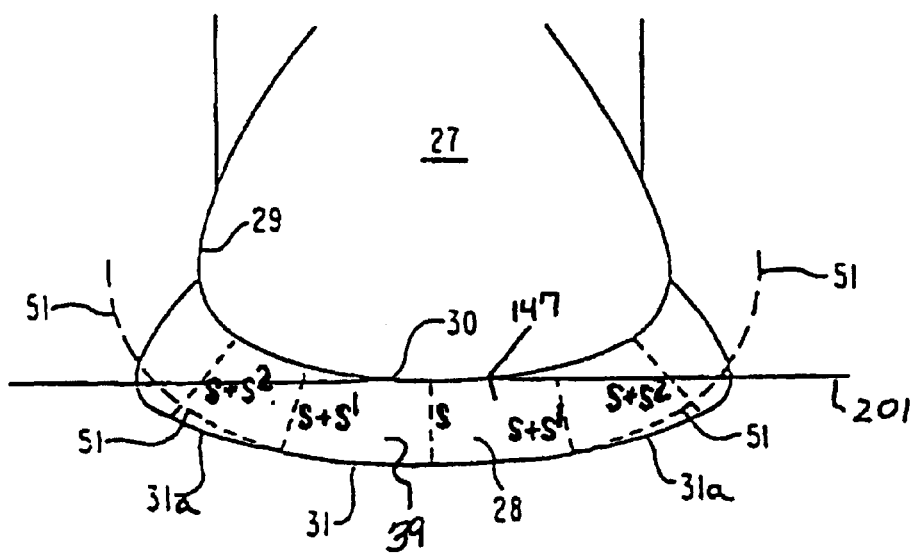
FIG. 18 is a view similar to FIG. 17, but of a shoe with fully rounded sides wherein the sole thickness increases with increasing distance from the center line of the ground-contacting portion of the sole.

FIG. 18 shows a variation of the enhanced fully rounded design wherein the shoe sole begins to thicken beyond the Theoretically Ideal Stability Plane 51 somewhat offset to the sides.

Figure 19:
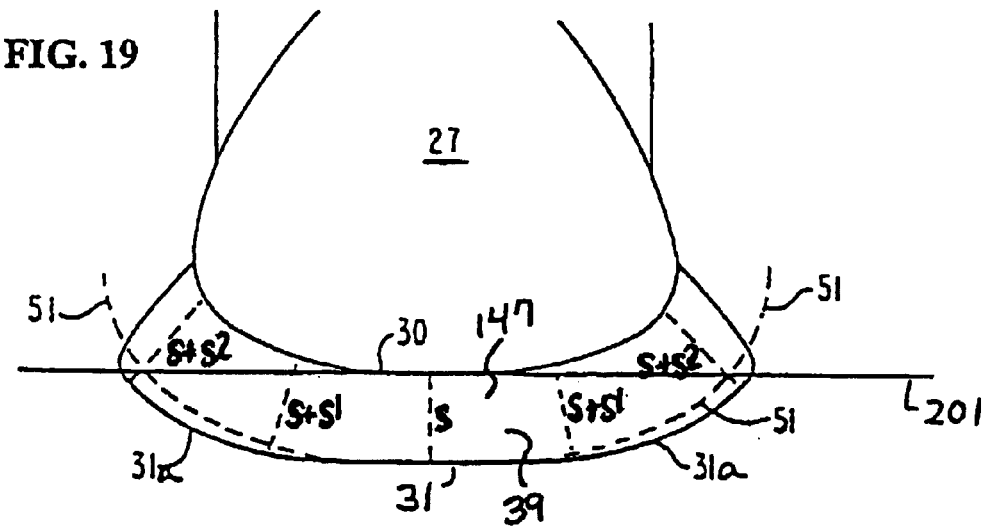
FIG. 19 is a view similar to FIG. 18 where the fully rounded sole thickness variations are continually increasing on each side.

FIG. 19 shows a thickness variation which is symmetrical as in the case of FIG. 17 and 18, but wherein the shoe sole begins to thicken beyond the Theoretically Ideal Stability Plane 51 directly underneath the foot heel 27 on about a center line of the shoe sole. In fact, in this case the thickness of the shoe sole is the same as the Theoretically Ideal Stability Plane only at that beginning point underneath the upright foot. For the embodiment wherein the shoe sole thickness varies, the Theoretically Ideal Stability Plane is determined by the least thickness in the shoe sole's direct load-bearing portion meaning that portion with direct tread contact on the ground. The outer edge or periphery of the shoe sole is obviously excluded, since the thickness there always decreases to zero. Note that the capability of the design to deform naturally may make some portions of the shoe sole load-bearing when they are actually under a load, especially walking or running, even though they may not be when the shoe sole is not under a load.

Figure 20:
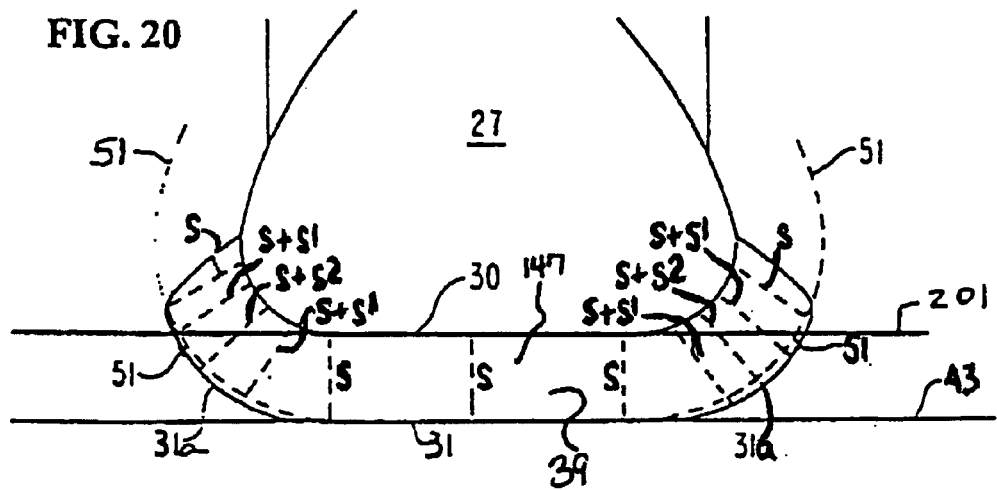
FIG. 20 is a view similar to FIGS. 17–19 wherein the sole thickness varies in diverse sequences.

FIG. 20 shows that the thickness can also increase and then decrease. Other thickness variation sequences are also possible. The variation in side rounded thickness can be either symmetrical on both sides or asymmetrical, particularly with the medial side providing more stability than the lateral side, although many other asymmetrical variations are possible. Also, the pattern of the right foot can vary from that of the left foot.

FIGS. 21, 22, 23 and 25 show that similar variations in shoe midsole (other portions of the shoe sole area not shown) density can provide similar, but reduced, effects to the variations in shoe sole thickness described previously in FIGS. 17–20. The major advantage of this approach is that the structural Theoretically Ideal Stability Plane is retained, so that naturally optimal stability and efficient motion are retained to the maximum extent possible.

Figure 21:
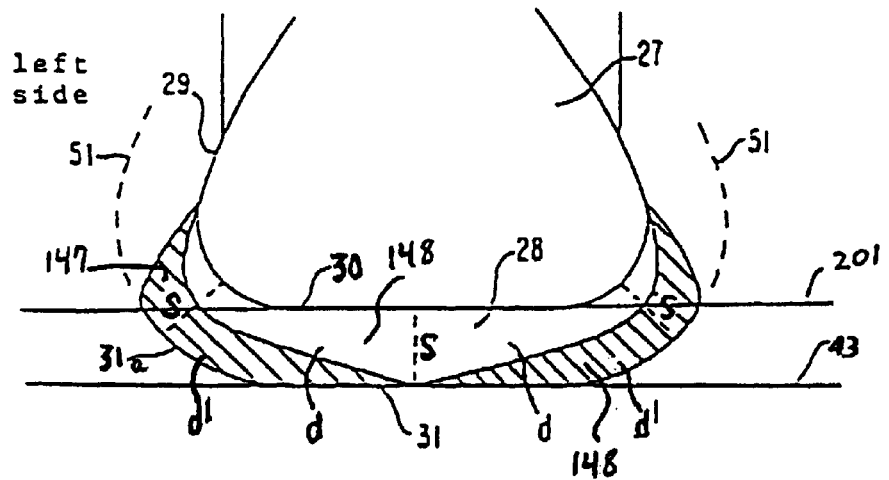
FIG. 21 is a frontal plane cross section showing a density variation in the midsole.
Figure 22:
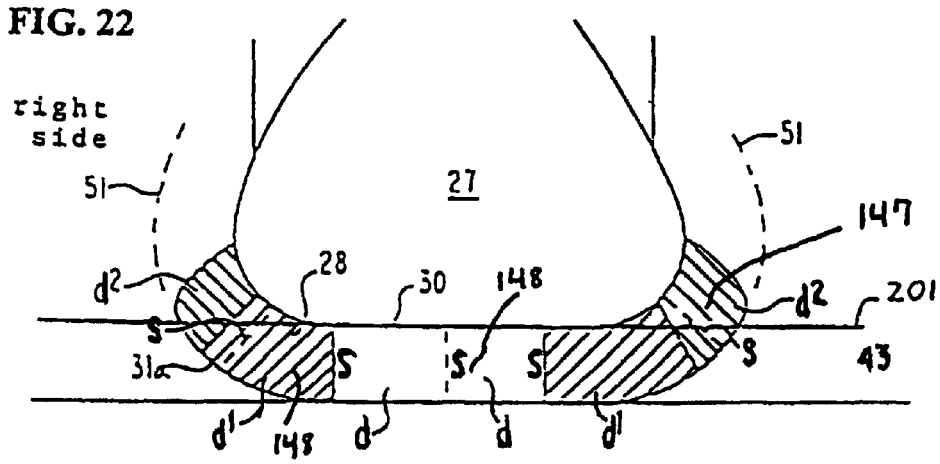
FIG. 22 is a view similar to FIG. 21 wherein the firmest density material is at the outermost edge of the midsole rounded.

The forms of dual and tri-density midsoles shown in the figures are extremely common in the current art of athletic shoes, and any number of densities are theoretically possible, although an angled alternation of just two densities like that shown in FIG. 21 provides continually changing composite density. However, multi-densities in the midsole were not preferred since only a uniform density provides a neutral shoe sole design that does not interfere with natural foot and ankle biomechanics in the way that multi-density shoe soles do, which is by providing different amounts of support to different parts of the foot. In these figures, the density of the sole material designated by the legend ($d^1$) is firmer than (d) while ($d^2$) is the firmest of the three representative densities shown. In FIG. 21, a dual density sole is shown, with (d) having the less firm density.

It should be noted that shoe soles using a combination both of sole thicknesses greater than the Theoretically Ideal Stability Plane and of midsole density variations like those just described are also possible but not shown.

Figure 23:
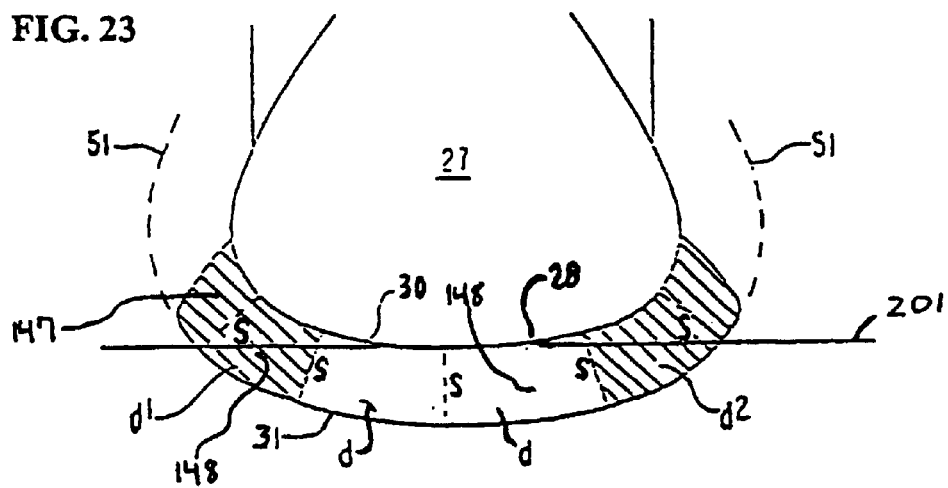
FIG. 23 is a view similar to FIGS. 21 and 22 showing still another density variation, one which is asymmetrical.
Figure 24:
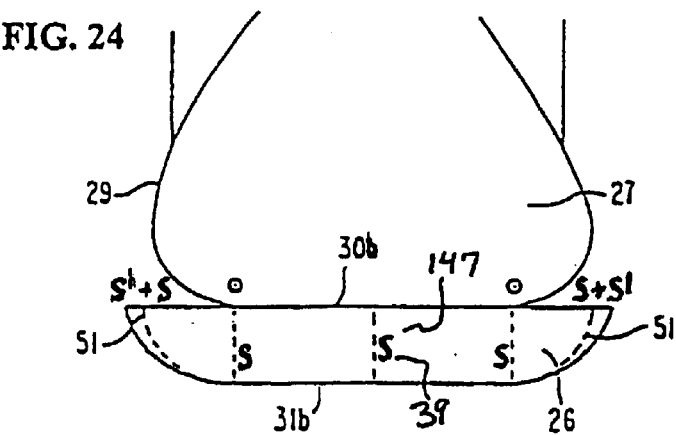
FIG. 24 shows a variation in the thickness of the sole for the quadrant-sided shoe sole embodiment of FIGS. 16A–16C which is greater than a Theoretically Ideal Stability Plane.
Figure 25:
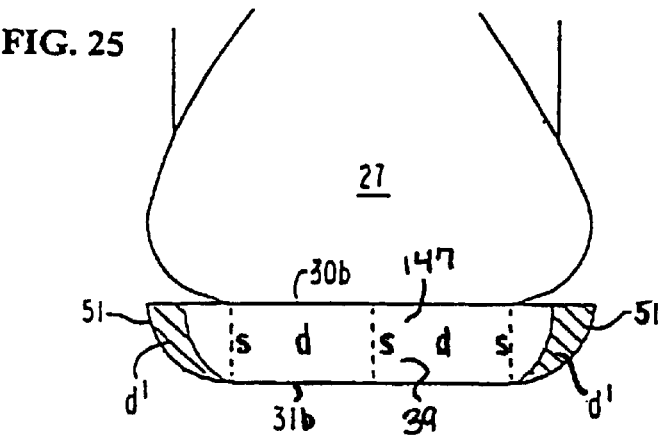
FIG. 25 shows a quadrant-sided embodiment as in FIG. 24 wherein the density of the sole varies.
Figure 26:
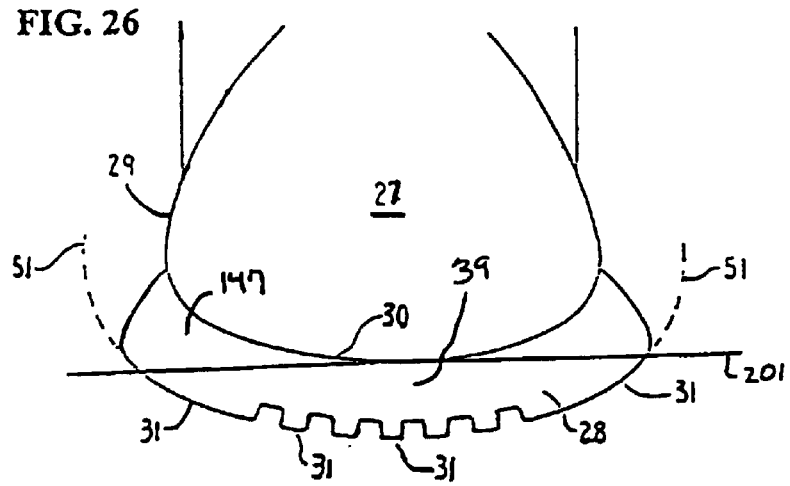
FIG. 26 shows a bottom sole tread design that provides a similar density variation to that shown in FIG. 23.

FIG. 26 shows a bottom sole tread design that provides about the same overall shoe sole density variation as that provided in FIG. 23 by midsole density variation. The less supporting tread there is under any particular portion of the shoe sole, the less effective overall shoe sole density there is, since the midsole above that portion will deform more easily than if it were fully supported.

FIG. 27 shows embodiments like those in FIGS. 17 through 26 but wherein a portion of the shoe sole thickness is decreased to less than the Theoretically Ideal Stability Plane. It is anticipated that some individuals with foot and ankle biomechanics that have been degraded by existing shoes may benefit from such embodiments, which would provide less than natural stability but greater freedom of motion, and less shoe sole weight and bulk. In particular, it is anticipated that individuals with overly rigid feet, those with restricted range of motion, and those tending to oversupinate may benefit from the FIG. 14 embodiments. Even more particularly, it is expected that the invention will benefit individuals with significant bilateral foot function asymmetry: namely, a tendency toward pronation on one foot and supination on the other foot. Consequently, it is anticipated that this embodiment would be used only on the shoe sole of the supinating foot, and on the inside portion only, possibly only a portion thereof. It is expected that the range less than the Theoretically Ideal Stability Plane would be a maximum of about five to ten percent, though a maximum of up to twenty-five percent may be beneficial to some individuals.

Figure 27A:
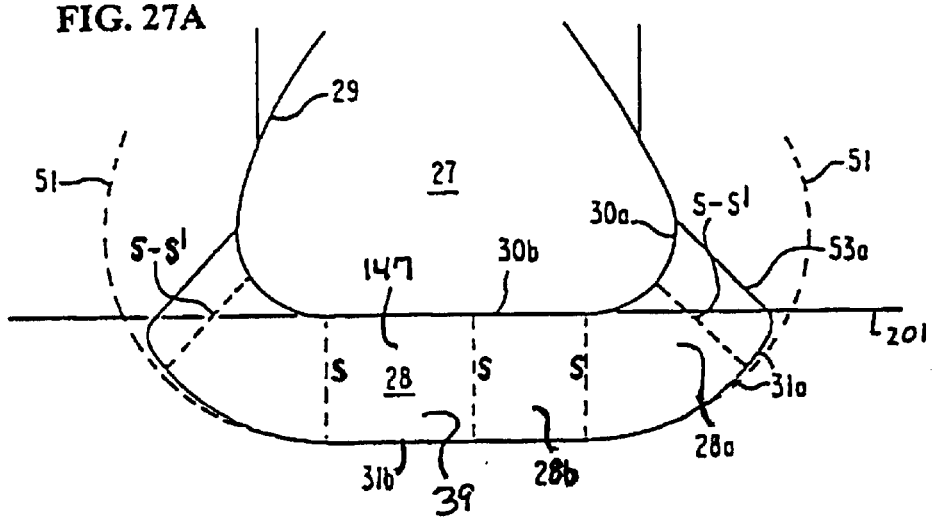
FIG. 27 shows embodiments similar to those shown in FIGS. 14–16, but wherein a portion of the shoe sole thickness is decreased to less than the Theoretically Ideal Stability Plane.
Figure 27B:
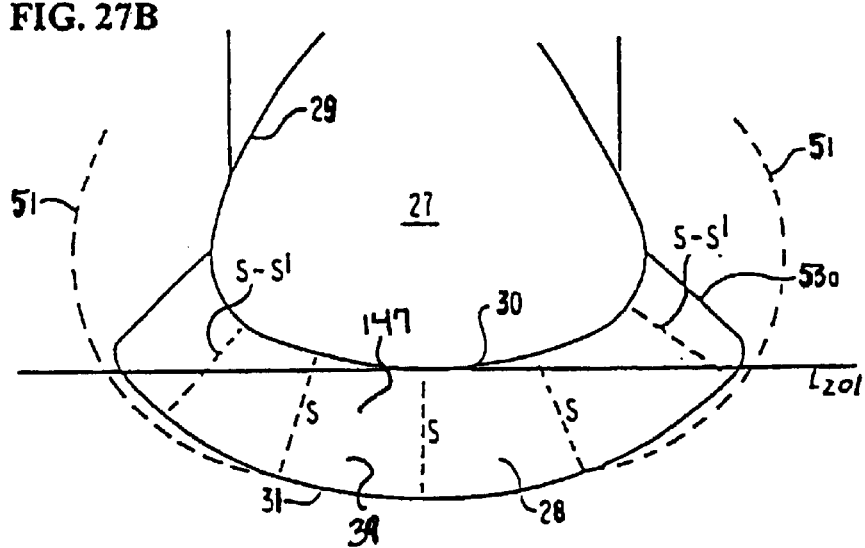
Figure 27C:
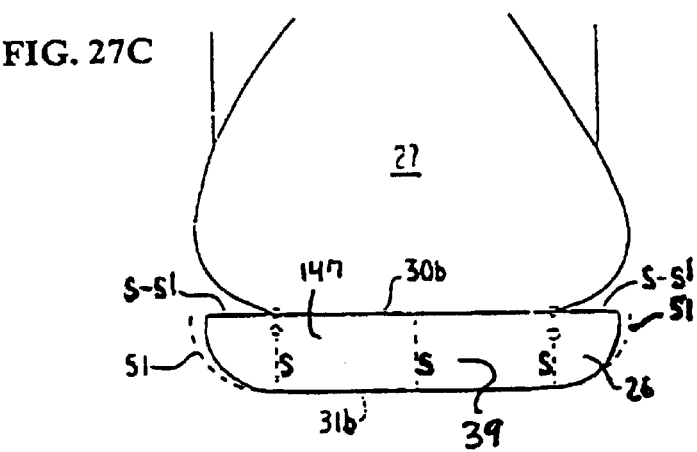

FIG. 27A shows an embodiment like FIGS. 17 and 20, but with naturally rounded sides less than the Theoretically Ideal Stability Plane. FIG. 27B shows an embodiment like the fully rounded design in FIGS. 18 and 19, but with a shoe sole thickness decreasing with increasing distance from the center portion of the sole. FIG. 27C shows an embodiment like the quadrant-sided design of FIG. 24, but with the quadrant sides increasingly reduced from the Theoretically Ideal Stability Plane.

The lesser-sided design of FIG. 27 would also apply to the FIGS. 21–23 and 25 density variation approach and to the FIG. 26 approach using tread design to approximate density variation.

Figure 28A:
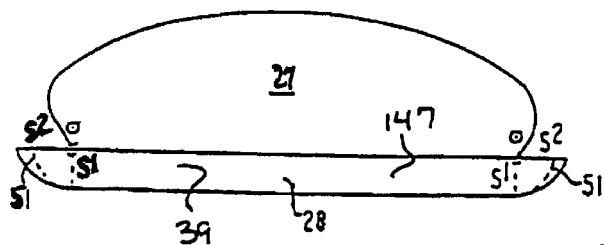
FIG. 28 shows embodiments of the invention with shoe sole sides having thicknesses both greater and lesser than the Theoretically Ideal Stability Plane.
Figure 28B:
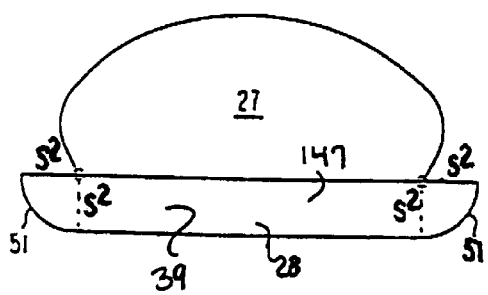
Figure 28C:
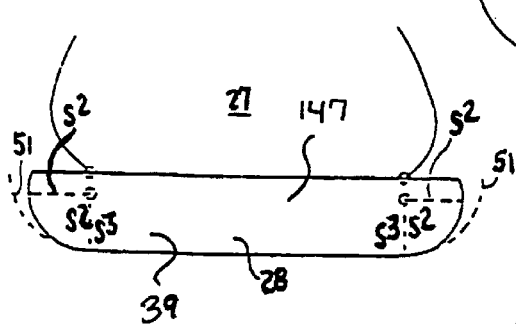

FIG. 28A–28C show, in cross-sections that with the quadrant-sided design of FIGS. 16, 24, 25 and 27C that it is possible to have shoe sole sides that are both greater and lesser than the Theoretically Ideal Stability Plane in the same shoe. The radius of an intermediate shoe sole thickness, taken at ($s^2$) at the base of the fifth metatarsal in FIG. 28B, is maintained constant throughout the quadrant sides of the shoe sole, including both the heel, FIG. 28C, and the forefoot, FIG. 28A, so that the side thickness is less than the Theoretically Ideal Stability Plane at the heel and more at the forefoot. Though possible, this is not a preferred approach.

Figure 28D:
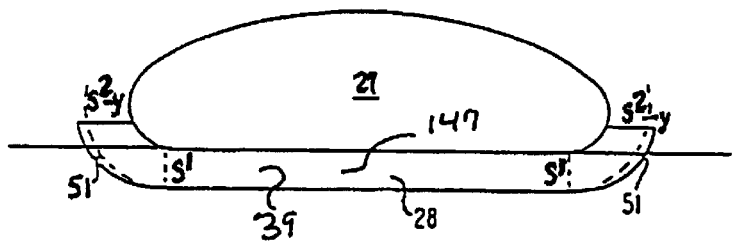
Figure 28E:
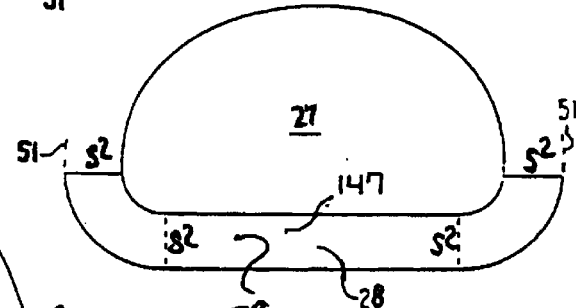
Figure 28F:
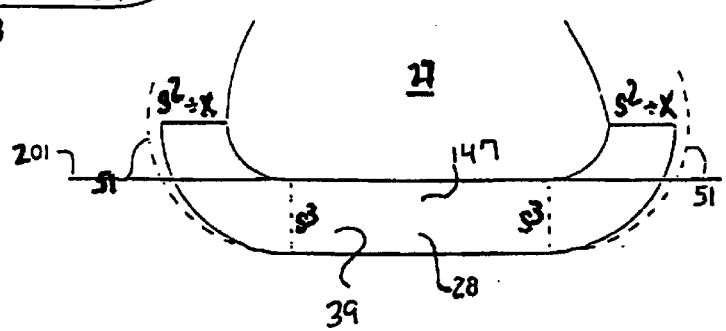

The same approach can be applied to the naturally rounded sides or fully to rounded designs described in FIGS. 14, 15, 17–23 and 26, but it is also not preferred. In addition, as shown in FIGS. 28D–28F, it is possible to have shoe sole sides that are both greater and lesser than the Theoretically Ideal Stability Plane in the same shoe, like FIGS. 28A–28C, but wherein the side thickness (or radius) is neither constant like FIGS. 28A–28C or varying directly with shoe sole thickness, but instead varying quite indirectly with shoe sole thickness. As shown in FIGS. 28D–28F, the shoe sole side thickness varies from somewhat less than the shoe sole thickness at the heel to somewhat more at the forefoot. This approach, though possible, is again not preferred, and can be applied to the quadrant sided design, but is not preferred there either.

FIG. 29 shows in a frontal plane cross-section at the heel (center of ankle joint) the general concept of a shoe sole 28 that conforms to the natural shape of the human foot 27 and that has a constant thickness (s) in frontal plane cross sections. The surface 29 of the bottom and sides of the foot 27 should correspond exactly to the upper surface 30 of the shoe sole 28. The shoe sole thickness is defined as the shortest distance (s) between any point on the upper surface 30 of the shoe sole 28 and the lower surface 31. In effect, the applicant's general concept is a shoe sole 28 that wraps around and conforms to the natural contours of the foot 27 as if the shoe sole 28 were made of a theoretical single flat sheet of shoe sole material of uniform thickness, wrapped around the foot with no distortion or deformation of that sheet as it is bent to the foot's contours. To overcome real world deformation problems associated with such bending or wrapping around contours, actual construction of the shoe sole contours of uniform thickness will preferably involve the use of multiple sheet lamination or injection molding techniques.

FIGS. 30A, 30B, and 30C illustrate in frontal plane cross-section use of naturally rounded stabilizing sides 28a at the outer edge of a shoe sole 28b illustrated generally at the reference numeral 28. This eliminates the unnatural sharp bottom edge, especially of flared shoes, in favor of a naturally rounded shoe sole outside 31 as shown in FIG. 29. The side or inner edge 30a of the shoe sole stability side 28a is rounded like the natural form on the side or edge of the human foot, as is the outside or outer edge 31a of the shoe sole stability side 28a to follow a Theoretically Ideal Stability Plane. The thickness (s) of the shoe sole 28 is maintained exactly constant, even if the shoe sole is tilted to either side, or forward or backward. Thus, the naturally rounded stabilizing sides 28a, are defined as the same as the thickness 33 of the shoe sole 28 so that, in cross-section, the shoe sole comprises a stable shoe sole 28 having at its outer edge naturally rounded stabilizing sides 28a with a surface 31a representing a portion of a Theoretically Ideal Stability Plane and described by naturally rounded sides equal to the thickness (s) of the sole 28. The top of the shoe sole 30b coincides with the shoe wearer's load-bearing footprint, since in the case shown the shape of the foot is assumed to be load-bearing and therefore flat along the bottom. A top edge 32 of the naturally rounded stability side 28a can be located at any point along the rounded side of the outer surface of the foot 29, while the inner edge 33 of the naturally rounded side 28a coincides with the perpendicular sides 34 of the load-bearing shoe sole 28b. In practice, the shoe sole 28 is preferably integrally formed from the portions 28b and 28a. Thus, the Theoretically Ideal Stability Plane includes the contours 31 a merging into the lower surface 31b of the rounded shoe sole 28.

Preferably, the peripheral extent 36 of the load-bearing portion of the sole 28b of the shoe includes all of the support structures of the foot but extends no further than the outer edge of the foot sole 37 as defined by a load-bearing footprint, as shown in FIG. 30D, which is a top view of the upper shoe sole surface 30b. FIG. 30D thus illustrates a foot outline at numeral 37 and a recommended sole outline 36 relative thereto. Thus, a horizontal plane outline of the top of the load-bearing portion of the shoe sole, therefore exclusive of rounded stability sides, should, preferably, coincide as nearly as practicable with the load-bearing portion of the foot sole with which it comes into contact. Such a horizontal outline, as best seen in FIGS. 30D and 33D, should remain uniform throughout the entire thickness of the shoe sole eliminating negative or positive sole flare so that the sides are exactly perpendicular to the horizontal plane as shown in FIG. 30B. Preferably, the density of the shoe sole material is uniform.

As shown diagrammatically in FIG. 31, preferably, as the heel lift or wedge 38 of thickness (s1) increases the total thickness (s+s1) of the combined midsole and outer sole 39 of thickness (s) in an aft direction of the shoe, the naturally rounded sides 28a increase in thickness exactly the same amount according to the principles discussed in connection with FIG. 30. Thus, the thickness of the inner edge 33 of the naturally rounded side is always equal to the constant thickness (s) of the load-bearing shoe sole 28b in the frontal cross-sectional plane.

As shown in FIG. 31B, for a shoe that follows a more conventional horizontal plane outline, the sole can be improved significantly by the addition of a naturally rounded side 28a which correspondingly varies with the thickness of the shoe sole and changes in the frontal plane according to the shoe heel lift 38. Thus, as illustrated in FIG. 31B, the thickness of the naturally rounded side 28a in the heel section is equal to the thickness (s+s1) of the shoe sole 28 which is thicker than the shoe sole 39 thickness (s) shown in FIG. 31A by an amount equivalent to the heel lift 38 thickness (s1). In the generalized case, the thickness (s) of the rounded side is thus always equal to the thickness (s) of the shoe sole.

FIG. 32 illustrates a side cross-sectional view of a shoe to which the invention has been applied and is also shown in a top plane view in FIG. 33.

Thus, FIGS. 33A, 33B, and 33C represent frontal plane cross-sections taken along the forefoot, at the base of the fifth metatarsal, and at the heel, thus illustrating that the shoe sole thickness is constant at each frontal plane cross-section, even though that thickness varies from front to back, due to the heel lift 38 as shown in FIG. 32, and that the thickness of the naturally rounded sides is equal to the shoe sole thickness in each FIG. 33A–33C cross section. Moreover, in FIG. 33D, a horizontal plane overview of the left foot, it can be seen that the rounded of the sole follows the preferred principle in matching, as nearly as practical, the load-bearing sole print shown in FIG. 30D.

FIG. 34 illustrates an embodiment of the invention which utilizes varying portions of the Theoretically Ideal Stability Plane 51 in the naturally rounded sides 28a in order to reduce the weight and bulk of the sole, while accepting a sacrifice in some stability of the shoe. Thus, FIG. 34A illustrates the preferred embodiment as described above in connection with FIG. 31 wherein the outer edge 31a of the naturally rounded sides 28a follows a Theoretically Ideal Stability Plane 51. As in FIGS. 29 and 30, the rounded surfaces 31a, and the lower surface of the sole 31b lie along the Theoretically Ideal Stability Plane 51. As shown in FIG. 34B, an engineering trade-off results in an abbreviation within the Theoretically Ideal Stability Plane 51 by forming a naturally rounded side surface 53a approximating the natural rounded of the foot (or more geometrically regular, which is less preferred) at an angle relative to the upper plane of the shoe sole 28 so that only a smaller portion of the rounded side 28a defined by the constant thickness lying along the surface 31a is coplanar with the Theoretically Ideal Stability Plane 51. FIGS. 34C and 34C show similar embodiments wherein each engineering trade-off shown results in progressively smaller portions of rounded side 28a, which lies along the Theoretically Ideal Stability Plane 51. The portion of the surface 31a merges into the upper side surface 53a of the naturally rounded side 28a.

The embodiment of FIG. 34 may be desirable for portions of the shoe sole which are less frequently used so that the additional part of the side is used less frequently. For example, a shoe may typically roll out laterally, in an inversion mode, to about 20° on the order of 100 times for each single time it rolls out to 40°. For a basketball shoe, shown in FIG. 34B, the extra stability is needed. Yet, the added shoe weight to cover that infrequently experienced range of motion is about equivalent to covering the frequently encounter range. Since in a racing shoe this weight might not be desirable, an engineering trade-off of the type shown in FIG. 34D is possible. A typical athletic/jogging shoe is shown in FIG. 34C. The range of possible variations is limitless.

FIG. 35 shows the Theoretically Ideal Stability Plane 51 in defining embodiments of the shoe sole having differing tread or cleat patterns. Thus, FIG. 35 illustrates that the invention is applicable to shoe soles having conventional bottom treads. Accordingly, FIG. 35A is similar to FIG. 34B further including a tread portion 60, while FIG. 35B is also similar to FIG. 34B wherein the sole includes a cleated portion 61. The surface 63 to which the cleat bases are affixed should preferably be on the same plane and parallel the Theoretically Ideal Stability Plane 51, since in soft ground that surface rather than the cleats become load-bearing. The embodiment in FIG. 35C is similar to FIG. 34C showing still an alternative tread construction 62. In each case, the load-bearing outer surface of the tread or cleat pattern 60–62 lies along the Theoretically Ideal Stability Plane 51.

Figure 36:
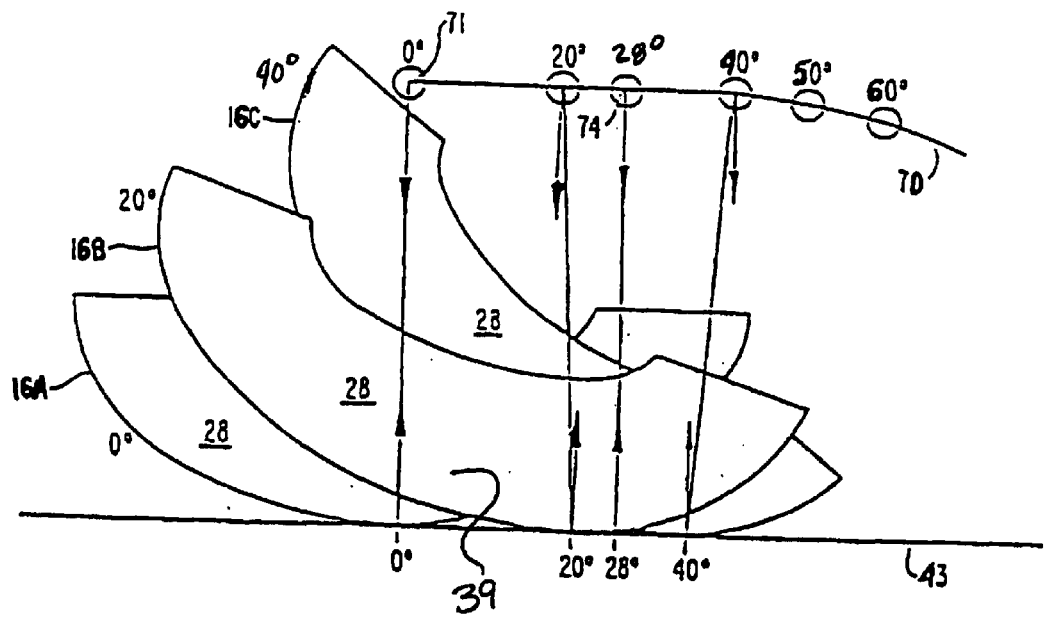
FIG. 36 is a diagrammatic frontal plane cross-sectional view of static forces acting on the ankle joint and its position relative to a shoe sole according to the invention during normal and extreme inversion and eversion motion.

FIG. 36 illustrates in a curve 70 the range of side to side inversion/eversion motion of the ankle center of gravity 71 from the shoe shown in frontal plane cross-section at the ankle. Thus, in a static case where the center of gravity 71 lies at approximately the mid-point of the sole, and assuming that the shoe inverts or everts from 0° to 200 to 40°, as shown in progressions 36A, 36B and 36C, the locus of points of motion for the center of gravity thus defines the curve 70 wherein the center of gravity 71 maintains a steady level motion with no vertical component through 40° of inversion or eversion. For the embodiment shown, the shoe sole stability equilibrium point is at 28° (at point 74) and in no case is there a pivoting edge to define a rotation point. The inherently superior side to side stability of the design provides pronation control (or eversion), as well as lateral (or inversion) control. In marked contrast to conventional shoe sole designs, this shoe design creates virtually no abnormal torque to resist natural inversion/eversion motion or to destabilize the ankle joint.

Figure 37:
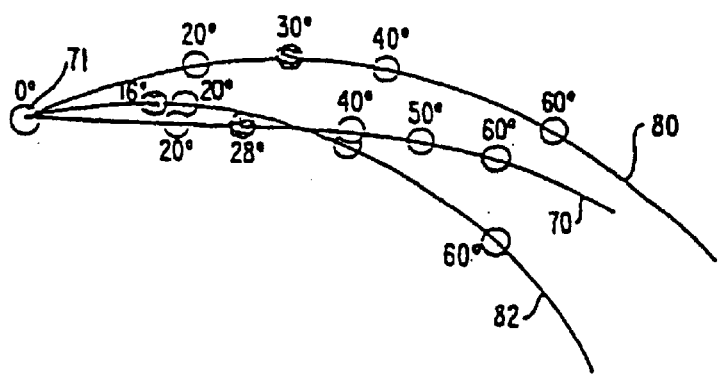
FIG. 37 is a diagrammatic frontal plane view of a plurality of moment curves of the center of gravity for various degrees of inversion for a shoe sole according to the invention contrasted with comparable motions of conventional shoes.

FIG. 37 thus compares the range of motion of the center of gravity for the invention, as shown in curve 70, in comparison to curve 80 for the conventional wide heel flare and a curve 82 for a narrow rectangle the width of a human heel. Since the shoe stability limit is 28° in the inverted mode, the shoe sole is stable at the 20° approximate bare foot inversion limit. That factor, and the broad base of support rather than the sharp bottom edge of the prior art, make the rounded design stable even in the most extreme case as shown in FIGS. 36A–36C and permit the inherent stability of the bare foot to dominate without interference, unlike existing designs, by providing constant, unvarying shoe sole thickness in frontal plane cross sections. The stability superiority of the rounded side design is thus clear when observing how much flatter its center of gravity curve 70 is than in existing popular wide flare design 80. The curve demonstrates that the rounded side design has significantly more efficient natural 7° inversion/eversion motion than the narrow rectangle design the width of a human heel, and very much more efficient than the conventional wide flare design. At the same time, the rounded side design is more stable in extremis than either conventional design because of the absence of destabilizing torque.

Figure 38A:
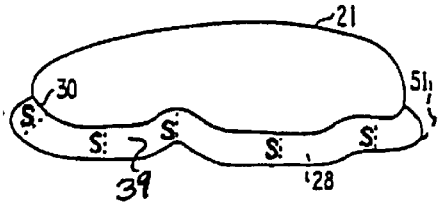
FIG. 38 shows a design with naturally rounded sides extended to other structural contours underneath the load-bearing foot such as the main longitudinal arch.
Figure 38B:
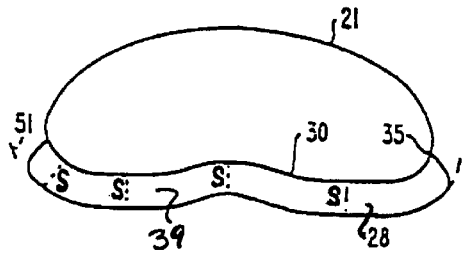
Figure 38C:
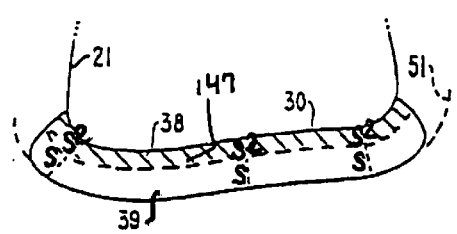
Figure 38D:
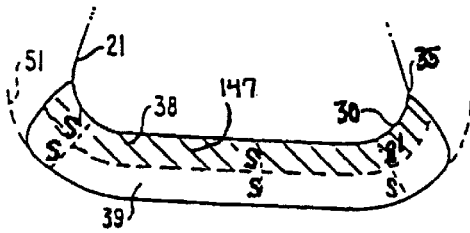
Figure 38:
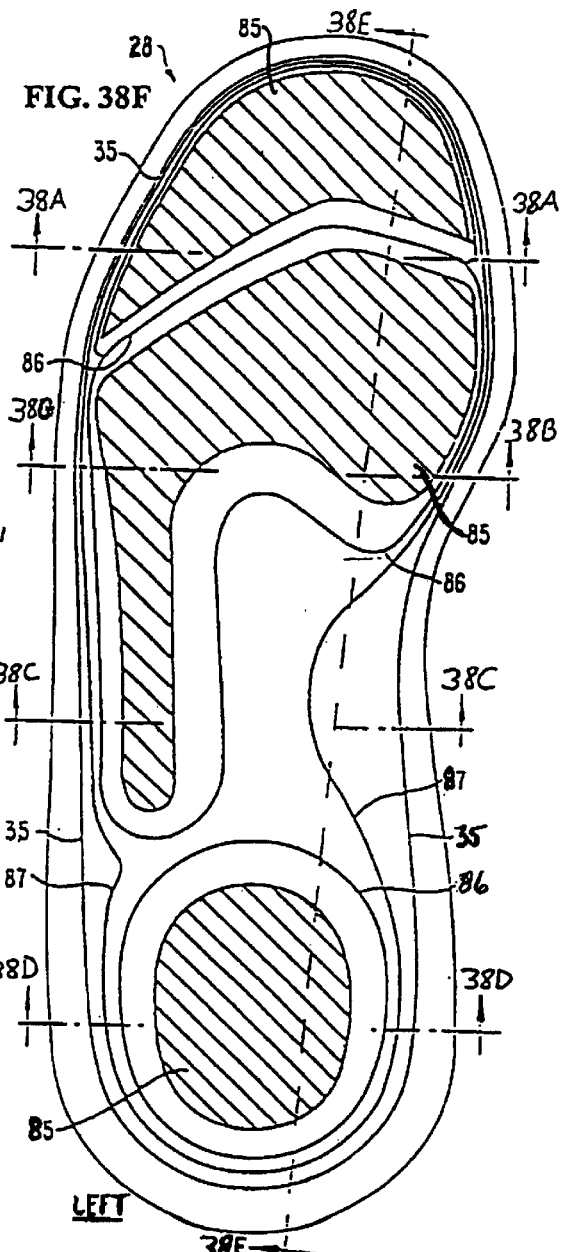
Figure 38E:
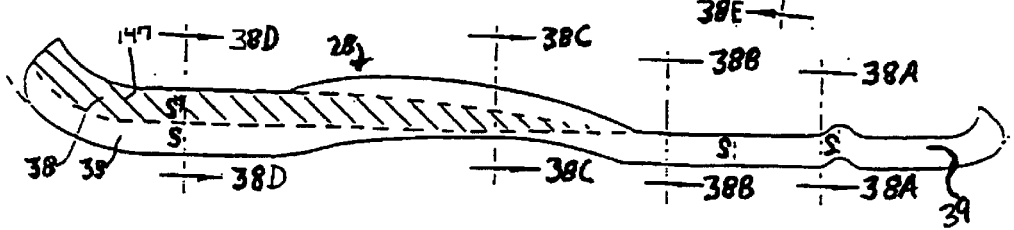

FIGS. 38A–38D illustrate, in frontal plane cross sections, the naturally rounded sides design extended to the other natural contours underneath the load-bearing foot, such as the main longitudinal arch, the metatarsal (or forefoot) arch, and the ridge between the heads of the metatarsals (forefoot) and the heads of the distal phalanges (toes). As shown, the shoe sole thickness remains constant as the rounded of the shoe sole follows that of the sides and bottom of the load-bearing foot. FIG. 38E shows a sagittal plane cross section of the shoe sole conforming to the rounded of the bottom of the load-bearing foot, with thickness varying according to the heel lift 38. FIG. 38F shows a horizontal plane top view of the left foot that shows the areas 85 of the shoe sole that correspond to the flattened portions of the foot sole that are in contact with the ground when load-bearing. Rounded lines 86 and 87 show approximately the relative height of the shoe sole contours above the flattened load-bearing areas 85 but within roughly the peripheral extent 35 of the upper surface of sole 30 shown in FIG. 30. A horizontal plane bottom view (not shown) of FIG. 38F would be the exact reciprocal or converse of FIG. 38F (i.e. peaks and valleys contours would be exactly reversed).

FIGS. 39A–39D show, in frontal plane cross sections, the fully rounded shoe sole design extended to the bottom of the entire non-load-bearing foot. FIG. 39E shows a sagittal plane cross section. The shoe sole contours underneath the foot are the same as FIGS. 38A–38E except that there are no flattened areas corresponding to the flattened areas of the load-bearing foot. The exclusively rounded contours of the shoe sole follow those of the unloaded foot. A heel lift 38 and a midsole and outersole 39, the same as that of FIG. 38, is incorporated in this embodiment, but is not shown in FIG. 39.

FIG. 40 shows the horizontal plane top view of the left foot corresponding to the fully rounded design described in FIGS. 39A–39E, but abbreviated along the sides to only essential structural support and propulsion elements. Shoe sole material density can be increased in the unabbreviated essential elements to compensate for increased pressure loading there. The essential structural support elements are the base and lateral tuberosity of the calcaneus 95, the heads of the metatarsals 96, and the base of the fifth metatarsal 97. They must be supported both underneath and to the outside for stability. The essential propulsion element is the head of first distal phalange 98. The medial (inside) and lateral (outside) sides supporting the base of the calcaneus are shown in FIG. 40 oriented roughly along either side of the horizontal plane subtalar ankle joint axis, but can be located also more conventionally along the longitudinal axis of the shoe sole. FIG. 40 shows that the naturally rounded stability sides need not be used except in the identified essential areas. Weight savings and flexibility improvements can be made by omitting the non-essential stability sides. Round lines 85 through 89 show approximately the relative height of the shoe sole contours within roughly the peripheral extent 35 of the underformed upper surface of shoe 30 shown in FIG. 17. A horizontal plane bottom view (not shown) of FIG. 40 would be the exact reciprocal or converse of FIG. 40 (i.e. peak and valley contours would be exactly reversed).

FIG. 41A shows a development of street shoes with naturally rounded sole sides incorporating features according to the present invention. FIG. 41A develops a Theoretically Ideal Stability Plane 51, as described above, for such a street shoe, wherein the thickness of the naturally rounded sides equals the shoe sole thickness. The resulting street shoe with a correctly rounded sole is thus shown in frontal plane heel cross section in FIG. 41A, with side edges perpendicular to the ground, as is typical. FIG. 41B shows a similar street shoe with a fully rounded design, including the bottom of the sole. Accordingly, the invention can be applied to an unconventional heel lift shoe, like a simple wedge, or to the most conventional design of a typical walking shoe with its heel separated from the forefoot by a hollow under the instep. The invention can be applied just at the shoe heel or to the entire shoe sole. With the invention, as so applied, the stability and natural motion of any existing shoe design, except high heels or spike heels, can be significantly improved by the naturally rounded shoe sole design.

FIG. 42 shows a non-optimal but interim or low cost approach to shoe sole construction, whereby the midsole 148 and heel lift 38 are produced conventionally, or nearly so (at least leaving the midsole bottom surface flat, though the sides can be rounded), while the bottom or outer sole 149 includes most or all of the special contours of the design. Not only would that completely or mostly limit the special contours to the bottom sole, which would be molded specially, it would also ease assembly, since two flat surfaces of the bottom of the midsole and the top of the bottom sole could be mated together with less difficulty than two rounded surfaces, as would be the case otherwise.

Figure 42A:
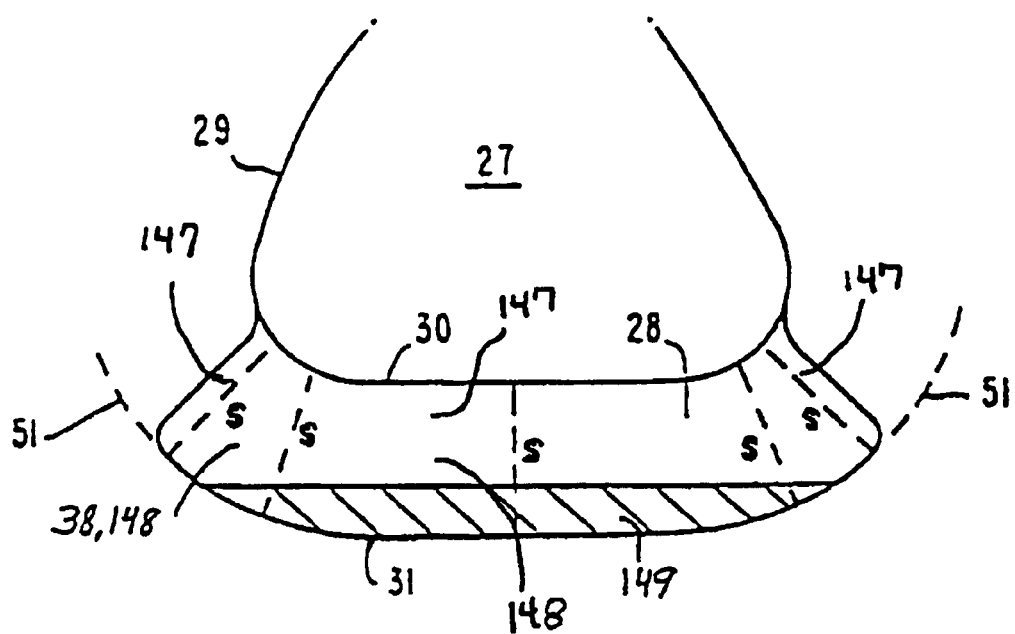
FIG. 42 shows several embodiments wherein the bottom sole includes most or all of the special contours of the designs and retains a flat upper surface.

The advantage of this approach is seen in the naturally rounded design example illustrated in FIG. 42A, which shows some contours on the relatively softer midsole sides, which are subject to less wear but benefit from greater traction for stability and ease of deformation, while the relatively harder rounded bottom sole provides good wear for the load-bearing areas.

Figure 42C:
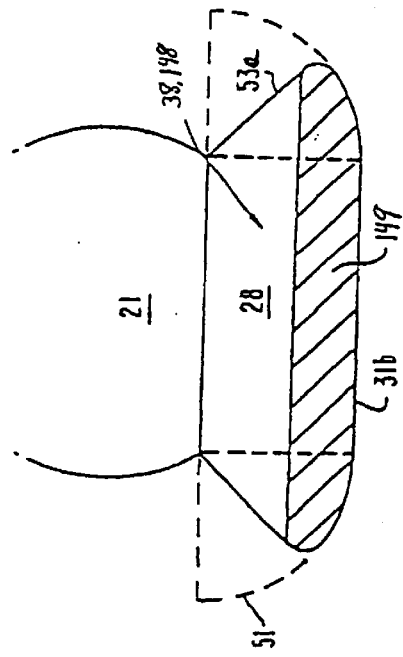
Figure 42D:
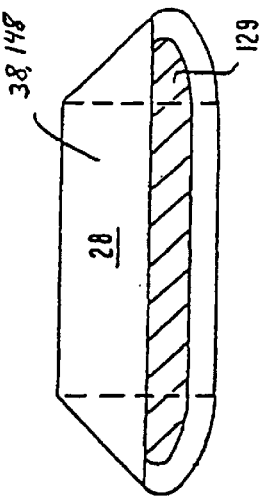
Figure 42B:
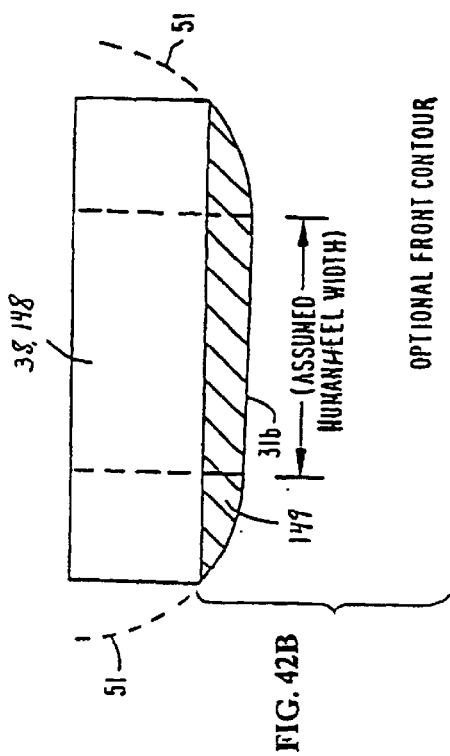

FIG. 42B shows in a quadrant side design the concept applied to conventional street shoe heels, which are usually separated from the forefoot by a hollow instep area under the main longitudinal arch.

FIG. 42C shows in frontal plane cross-section the concept applied to the quadrant sided or single plane design and indicating in FIG. 42D in the shaded area 129 of the bottom sole that portion which should be honeycombed (axis on the horizontal plane) to reduce the density of the relatively hard outer sole to that of the midsole material to provide for relatively uniform shoe density.

Generally, insoles or sock liners should be considered structurally and functionally as part of the shoe sole, as should any shoe material between foot and ground, like the bottom of the shoe upper in a slip-lasted shoe or the board in a board-lasted shoe.

Figure 43:
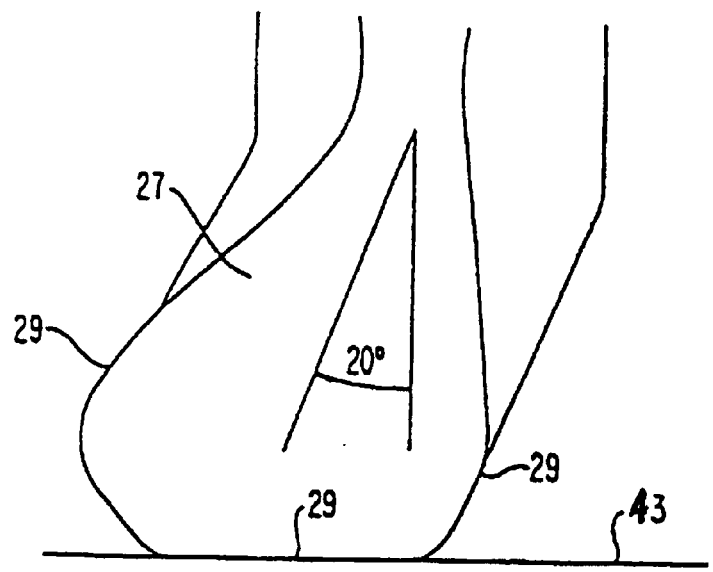
FIG. 43 is a rear view of a heel of a foot for explaining the use of a stationary sprain simulation test.

FIG. 43 shows in a real illustration a foot 27 in position for a new biomechanical test that is the basis for the discovery that ankle sprains are in fact unnatural for the bare foot. The test simulates a lateral ankle sprain, where the foot 27—on the ground 43—rolls or tilts to the outside, to the extreme end of its normal range of motion, which is usually about 20 degrees at the outer surface of the foot 29, as shown in a rear view of a bare (right) heel in FIG. 43. Lateral (inversion) sprains are the most common ankle sprains, accounting for about three-fourths of all ankle sprains.

The especially novel aspect of the testing approach is to perform the ankle spraining simulation while standing stationary. The absence of forward motion is the key to the dramatic success of the test because otherwise it is impossible to recreate for testing purposes the actual foot and ankle motion that occurs during a lateral ankle sprain, and simultaneously to do it in a controlled manner, while at normal running speed or even jogging slowly, or walking. Without the critical control achieved by slowing forward motion all the way down to zero, any test subject would end up with a sprained ankle.

That is because actual running in the real world is dynamic and involves a repetitive force maximum of three times one's full body weight for each footstep, with sudden peaks up to roughly five or six times for quick stops, missteps, and direction changes, as might be experienced when spraining an ankle. In contrast, in the static simulation test, the forces are tightly controlled and moderate, ranging from no force at all up to whatever maximum amount that is comfortable.

The Stationary Sprain Simulation Test (SSST) consists simply of standing stationary with one foot bare and the other shod with any shoe. Each foot alternately is carefully tilted to the outside up to the extreme end of its range of motion, simulating a lateral ankle sprain.

The SSST clearly identifies what can be no less than a fundamental problem in existing shoe design. It demonstrates conclusively that nature's biomechanical system, the bare foot, is far superior in stability to man's artificial shoe design. Unfortunately, it also demonstrates that the shoe's severe instability overpowers the natural stability of the human foot and synthetically creates a combined biomechanical system that is artificially unstable. The shoe is the weak link.

The test shows that the bare foot is inherently stable at the approximate 20 degree end of normal joint range because of the wide, steady foundation the bare heel 29 provides the ankle joint, as seen in FIG. 43. In fact, the area of physical contact of the bare heel 29 with the ground 43 is not much less when tilted all the way out to 20 degrees as when upright at 0 degrees.

The SSST provides a natural yardstick, totally missing until now, to determine whether any given shoe allows the foot within it to function naturally. If a shoe cannot pass this simple test, it is positive proof that a particular shoe is interfering with natural foot and ankle biomechanics. The only question is the exact extent of the interference beyond that demonstrated by the SSST.

Conversely, the applicant's designs employ shoe soles thick enough to provide cushioning (thin-soled and heel-less moccasins do pass the test, but do not provide cushioning and only moderate protection) and naturally stable performance, like the bare foot, in the SSST.

Figure 44:
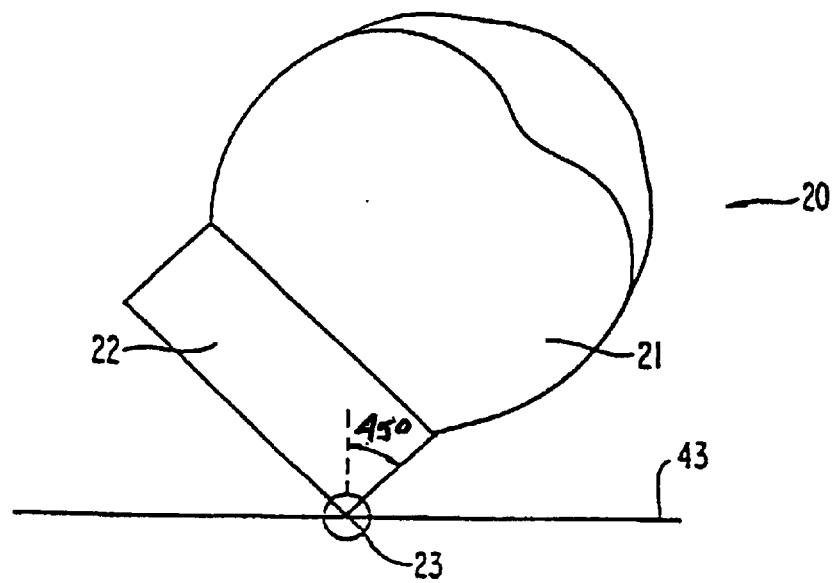
FIG. 44 is a rear view of a conventional athletic shoe rotating in an unstable manner about an edge of its sole when the shoe sole is tilted to the outside.

FIG. 44 shows that, in complete contrast the foot equipped with a conventional athletic shoe, designated generally by the reference numeral 20 and having an upper 21, though initially very stable while resting completely flat on the ground, becomes immediately unstable when the shoe sole 22 is tilted to the outside. The tilting motion lifts from contact with the ground all of the shoe sole 22 except the artificially sharp edge of the bottom outside corner. The shoe sole instability increases the farther the foot is rolled laterally. Eventually, the instability induced by the shoe itself is so great that the normal load-bearing pressure of full body weight would actively force an ankle sprain, if not controlled. The abnormal tilting motion of the shoe does not stop at the bare foot's natural 20 degree limit, as can be seen from the 45 degree tilt of the shoe heel in FIG. 44.

That continued outward rotation of the shoe past 20 degrees causes the foot to slip within the shoe, shifting its position within the shoe to the outside edge, further increasing the shoe's structural instability. The slipping of the foot within the shoe is caused by the natural tendency of the foot to slide down the typically flat surface of the tilted shoe sole; the more the tilt, the stronger the tendency. The heel is shown in FIG. 44 because of its primary importance in sprains due to its direct physical connection to the ankle ligaments that are torn in an ankle sprain and also because of the heel's predominant role within the foot in bearing body weight.

It is easy to see in the two figures, FIGS. 43 and 44, how totally different the physical shape of the natural bare foot is compared to the shape of the artificial, conventional shoe sole. It is strikingly odd that the two objects, which apparently both have the same biomechanical function, have completely different physical shapes. Moreover, the shoe sole clearly does not deform the same way the human foot sole does, primarily as a consequence of its dissimilar shape.

Figure 45A:
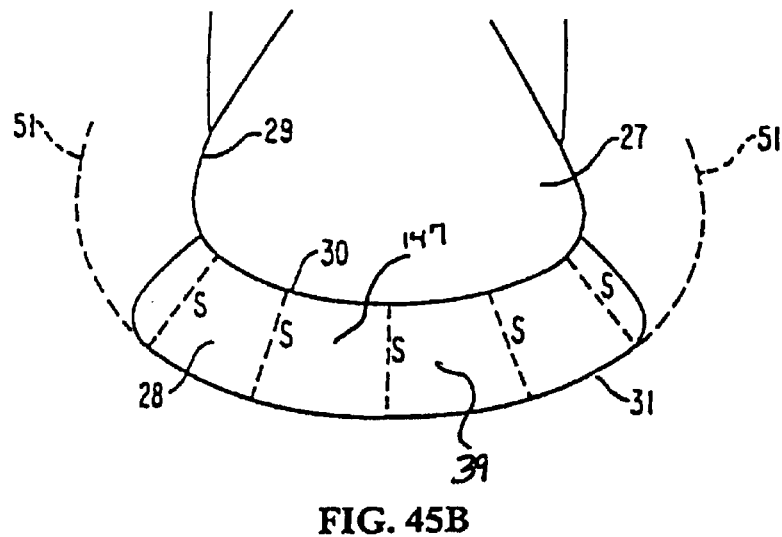
FIGS. 45A–45C illustrate functionally the principles of natural deformation as applied to the shoe soles of the invention.
Figure 45B:
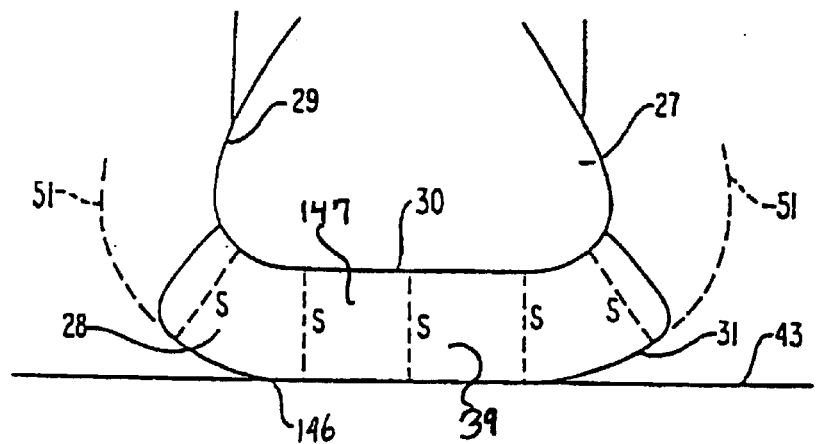
Figure 45C:
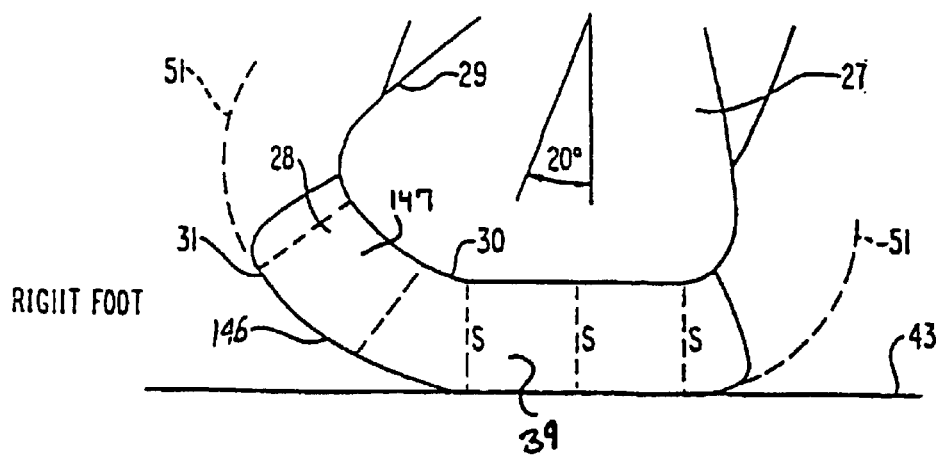

FIGS. 45A–45C illustrate clearly the principle of natural deformation as it applies to the applicant's designs, even though design diagrams like those preceding are normally shown in an ideal state, without any functional deformation, obviously to show their exact shape for proper construction. That natural structural shape, with its rounded paralleling the foot, enables the shoe is sole to deform naturally like the foot. The natural deformation feature creates such an important functional advantage it will be illustrated and discussed here fully. Note in the figures that even when the shoe sole shape is deformed, the constant shoe sole thickness in the frontal plane feature of the invention is maintained.

FIG. 45A shows upright, unloaded and therefore undeformed the fully rounded shoe sole design indicated in FIG. 15 above. FIG. 45A shows a fully rounded shoe sole design that follows the natural rounded of all of the foot sole, the bottom as well as the sides. The fully rounded shoe sole assumes that the resulting slightly rounded bottom when unloaded will deform under load as shown in FIG. 45B and flatten just as the human foot bottom is slightly rounded unloaded but flattens under load, like FIG. 14 above. Therefore, the shoe sole material must be of such composition as to allow the natural deformation following that of the foot. The design applies particularly to the heel, but to the rest of the shoe sole as well. By providing the closest possible match to the natural shape of the foot, the fully rounded design allows the foot to function as naturally as possible. Under load, FIG. 45A would deform by flattening to look essentially like FIG. 45B.

FIGS. 45A and 45B show in frontal plane cross-section the Theoretically Ideal Stability Plane 51 which is also theoretically ideal for efficient natural motion of all kinds, including running, jogging or walking. For any given individual, the Theoretically Ideal Stability Plane 51 is determined, first, by the desired shoe sole thickness (s) in a frontal plane cross section, and, second, by the is natural shape of the individual's foot surface 29.

For the case shown in FIG. 45B, the Theoretically Ideal Stability Plane 51 for any particular individual (or size average of individuals) is determined, first, by the given frontal plane cross-section shoe sole thickness (s); second, by the natural shape of the individual's foot;. and, third, by the frontal plane cross section width of the individual's load-bearing footprint which is defined as the upper surface of the shoe sole that is in physical contact with and supports the human foot sole.

FIG. 45B shows the same fully rounded design when upright, under normal load (body weight) and therefore deformed naturally in a manner very closely paralleling the natural deformation under the same load of the foot. An almost identical portion of the foot sole that is flattened in deformation is also flattened in deformation in the shoe sole. FIG. 45C shows the same design when tilted outward 20 degrees laterally, the normal bare foot limit; with virtually equal accuracy it shows the opposite foot tilted 20 degrees inward, in fairly severe pronation. As shown, the deformation of the shoe sole 28 again very closely parallels that of the foot, even as it tilts. Just as the area of foot contact is almost as great when tilted 20 degrees, the flattened area of the deformed shoe sole is also nearly the same as when upright. Consequently, the bare foot fully supported structurally and its natural stability is maintained undiminished, regardless of shoe tilt. In marked contrast, a conventional shoe, shown in FIG. 2, makes contact with the ground with only its relatively sharp edge when tilted and is therefore inherently unstable.

The capability to deform naturally is a design feature of the applicant's naturally rounded shoe sole designs, whether fully rounded or rounded only at the sides, though the fully rounded design is most optimal and is the most natural, general case, assuming shoe sole material such as to allow natural deformation. It is an important feature because, by following the natural deformation of the human foot, the naturally deforming shoe sole can avoid interfering with the natural biomechanics of the foot and ankle.

FIG. 45C also represents with reasonable accuracy a shoe sole design corresponding to FIG. 45B, a naturally rounded shoe sole with a conventional built-in flattening deformation, as in FIG. 14 above, except that design would have a slight crimp at 146. Seen in this light, the naturally rounded side design in FIG. 45B is a more conventional, conservative design that is a special case of the more generally fully rounded design in FIG. 45A, which is the closest to the natural form of the foot, but the least conventional. The natural deformation of the applicant's shoe sole design follows that of the foot very closely so that both provide a nearly equal flattened base to stabilize the foot.

Figure 46:
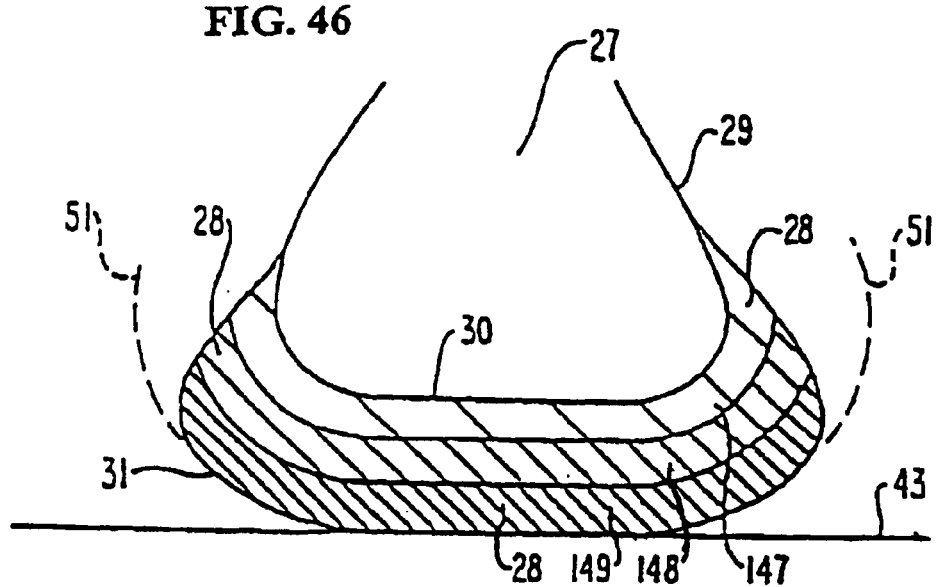
FIG. 46 shows variations in the relative density of the shoe sole including the shoe insole to maximize an ability of the sole to deform naturally.

FIG. 46 shows the preferred relative density of the shoe sole, including the insole as a part, in order to maximize the shoe sole's ability to deform naturally following the natural deformation of the foot sole. Regardless of how many shoe sole layers (including insole) or laminations of differing material densities and flexibility are used in total, the softest and most flexible material 147 should be closest to the foot sole, with a progression through less soft 148, such as a midsole or heel lift, to the firmest and least flexible 149 at the outermost shoe sole layer, the bottom sole. This arrangement helps to avoid the unnatural side lever arm/torque problem mentioned in the previous several figures. That problem is most severe when the shoe sole is relatively hard and nondeforming uniformly throughout the shoe sole, like most conventional street shoes, since hard material transmits the destabilizing torque most effectively by providing a rigid lever arm.

The relative density shown in FIG. 46 also helps to allow the shoe sole to duplicate the same kind of natural deformation exhibited by the bare foot sole in FIG. 43, since the shoe sole layers closest to the foot, and therefore with the most severe contours have to deform the most in order to flatten like the barefoot and consequently need to be soft to do so easily. This shoe sole arrangement also replicates roughly the natural bare foot, which is covered with a very tough "Seri boot" outer surface (protecting a softer cushioning interior of fat pads) among primitive barefoot populations.

Finally, the use of natural relative density as indicated in this figure will allow more anthropomorphic embodiments of the applicant's designs (right and left sides of FIG. 46 show variations of different degrees) with sides going higher around the side rounded of the foot and thereby blending more naturally with the sides of the foot. These conforming sides will not be effective as destabilizing lever arms because the shoe sole material there would be soft and unresponsive in transmitting torque, since the lever arm will bend.

As a point of clarification, the forgoing principle of preferred relative density refers to proximity to the foot and is not inconsistent with the term "uniform density" used in conjunction with certain embodiments of applicant's invention. Uniform shoe sole density is preferred strictly in the sense of preserving even and natural support to the foot like the ground provides, so that a neutral starting point can be established, against which so-called improvements can be measured. The preferred uniform density is in marked contrast to the common practice in athletic shoes today, especially those beyond cheap or "bare bones" models, of increasing or decreasing the density of the shoe sole, particularly in the midsole, in various areas underneath the foot to provide extra support or special softness where believed necessary. The same effect is also created by areas either supported or unsupported by the tread pattern of the bottom sole. The most common example of this practice is the use of denser midsole material under the inside portion of the heel, to counteract excessive pronation.

Figure 47:
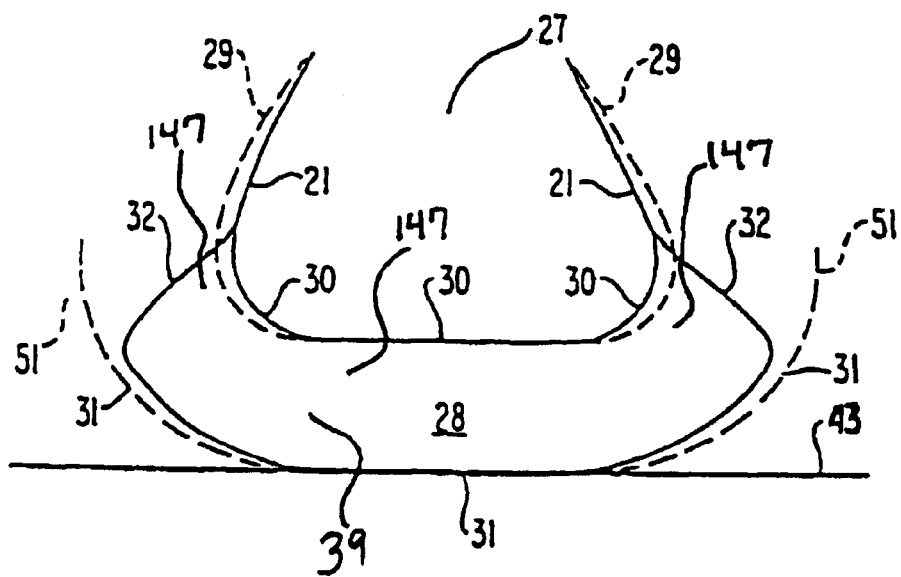
FIG. 47 shows a shoe having naturally rounded sides bent inwardly from a conventional design so then when worn the shoe approximates a custom fit.

FIG. 47 illustrates that the applicant's naturally rounded shoe sole sides can be made to provide a fit so close as to approximate a custom fit. By molding each mass-produced shoe size with sides that are bent in somewhat from the position 29 they would normally be in to conform to that standard size shoe last, the shoe soles so produced will very gently hold the sides of each individual foot exactly. Since the shoe sole is designed as described in connection with FIG. 46 to deform easily and naturally like that of the bare foot, it will deform easily to provide this designed-in custom fit. The greater the flexibility of the shoe sole sides, the greater the range of individual foot size variations can be custom fit by a standard size. This approach applies to the fully rounded design described here in FIG. 45A and in FIG. 15 above, which would be even more effective than the naturally rounded sides design shown in FIG. 47.

Besides providing a better fit, the intentional undersizing of the flexible shoe sole sides of FIG. 47 allows for a simplified design utilizing a geometric approximation of the true actual rounded of the human. This geometric approximation is close enough to provide a virtual custom fit, when compensated for by the flexible undersizing from standard shoe lasts described above.

FIG. 48 illustrates a fully rounded design, but abbreviated along the sides to only essential structural stability and propulsion shoe sole elements as shown in FIG. 11G–L above combined with freely articulating structural elements underneath the foot. The unifying concept is that, on both the sides and underneath the main load-bearing portions of the shoe sole, only the important structural (i.e. bone) elements of the foot should be supported by the shoe sole, if the natural flexibility of the foot is to be paralleled accurately in shoe sole flexibility, so that the shoe sole does not interfere with the foot's natural motion. In a sense, the shoe sole should be composed of the same main structural elements as the foot and they should articulate with each other just as do the main joints of the foot.

Figure 48A:
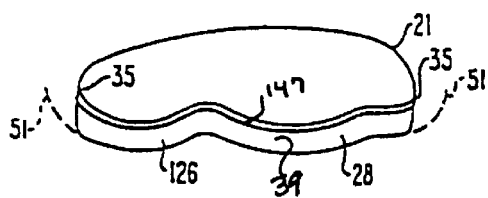
FIG. 48 shows a shoe sole having a fully rounded design but having sides which are abbreviated to the essential structural stability and propulsion elements and are combined and integrated into discontinuous structural elements underneath the foot that simulate those of the foot.
Figure 48B:
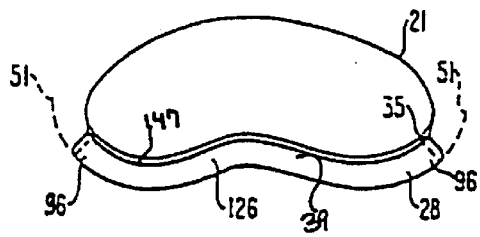
Figure 48C:
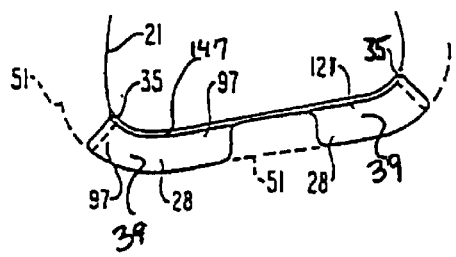
Figure 48D:
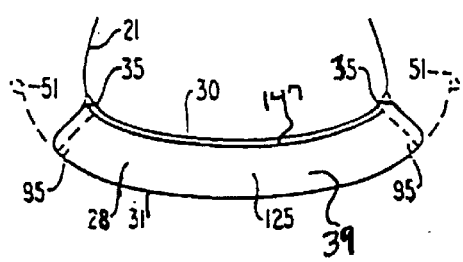
Figure 48E:
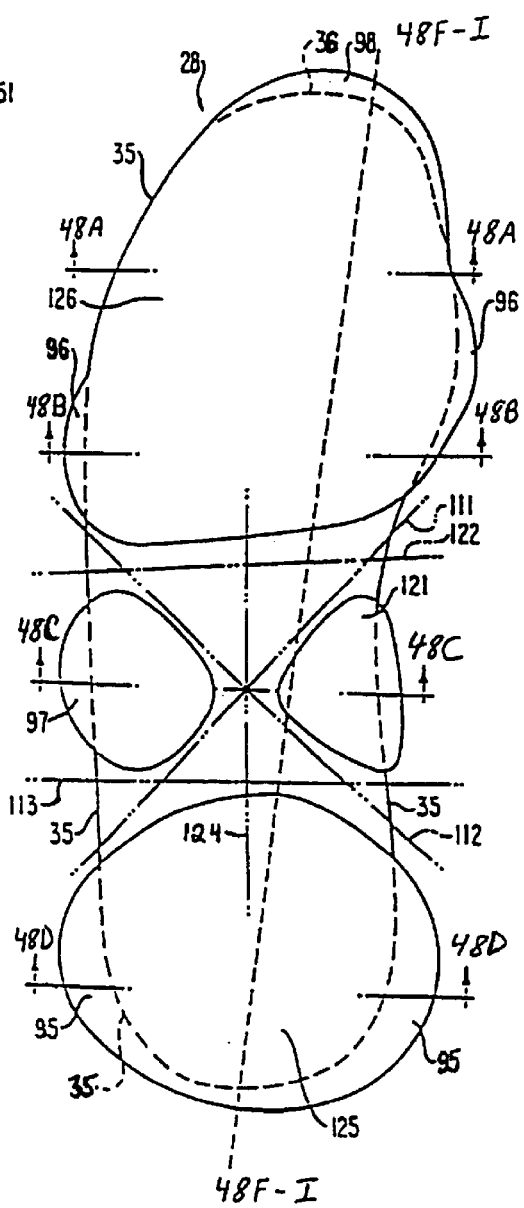
Figure 48E:
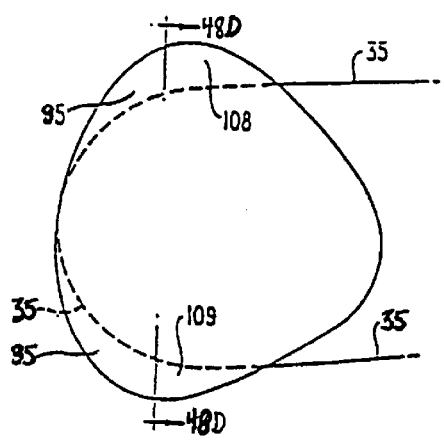

FIG. 48E shows the horizontal plane bottom view of the right foot corresponding to the fully rounded design previously described, but abbreviated along the sides to only essential structural support and propulsion elements. Shoe sole material density can be increased in the unabbreviated essential elements to compensate for increased pressure loading there. The essential structural support elements are the base and lateral tuberosity of the calcaneus 95, the heads of the metatarsals 96, and the base of the fifth metatarsal 97 (and the adjoining cuboid in some individuals). They must be supported both underneath and to the outside edge of the foot for stability. The essential propulsion element is the head of the first distal phalange 98. FIG. 48 shows that the naturally rounded stability sides need not be used except in the identified essential areas. Weight savings and flexibility improvements can be made by omitting the non-essential stability sides.

The design of the portion of the shoe sole directly underneath the foot shown in FIG. 48 allows for unobstructed natural inversion/eversion motion of the calcaneus by providing maximum shoe sole flexibility particularly between the base of the calcaneus 125 (heel) and the metatarsal heads 126 (forefoot) along an axis 124. An unnatural torsion occurs about that axis if flexibility is insufficient so that a conventional shoe sole interferes with the inversion/eversion motion by restraining it. The object of the design is to allow the relatively more mobile (in inversion and eversion) calcaneus to articulate freely and independently from the relatively more fixed forefoot instead of the fixed or fused structure or lack of stable structure between the two in conventional designs. In a sense, freely articulating joints are created in the shoe sole that parallel those of the foot. The design is to remove nearly all of the shoe sole material between the heel and the forefoot, except under one of the previously described essential structural support elements, the base of the fifth metatarsal 97. An optional support for the main longitudinal arch 121 may also be retained for runners with substantial foot pronation, although it would not be necessary for many runners.

The forefoot can be subdivided (not shown) into its component essential structural support and propulsion elements, the individual heads of the metatarsal and the heads of the distal phalanges, so that each major articulating joint set of the foot is paralleled by a freely articulating shoe sole support propulsion element, an anthropomorphic design; various aggregations of the subdivision are also possible.

The design in FIG. 48 features an enlarged structural support at the base of the fifth metatarsal in order to include the cuboid, which can also come into contact with the ground under arch compression in some individuals. In addition, the design can provide general side support in the heel area, as in FIG. 48E or alternatively can carefully orient the stability sides in the heel area to the exact positions of the lateral calcaneal tuberosity 108 and the main base of the calcaneus 109, as in FIG. 48E (showing heel area only of the right foot). FIGS. 48A–48D show frontal plane cross sections of the left shoe and FIG. 48E shows a bottom view of the right foot, with flexibility axes 122, 124, 111, 112 and 113 indicated. FIG. 48F shows a sagittal plane cross section showing the structural elements joined by a very thin and relatively soft upper midsole layer. FIGS. 48G and 48H show similar cross sections with slightly different designs featuring durable fabric only (slip-lasted shoe), or a structurally sound arch design, respectively. FIG. 48I shows a side medial view of the shoe sole.

Figure 48J:
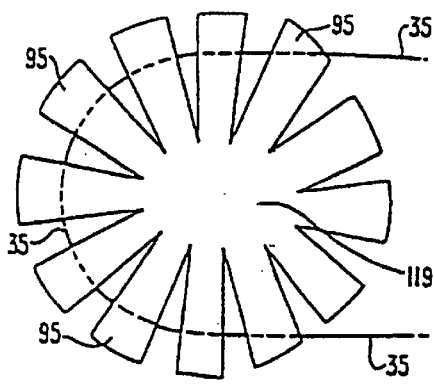
Figure 48F:
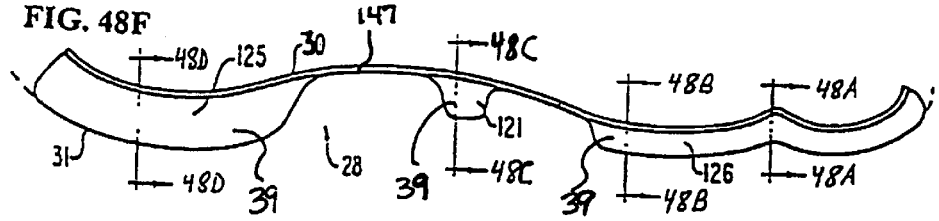
Figure 48G:
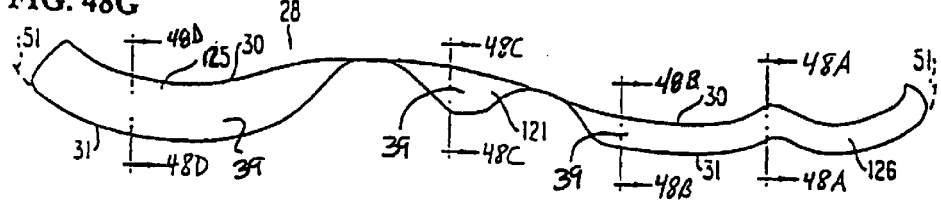
Figure 48H:
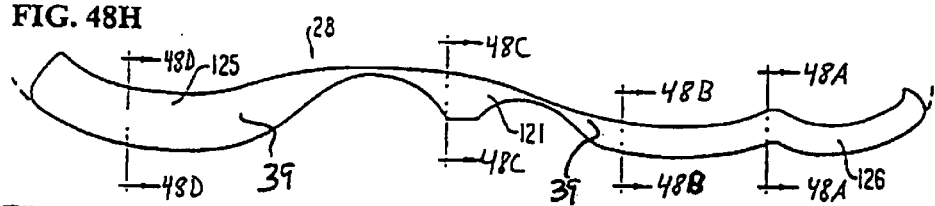
Figure 48I:
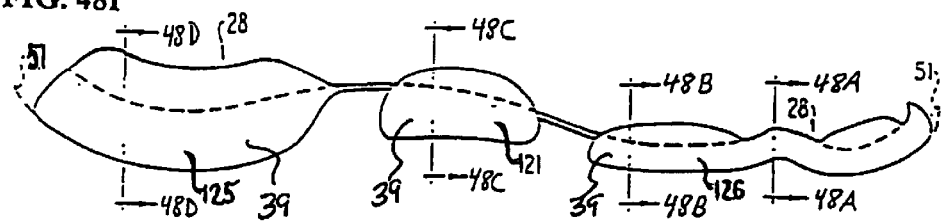

FIG. 48J shows a simple interim or low cost construction for the articulating shoe sole support element 95 for the heel (showing the heel area only of the right foot); while it is most critical and effective for the heel support element 95, it can also be used with the other elements, such as the base of the fifth metatarsal 97 and the long arch 121. The heel sole element 95 shown can be a single flexible layer or a lamination of layers. When cut from a flat sheet or molded in the general pattern shown, the outer edges can be easily bent to follow the contours of the foot, particularly the sides. The shape shown allows a flat or slightly rounded heel element 95 to be attached to a highly rounded shoe upper or very thin upper sole layer like that shown in FIG. 48F. Thus, a very simple construction technique can yield a highly sophisticated shoe sole design. The size of the center section 119 can be small to conform to a fully or nearly fully rounded design or larger to conform to a rounded sides design, where there is a large flattened sole area under the heel. The flexibility is provided by the removed diagonal sections, the exact proportion of size and shape can vary.

FIG. 49 shows use of the Theoretically Ideal Stability Plane 51 concept to provide natural stability in negative heel shoe soles that are less thick in the heel area than in the rest of the shoe sole; specifically, a negative heel version of the naturally rounded sides conforming to a load-bearing foot design shown in FIG. 14 above.

FIGS. 49A, 49B, and 49C represent frontal plane cross sections taken along the forefoot, at the base of the fifth metatarsal, and at the heel, thus illustrating that the shoe sole thickness is constant at each frontal plane cross section, even though that thickness varies from front to back, due to the sagittal plane variation 40 (shown hatched) causing a lower heel than forefoot, and that the thickness of the naturally rounded sides is equal to the shoe sole thickness in each FIG. 49A–49C cross-section. Moreover, in FIG. 49D, a horizontal plane overview or top view of the left foot sole, it can be seen that the horizontal rounded of the sole follows the preferred principle in matching, as nearly as practical, the rough footprint of the load-bearing foot sole.

The abbreviation of essential structural support elements can also be applied to negative heel shoe soles such as that shown in FIG. 49 and dramatically improves their flexibility. Negative heel shoe soles such as FIG. 49 can also be modified by inclusion of aspects of the other embodiments disclosed herein.

Figure 50A:
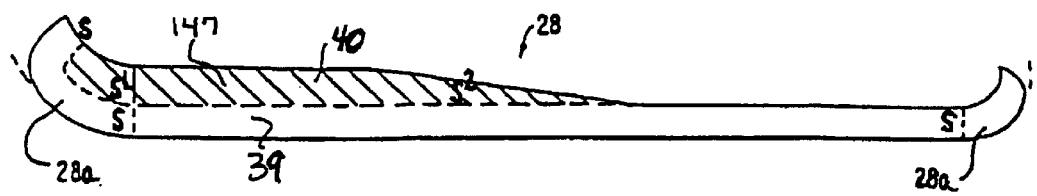
FIGS. 50A–50E show a plurality of side sagittal plane cross sectional views of examples of negative heel sole thickness variations (forefoot lift) to which the general approach shown in FIGS. 49A–49D can be applied.
Figure 50B:
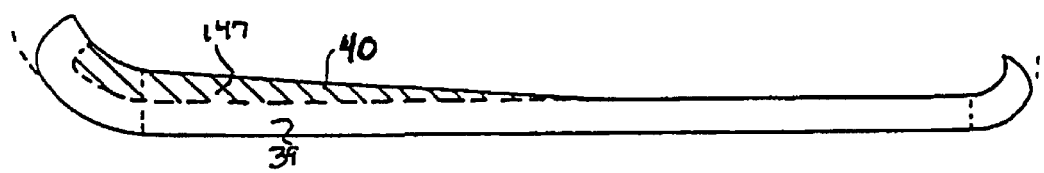
Figure 50C:
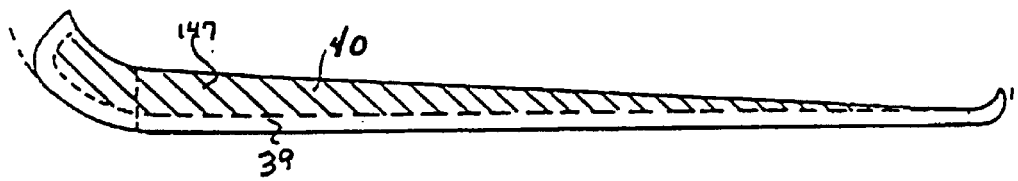
Figure 50D:
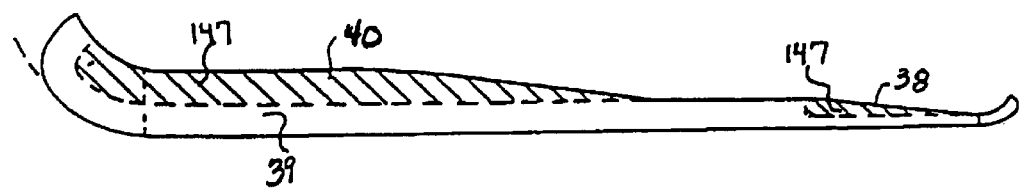
Figure 50E:
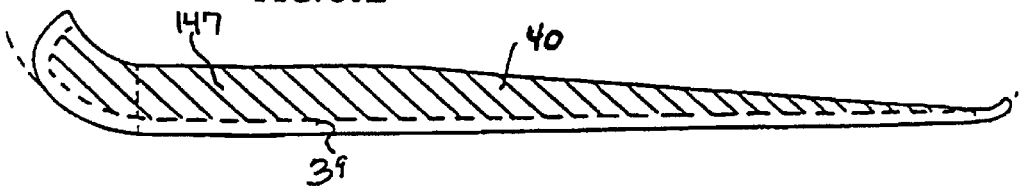

FIG. 50 shows, in FIGS. 50A–50D, possible sagittal plane shoe sole thickness variations for negative heel shoes. The hatched areas indicate the forefoot lift or wedge 40. At each point along the shoe soles seen in sagittal plane cross sections, the thickness varies as shown in FIGS. 50A–50D, while the thickness of the naturally rounded sides 28a, as measured in the frontal plane, equal and therefore vary directly with those sagittal plane thickness variations. FIG. 50A shows the same embodiment as FIG. 49.

FIG. 51 shows the application of the Theoretically Ideal Stability Plane concept in flat shoe soles that have no heel lift to provide for natural stability, maintaining the same thickness throughout, with rounded stability sides abbreviated to only essential structural support elements to provide the shoe sole with natural flexibility paralleling that of the human foot.

FIGS. 51A, 51B, and 51C represent frontal plane cross-sections taken along the forefoot, at the base of the fifth metatarsal, and at the heel, thus illustrating that the shoe sole thickness is constant at each frontal plane cross section, while constant in the sagittal plane from front to back, so that the heel and forefoot have the same shoe sole thickness, and that the thickness of the naturally rounded sides is equal to the shoe sole thickness in each FIG. 51A–51C cross-section. Moreover, in FIG. 51C, a horizontal plane overview or top view of the left foot sole, it can be seen that the horizontal rounded of the sole follows the preferred principle in matching, as nearly as practical, the rough footprint of the load-bearing foot sole. FIG. 51E, a sagittal plane cross section, shows that shoe sole thickness is constant in that plane.

FIG. 51 shows the applicants prior invention of rounded sides abbreviated to essential structural elements, as applied to a flat shoe sole. FIG. 51 shows the horizontal plane top view of fully rounded shoe sole of the left foot abbreviated along the sides to only essential structural support and propulsion elements (shown hatched). Shoe sole material density can be increased in the unabbreviated essential elements to compensate for increased pressure loading there. The essential structural support elements are the base and lateral tuberosity of the calcaneus 95, the heads of the metatarsals 96, and base of the fifth metatarsal 97. They must be supported both underneath and to the outside for stability. The essential propulsion element is the head of the first distal phalange 98.

The medial (inside) and lateral (outside) sides supporting the base and lateral tuberosity of the calcaneus are shown in FIG. 51 oriented in a conventional way along the longitudinal axis of the shoe sole, in order to provide direct structural support to the base and lateral tuberosity of the calcaneus, but can be located also along either side of the horizontal plane subtalar ankle joint axis . FIG. 51 shows that the naturally rounded stability sides need not be used except in the identified essential areas. Weight savings and flexibility improvements can be made by omitting the non-essential stability sides. A horizontal plane bottom view (not shown) of FIG. 51 would be the exact reciprocal or converse of FIG. 51 with the peaks and valleys contours exactly reversed.

Flat shoe soles such as FIG. 51 can also be modified by inclusion of aspects of the other embodiments disclosed herein.

Central midsole section 188 and upper section 187 in FIG. 12 must fulfill a cushioning function which frequently calls for relatively soft midsole material. The shoe sole thickness effectively decreases in the FIG. 12 embodiment when the soft central section is deformed under weight-bearing pressure to a greater extent than the relatively firmer sides.

In order to control this effect, it is necessary to measure it. What is required is a methodology of measuring a portion of a static shoe sole at rest that will indicate the resultant thickness under deformation. A simple approach is to take the actual least distance thickness at any point and multiply it times a factor for deformation or "give", which is typically measured in durometers (on Shore A scale), to get a resulting thickness under a standard deformation load. Assuming a linear relationship (which can be adjusted empirically in practice), this method would mean that a shoe sole midsection of 1 inch thickness and a fairly soft 30 durometer would be roughly functionally equivalent under equivalent load-bearing deformation to a shoe midsole section of ½ inch and a relatively hard 60 durometer; they would both equal a factor of 30 inch-durometers. The exact methodology can be changed or improved empirically, but the basic point is that static shoe sole thickness needs to have a dynamic equivalent under equivalent loads, depending on the density of the shoe sole material.

Since the Theoretically Ideal Stability Plane 51 has already been generally defined in part as having a constant frontal plane thickness and preferring a uniform material density to avoid arbitrarily altering natural foot motion, it is logical to develop a non-static definition that includes compensation for shoe sole material density. The Theoretically Ideal Stability Plane 51 defined in dynamic terms would alter constant thickness to a constant multiplication product of thickness times density.

Using this restated definition of the Theoretically Ideal Stability Plane 51 presents an interesting design possibility: the somewhat extended width of shoe sole sides that are required under the static definition of the Theoretically Ideal Stability Plane 51 could be reduced by using a higher density midsole material in the naturally rounded sides.

Figure 52:
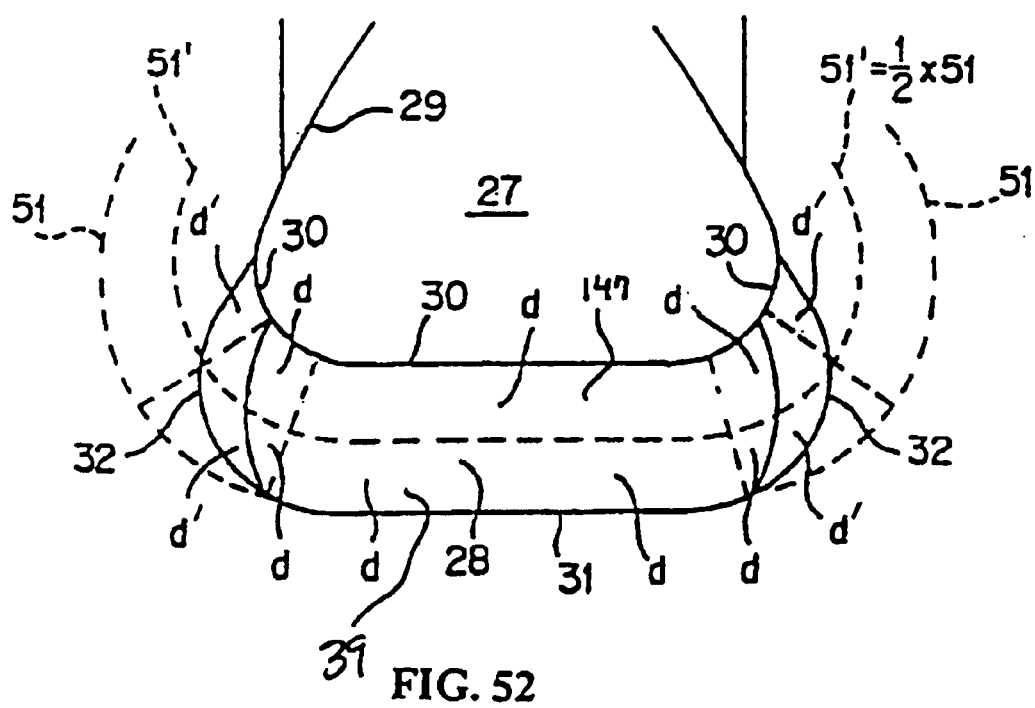
FIG. 52 shows, in frontal plane cross section at the heel, the use of a high density (d') midsole material on the naturally rounded sides and a low density (d) midsole material everywhere else to reduce side width.

FIG. 52 shows, in frontal plane cross section at the heel, the use of a high density (d') midsole material on the naturally rounded sides and a low density (d) midsole material everywhere else to reduce side width. To illustrate the principle, it was assumed in FIG. 52 that density (d') is twice that of density (d), so the effect is somewhat exaggerated, but the basic point is that shoe sole width can be reduced significantly by using the Theoretically Ideal Stability Plane 51 with a definition of thickness that compensates for dynamic force loads. In the FIG. 52 example, about one fourth of an inch in width on each side is saved under the revised definition, for a total width reduction of one half inch, while rough functional equivalency should be maintained, as if the frontal plane thickness and density were each unchanging.

As shown in FIG. 52, the boundary between sections of different density is indicated by the line 45 and the line 51' parallel to 51 at half the distance from the outer surface of the foot 29.

Note that the design in FIG. 52 uses low density midsole material, which is effective for cushioning, throughout that portion of the shoe sole that would be directly load-bearing from roughly 10 degrees of inversion to roughly 10 degrees eversion, the normal range of maximum motion during athletics; the higher density midsole material is tapered in from roughly 10 degrees to 30 degrees on both sides, at which ranges cushioning is less critical than providing stabilizing support.

Figures 53A, 53B, 53C:
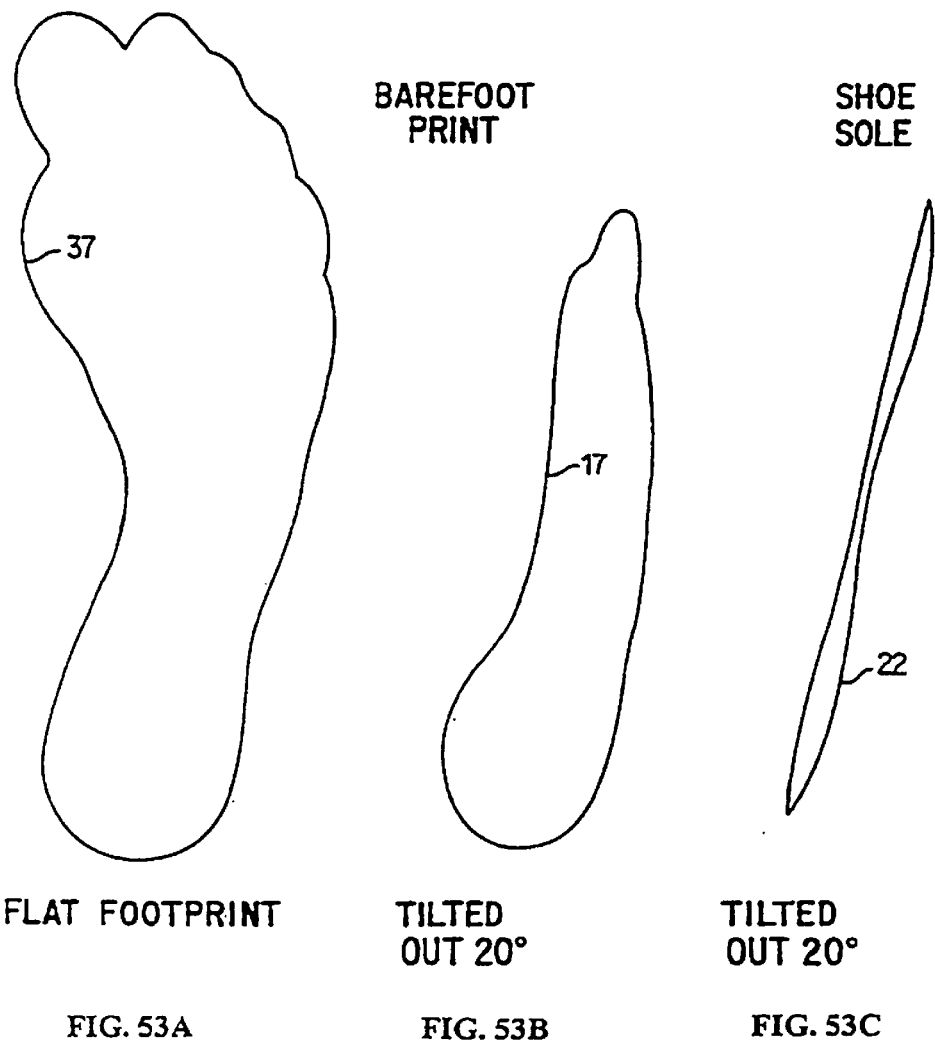
FIG. 53A shows the foot upright with its sole flat on the ground.
FIG. 53B shows the foot tilted out 20 degrees to about its normal limit.
FIG. 53C shows a shoe sole of the same size when tilted out 20 degrees to the same position as FIG. 53B. The right foot and shoe are shown.

FIG. 53 show the footprints of the natural barefoot sole and shoe sole. The footprints are the areas of contact between the bottom of the foot or shoe sole and the flat, horizontal plane of the ground, under normal body weight-bearing conditions. FIG. 53A shows a typical right footprint outline 37 when the foot is upright with its sole flat on the ground.

FIG. 53B shows the footprint outline 17 of the same foot when tilted out 20 degrees to about its normal limit; this footprint corresponds to the position of the foot shown in FIG. 43 above. Critical to the inherent natural stability of the barefoot is that the area of contact between the heel and the ground is virtually unchanged, and the area under the base of the fifth metatarsal and cuboid is narrowed only slightly. Consequently, the barefoot maintains a wide base of support even when tilted to its most extreme lateral position.

The major difference shown in FIG. 53B is clearly in the forefoot, where all of the heads of the first through fourth metatarsals and their corresponding phalanges no longer make contact with the ground. Of the forefoot, only the head of the fifth metatarsal continues to make contact with the ground, as does its corresponding phalange, although the phalange does so only slightly. The forefoot motion of the forefoot is relatively great compared to that of the heel.

FIG. 53C shows a shoe sole print outline of a shoe sole of the same size as the bare foot in FIGS. 53A & 53B when tilted out 20 degrees to the same position as FIG. 53B; this position of the shoe sole corresponds to that shown in FIG. 44 above. The shoe sole maintains only a very narrow bottom edge in contact with the ground, an area of contact many times less than the bare foot.

Figure 54:
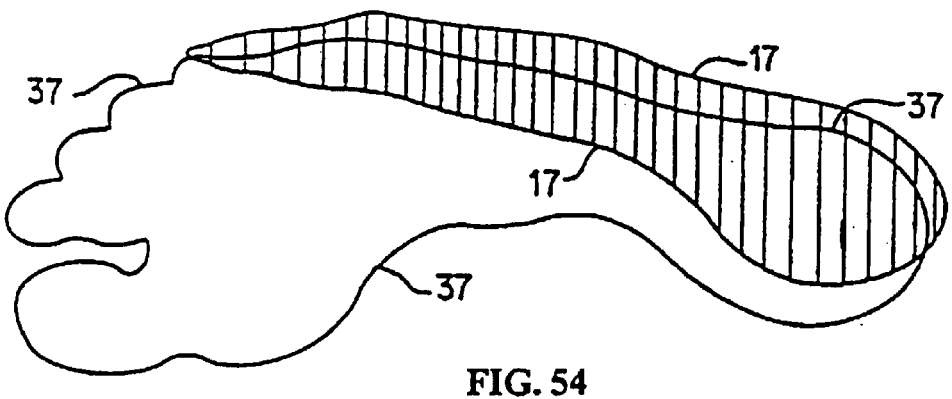
FIG. 54 shows footprints like those shown in FIGS. 53A and 53B of a right bare foot upright and tilted out 20 degrees, but showing also their actual relative positions to each other as a high arched foot rolls outward from upright to tilted out 20 degrees.

FIG. 54 shows two footprints like footprint 37 in FIG. 53A of a bare foot As upright and footprint 17 in FIG. 53B of a bare foot tilted out 20 degrees, but showing also their actual relative positions to each other as the foot rolls outward from upright to tilted out 20 degrees. The bare foot tilted footprint is shown hatched. The position of tilted footprint 17 so far to the outside of upright footprint 37 demonstrates the requirement for greater shoe sole width on the lateral side of the shoe to keep the foot from simply rolling off of the shoe sole; this problem is in addition to the inherent problem caused by the rigidity of the conventional shoe sole. The footprints are of a high arched foot.

FIG. 55 shows the applicant's invention of shoe sole with a lateral stability sipe 11 in the form of a vertical slit. The lateral stability sipe allows the shoe sole to flex in a manner that parallels the foot sole, as seen is FIGS. 53 & 54. The lateral stability sipe 11 allows the forefoot of the shoe sole to pivot off the ground with the wear's forefoot when the wearer's foot rolls out laterally. At the same time, it allows the remaining shoe sole to remain flat on the ground under the wearer's load-bearing tilted footprint 17 in order to provide a firm and natural base of structural support to the wearer's heel, his fifth metatarsal base and head, as well as cuboid and fifth phalange and associated softer tissues. In this way, the lateral stability sipe provides the wearer of even a conventional shoe sole with lateral stability like that of the bare foot. All types of shoes can be distinctly improved with this invention, even women's high heeled shoes.

With the lateral stability sipe, the natural supination of the foot, which is its outward rotation during load-bearing, can occur with greatly reduced obstruction. The functional effect is analogous to providing a car with independent suspension, with the axis aligned correctly. At the same time, the principle load-bearing structures of the foot are firmly supported with no sipes directly underneath.

Figure 55A:
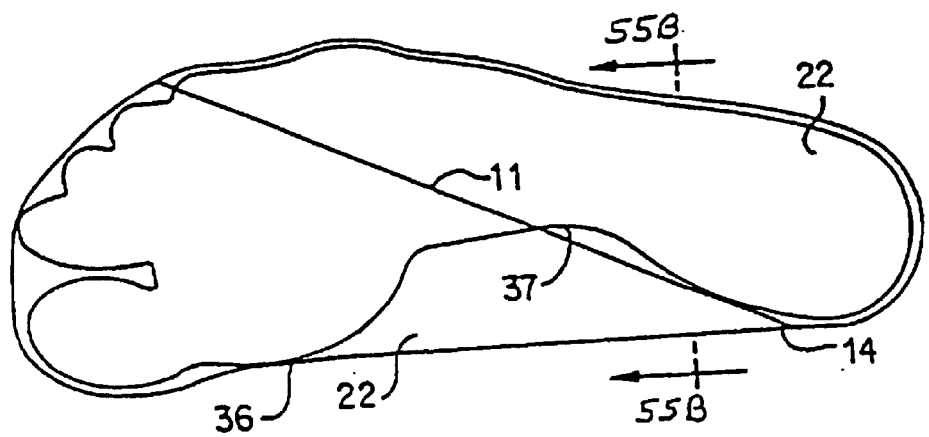
FIG. 55A is a top view of a conventional shoe sole with a corresponding outline of the wearer's footprint superimposed on it to identify the position of the lateral stability sipe relative to the wearer's foot.

FIG. 55A is a top view of a conventional shoe sole with a corresponding outline of the wearer's footprint superimposed on it to identify the position of the lateral stability sipe 11, which is fixed relative to the wearer's foot, since it removes the obstruction to the foot's natural lateral flexibility caused by the conventional shoe sole.

With the lateral stability sipe 11 in the form of a vertical slit, when the foot sole is upright and flat, the shoe sole provides firm structural support as if the sipe were not there. No rotation beyond the flat position is possible with a sipe in the form of a slit, since the shoe sole on each side of the slit prevents further motion.

Many variations of the lateral stability sipe 11 are possible to provide the same unique functional goal of providing shoe sole flexibility along the general axis shown in FIG. 55. For example, the slit can be of various depths depending on the flexibility of the shoe sole material used; the depth can be entirely through the shoe sole, so long as some flexible material acts as a joining hinge, like the cloth of a fully lasted shoe, which covers the bottom of the foot sole, as well as the sides. The slits can be multiple, in parallel or askew. They can be offset from vertical. They can be straight lines, jagged lines, curved lines or discontinuous lines.

Although slits are preferred, other sipe forms such as channels or variations in material densities as described above can also be used, though many such forms will allow varying degrees of further pronation rotation beyond the flat position, which may not be desirable, at least for some categories of runners. Other methods in the existing art can be used to provide flexibility in the shoe sole similar to that provided by the lateral stability sipe along the axis shown in FIG. 55.

The axis shown in FIG. 55 can also vary somewhat in the horizontal plane. For example, the footprint outline 37 shown in FIG. 55 is positioned to support the heel of a high arched foot; for a low arched foot tending toward excessive pronation, the medial origin 14 of the lateral stability sipe would be moved forward to accommodate the more inward or medial position of pronator's heel. The axis position can also be varied for a corrective purpose tailored to the individual or category of individual: the axis can be moved toward the heel of a rigid, high arched foot to facilitate pronation and flexibility, and the axis can be moved away from the heel of a flexible, low arched foot to increase support and reduce pronation.

It should be noted that various forms of firm heel counters and motion control devices in common use can interfere with the use of the lateral stability sipe by obstructing motion along its axis; therefore, the use of such heel counters and motion control devices should be avoided. The lateral stability sipe may also compensate for shoe heel-induced outward knee cant.

Figure 55B:
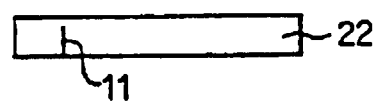
FIG. 55B is a cross section of the shoe sole with lateral stability sipe.

FIG. 55B is a cross section of the shoe sole 22 with lateral stability sipe 11. The shoe sole thickness is constant but could vary as do many conventional and unconventional shoe soles known to the art. The shoe sole could be conventionally flat like the ground or conform to the shape of the wearer's foot.

Figure 55C:
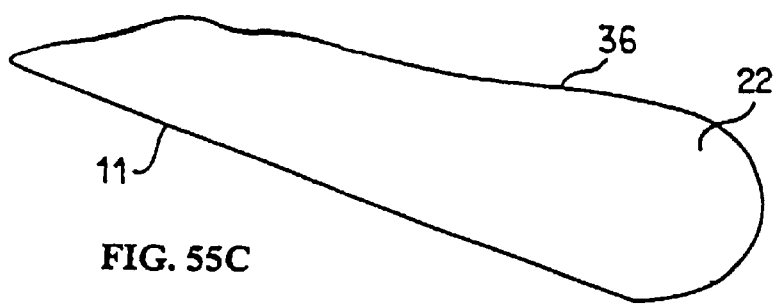
FIG. 55C is a top view like FIG. 55A, but showing the print of the shoe sole with a lateral stability sipe when it is tilted outward 20 degrees.

FIG. 55C is a top view like FIG. 55A, but showing the print of the shoe sole with a lateral stability sipe when the shoe sole is tilted outward 20 degrees, so is that the forefoot of the shoe sole is not longer in contact with the ground, while the heel and the lateral section do remain flat on the ground.

Figure 56:
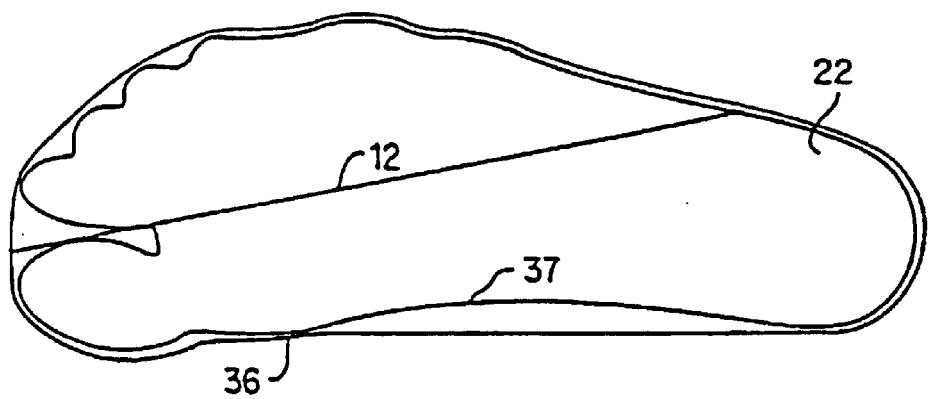
FIG. 56 shows a medial stability sipe that is analogous to the lateral sipe, but to provide increased pronation stability. The head of the first metatarsal and the first phalange are included with the heel to form a medial support section.

FIG. 56 shows a conventional shoe sole with a medial stability sipe 12 that is like the lateral sipe 11, but with a purpose of providing increased medial or pronation stability instead of lateral stability; the head of the first metatarsal and the first phalange are included with the heel to form a medial support section inside of a flexibility axis defined by the medial stability sipe 12. The medial stability sipe 12 can be used alone, as shown, or together with the lateral stability sipe 11, which is not shown.

Figure 57:
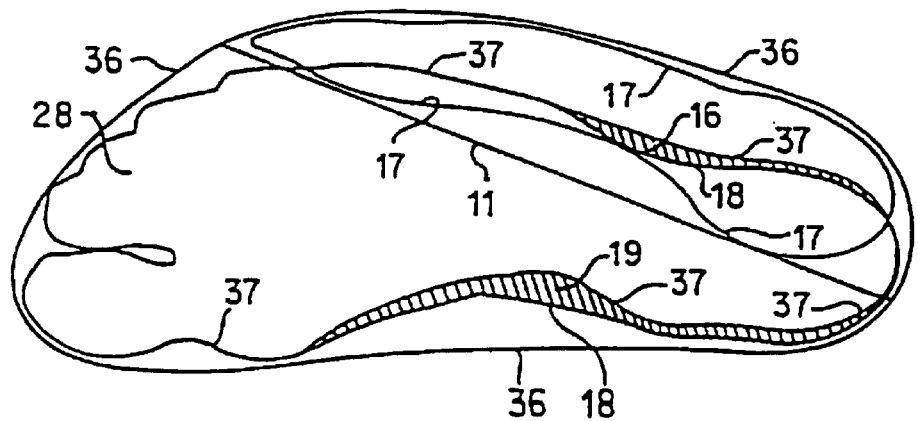
FIG. 57 shows footprints 37 and 17, like FIG. 54, of a right bare foot upright and tilted out 20 degrees, showing the actual relative positions to each other as a low arched foot rolls outward from upright to tilted out 20 degrees.

FIG. 57 shows footprints 37 and 17, like FIG. 54, of a right barefoot upright and tilted out 20 degrees, showing the actual relative positions to each other as a low arched foot rolls outward from upright to tilted out 20 degrees. The low arched foot is particularly noteworthy because it exhibits a wider range of motion than the FIG. 54 high arched foot, so the 20 degree lateral tilt footprint 17 is farther to the outside of upright footprint 37. In addition, the low arched foot pronates inward to inner footprint borders 18; the hatched area 19 is the increased area of the footprint due to the pronation, whereas the hatched area 16 is the decreased area due to pronation.

In FIG. 57, the lateral stability sipe 11 is clearly located on the shoe sole along the inner margin of the lateral footprint 17 superimposed on top of the shoe sole and is straight to maximize ease of flexibility. The basic FIG. 57 design can of course also be used without the lateral stability sipe 11.

A shoe sole of extreme width is necessitated by the common foot tendency toward excessive pronation, as shown in FIG. 57, in order to provide structural support for the full range of natural foot motion, including both pronation and supination. Extremely wide shoe soles are most practical if the sides of the shoe sole are not flat as is conventional but rather are bent up to conform to the natural shape of the shoe wearer's foot sole.

FIGS. 58A–58D shows the use of flexible and relatively inelastic fiber in the form of strands, woven or unwoven (such as pressed sheets), embedded in midsole and bottom sole material. Optimally, the fiber strands parallel (at least roughly) the plane surface of the wearer's foot sole in the naturally rounded design in FIGS. 58A–58C and parallel the flat ground in FIG. 58D, which shows a section of conventional, non-rounded shoe sole. Fiber orientations at an angle to this parallel position will still provide improvement over conventional soles without fiber reinforcement, particularly if the angle is relatively small; however, very large angles or omni-directionality of the fibers will result in increased rigidity or increased softness.

Figure 58A:
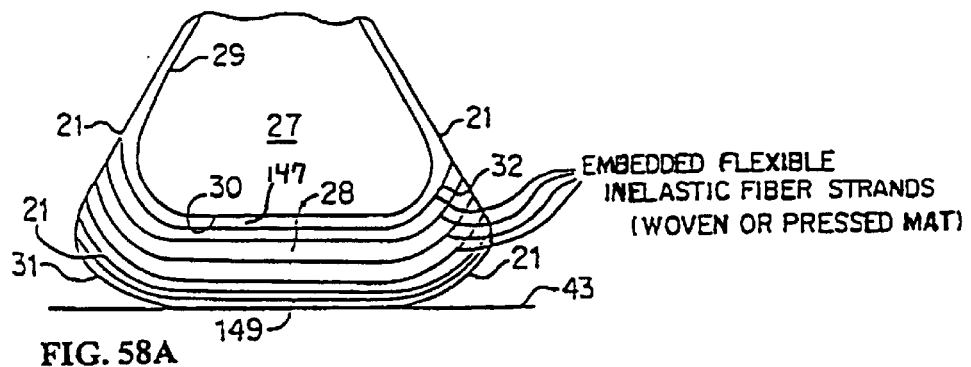
FIG. 58A–D show the use of flexible and relatively inelastic fiber in the form of strands, woven or unwoven (such as pressed sheets), embedded in midsole and bottom sole material.
Figure 58B:
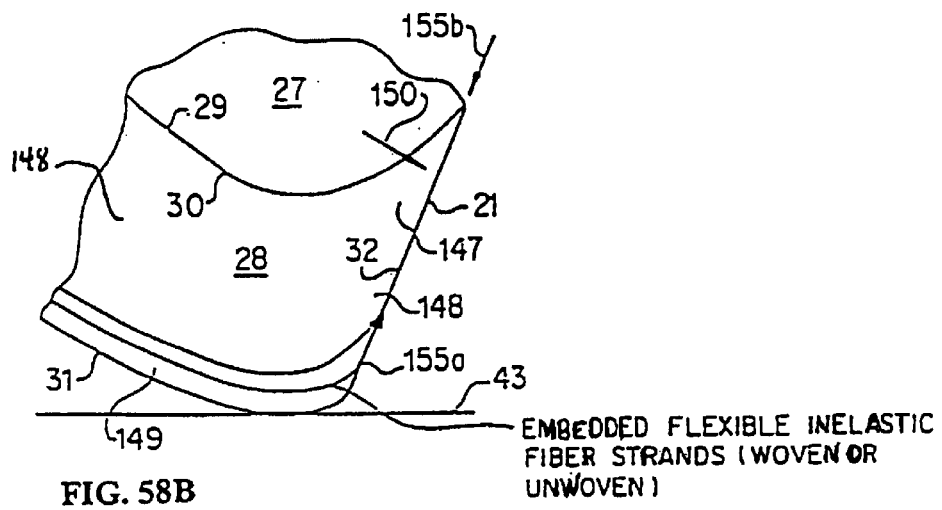
Figure 58C:
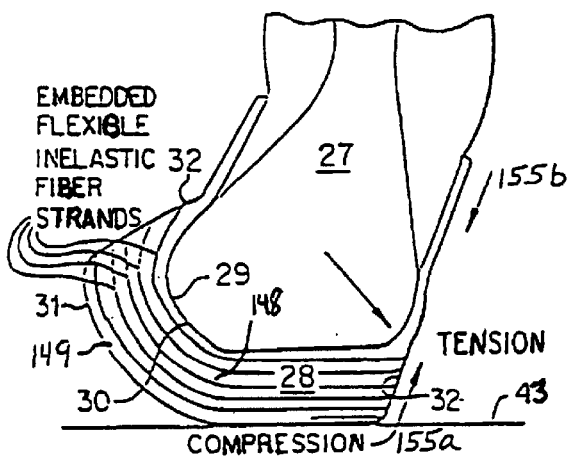
Figure 58D:
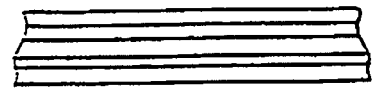

This preferred orientation of the fiber strands, parallel to the plane of the wearer's foot sole, allows for the shoe sole to deform to flatten in parallel with the natural flattening of the foot sole under pressure. At the same time, the tensile strength of the fibers resist the downward pressure of body weight that would normally squeeze the shoe sole material to the sides, so that the side walls of the shoe sole will not bulge out (or will do so less so). The result is a shoe sole material that is both flexible and firm. This unique combination of functional traits is in marked contrast to conventional shoe sole materials in which increased flexibility unavoidably causes increased softness and increased firmness also increases rigidity. FIG. 58A is a modification of FIG. 5A, FIG. 58B is FIG. 6 modified and FIG. 58C is FIG. 7 modified. The position of the fibers shown would be the same even if the shoe sole material is made of one uniform material or of other layers than those shown here.

The use of the fiber strands, particularly when woven, provides protection against penetration by sharp objects, much like the fiber in radial automobile tires. The fiber can be of any size, either individually or in combination to form strands; and of any material with the properties of relative inelasticity (to resist tension forces) and flexibility. The strands of fiber can be short or long, continuous or discontinuous. The fibers facilitate the capability of any shoe sole using them to be flexible but hard under pressure, like the foot sole.

It should also be noted that the fibers used in both the cover of insoles and the Dellinger Web is knit or loosely braided rather than woven, which is not preferred, since such fiber strands are designed to stretch under tensile pressure so that their ability to resist sideways deformation would be greatly reduced compared to non-knit fiber strands that are individually (or in twisted groups of yarn) woven or pressed into sheets.

Figure 59A:
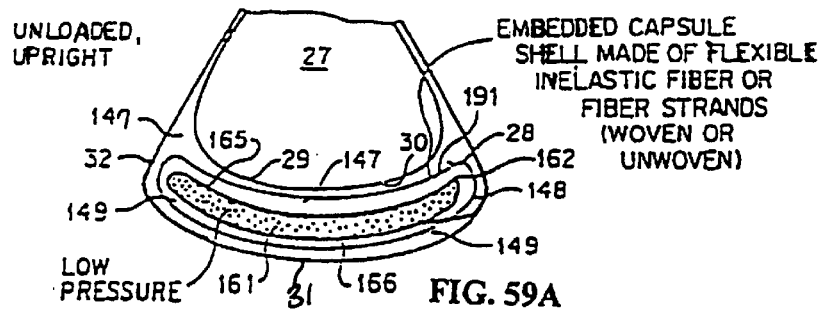
FIG. 59A–D show the use of flexible inelastic fiber or fiber strands, woven or unwoven (such as pressed) to make an embedded capsule shell that surrounds the cushioning compartment 161 containing a pressure-transmitting medium like gas, gel, or liquid.
Figure 59B:
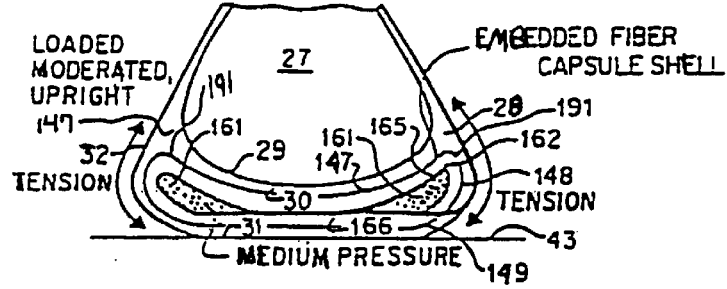
Figure 59C:
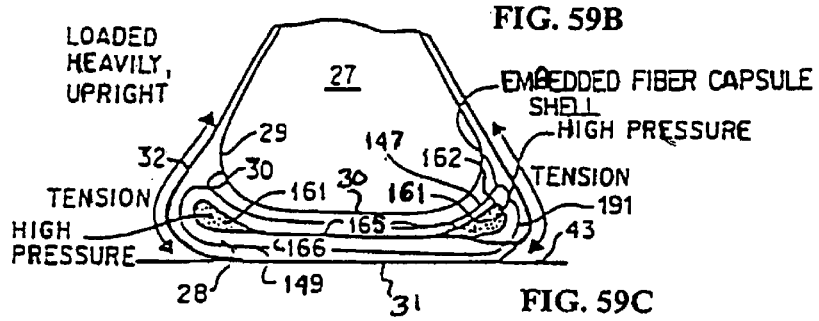
Figure 59D:
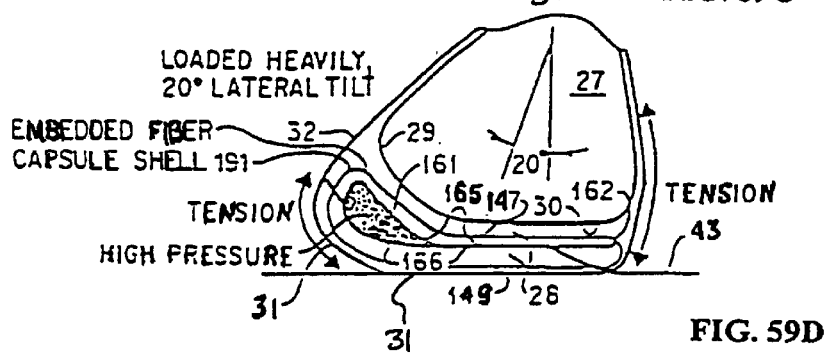
Figure 59E:
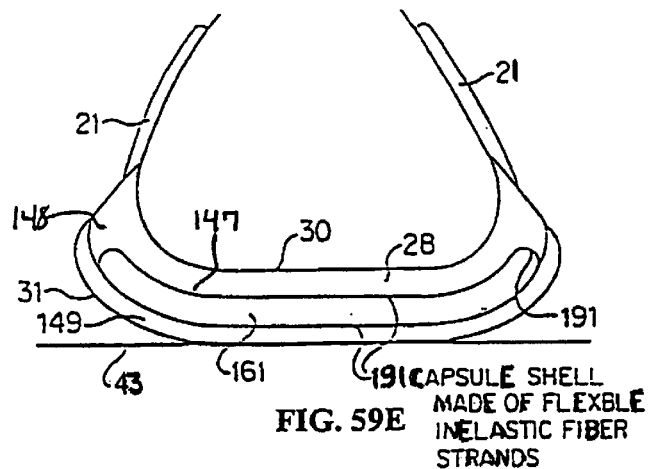

FIGS. 59A–59D are FIGS. 9A–D modified to show the use of flexible inelastic fiber or fiber strands, woven or unwoven (such as pressed) to make an embedded capsule shell that surrounds the cushioning compartment 161 containing a pressure-transmitting medium like gas, gel, or liquid. The fibrous capsule shell could also directly envelope the surface of the cushioning compartment, which is easier to construct, especially during assembly. FIG. 59E is a figure showing a fibrous capsule shell 191 that directly envelopes the surface of a cushioning compartment 161; the shoe sole structure is not fully rounded, like FIG. 59A, but naturally rounded, and has a flat middle portion corresponding to the flattened portion of a wearer's load-bearing foot sole.

Figure 59F:
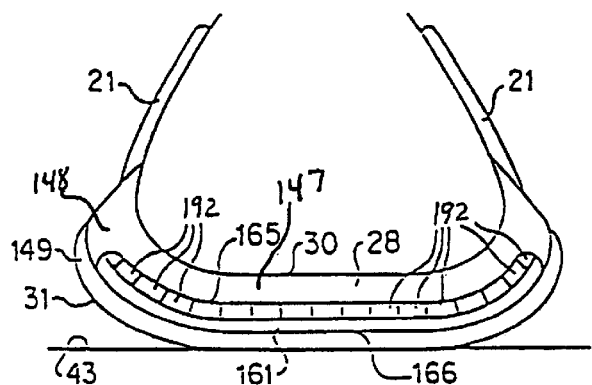

FIG. 59F shows a unique combination of the FIGS. 9 & 10 design above. The upper surface 165 and lower surface 166 contain the cushioning compartment 161, which is subdivided into two parts. The lower half of the cushioning compartment 161 is both structured and functions like the compartment shown in FIG. 9 above. The upper half is similar to FIG. 10 above but subdivided into chambers 192 that are more geometrically regular so that construction is simpler; the structure of the chambers 192 can be of honeycombed in structure. The advantage of this design is that it copies more closely than the FIG. 9 design the actual structure of the wearer's foot sole, while being much more simple to construct than the FIG. 10 design. Like the wearer's foot sole, the FIG. 59F design would be relative soft and flexible in the lower half of the chamber 161, but firmer and more protective in the upper half, where the mini-chambers 192 would stiffen quickly under load-bearing pressure. Other multi-level arrangements are also possible.

Figure 60A:
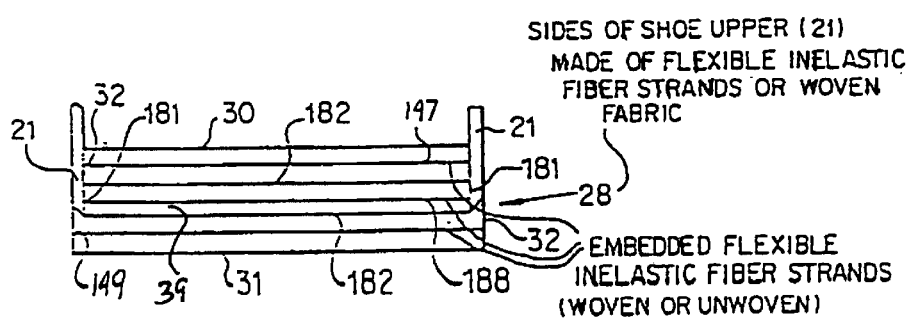
FIG. 60A–D show the use of embedded flexible inelastic fiber or fiber strands, woven or unwoven, in various embodiments similar those shown in FIGS. 58A–D.
Figure 60B:
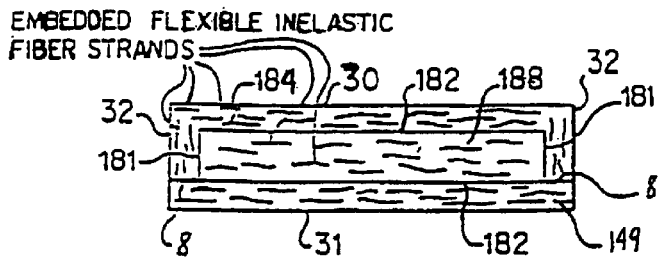
Figure 60C:
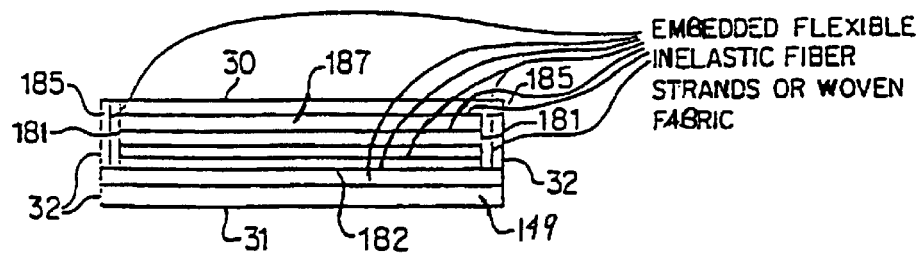
Figure 60D:
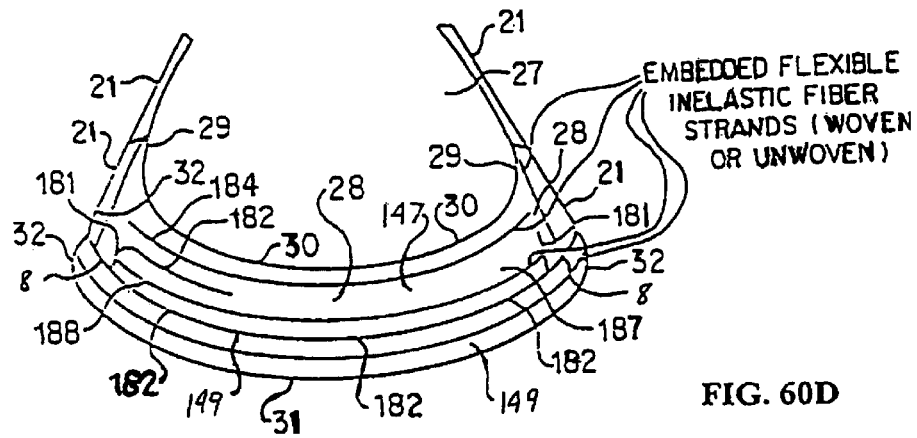
Figure 60E:
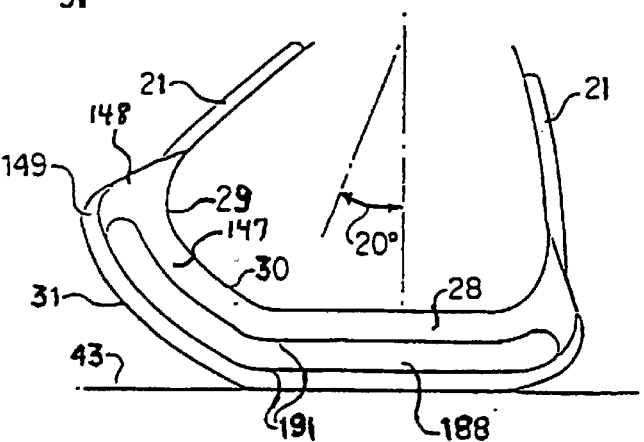
FIG. 60E shows a frontal plane cross section of a fibrous capsule shell 191 that directly envelops the surface of the insertable midsole orthotic 145.

FIGS. 60A–60D show the use of embedded flexible inelastic fiber or fiber strands, woven or unwoven, in various embodiments similar those shown in FIGS. 58A–58D. FIG. 60E is a figure showing a frontal plane cross section of a fibrous capsule shell 191 that directly envelopes the surface of the midsole section 188.

FIG. 61C compares the footprint made by a conventional shoe 35 with the relative positions of the wearer's right foot sole in the maximum supination position 37*a* and the maximum pronation position 37*b*. FIG. 61C reinforces the indication that more relative sideways motion occurs in the forefoot and midtarsal areas, than in the heel area.

As shown in FIG. 61C, at the extreme limit of supination and pronation foot motion, the base of the calcaneus 109 and the lateral calcaneal tuberosity 108 roll slightly off the sides of the shoe sole outer boundary 35. However, at the same extreme limit of supination, the base of the fifth metatarsal 97 and the head of the fifth metatarsal 94 and the fifth distal phalange 93 all have rolled completely off the outer boundary 35 of the shoe sole.

FIG. 61D shows an overhead perspective of the actual bone structures of the foot.

Figure 62:
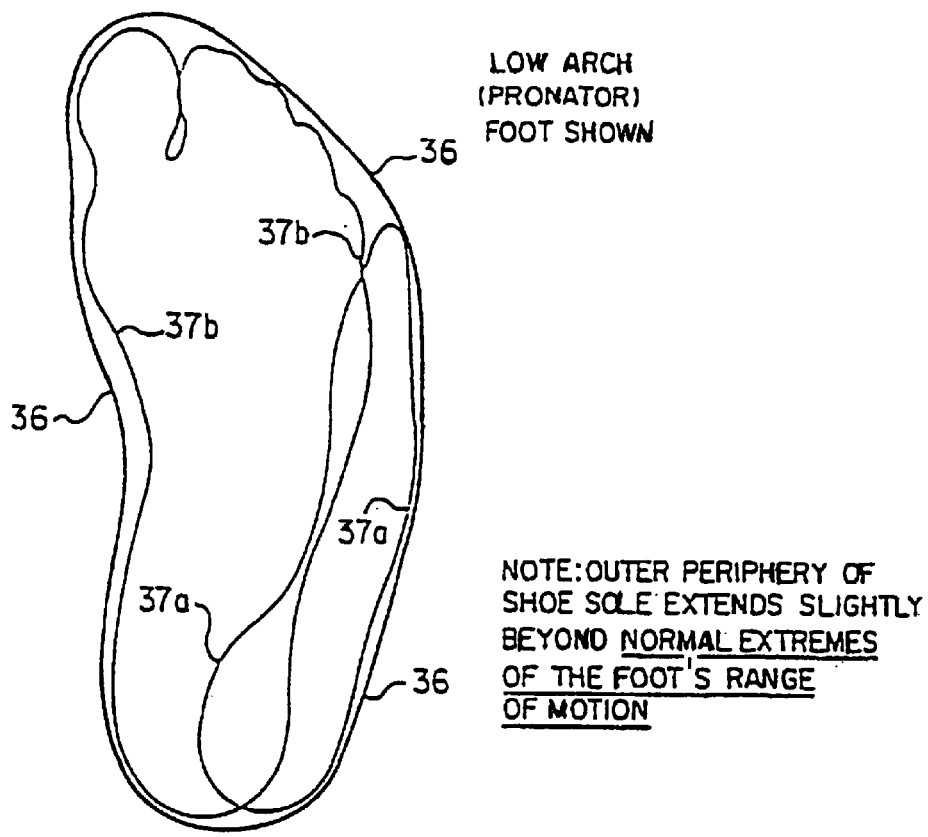
FIG. 62 shows a similar structure to FIG. 61, but with only the section under the forefoot 126 unglued or not firmly attached, the rest of the bottom sole 149 (or most of it) would be glued or firmly attached.

FIG. 62 is similar to FIG. 57 above, in that it shows a shoe sole that covers the full range of motion of the wearer's right foot sole, with or without a sipe 11. However, while covering that full range of motion, it is possible to abbreviate the rounded sides of the shoe sole to only the essential structural and propulsion elements of the foot sole, as previously discussed herein.

Figure 63:
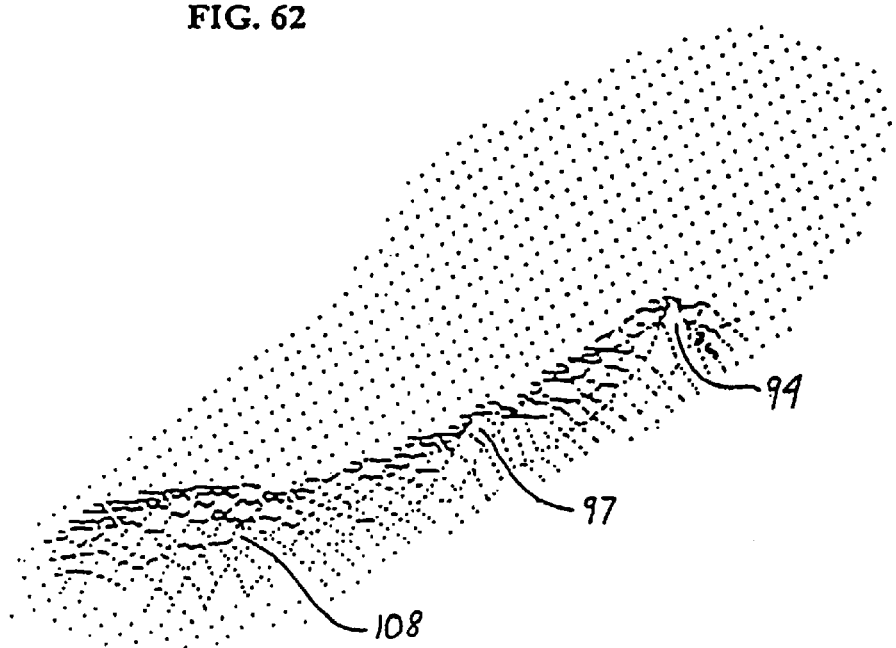
FIG. 63C compares the footprint made by a conventional shoe 35 with the relative positions of the wearer's right foot sole in the maximum supination position 37a and the maximum pronation position 37b.
FIG. 63D shows an overhead perspective of the actual bone structures of the foot that are indicated in FIG. 63C.

FIG. 63 shows an electronic image of the relative forces present at the different areas of the bare foot sole when at the maximum supination position shown as 37*a* in FIG. 62 above; the forces were measured during a standing simulation of the most common ankle spraining position. The maximum force was focused at the head of the fifth metatarsal and the second highest force was focused at the base of the fifth metatarsal. Forces in the heel area were substantially less overall and less focused at any specific point.

FIG. 63 indicates that, among the essential structural support and propulsion elements shown in FIG. 40 above, there are relative degrees of importance. In terms of preventing ankle sprains, the most common athletic injury (about two-thirds occur in the extreme supination position 37*a* shown in FIG. 62), FIG. 63 indicates that the head of the fifth metatarsal 94 is the most critical single area that must be supported by a shoe sole in order to maintain the shoe sole, when measured in frontal or transverse plane cross sections; that lower surface of the Theoretically Ideal Stability Plane 51 becomes load-bearing in contact with the ground during foot inversion and eversion, which is normal sideways or lateral motion.

Although the inventions described in this application may in some instances be less than optimal, they nonetheless distinguish over all prior art and still do provide a significant stability improvement over existing footwear and thus provide significantly increased injury prevention benefit compared to existing footwear.

Figure 65:
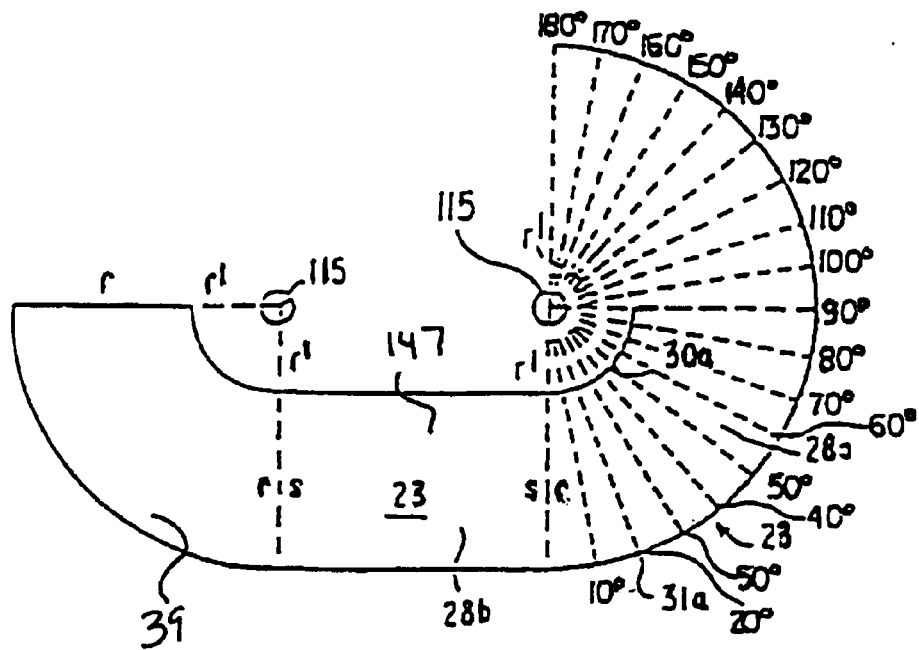
FIG. 65 indicates the angular measurements of the rounded shoe sole sides from zero degrees to 180 degrees.
Figure 66A:
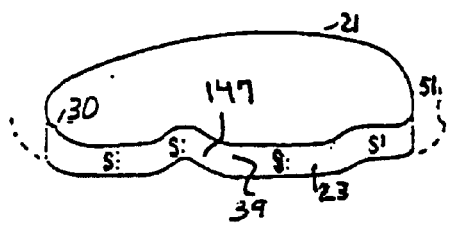
FIG. 66 shows a shoe sole without rounded stability sides.
Figure 66B:
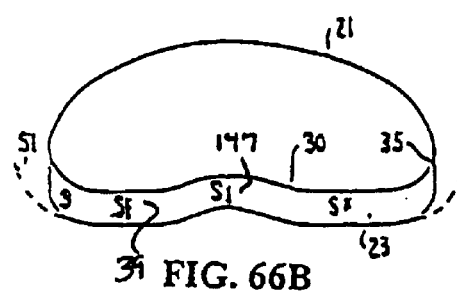
Figure 66C:
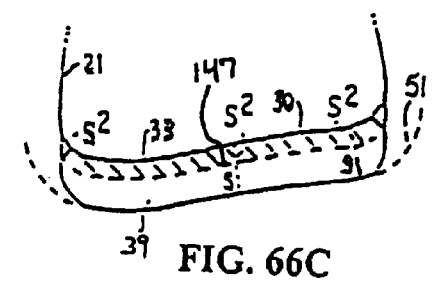
Figure 66D:
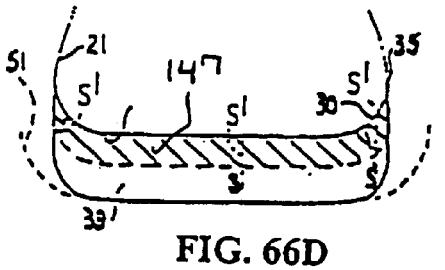
Figure 66F:
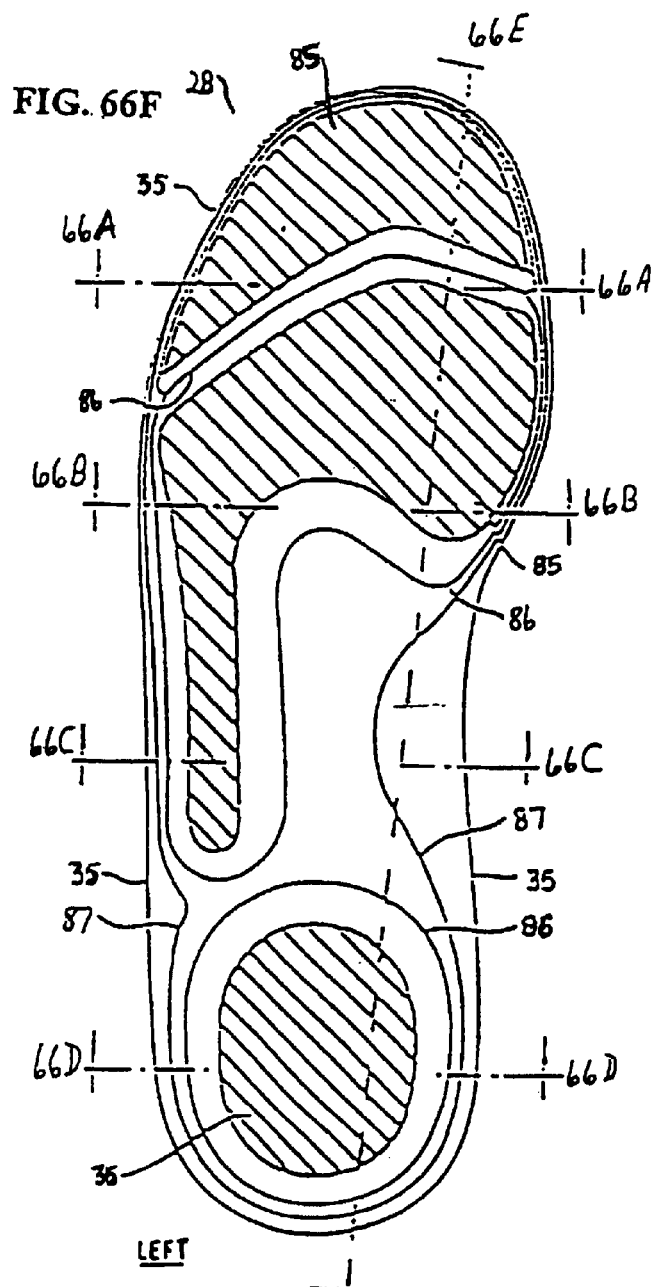
Figure 66E:
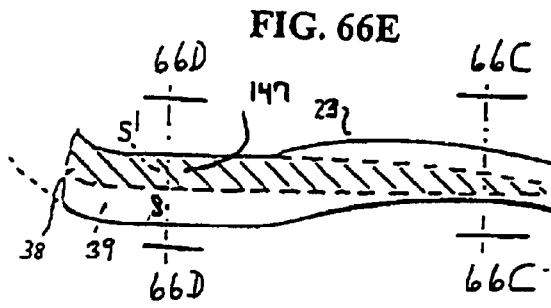

FIG. 65 provides a means to measure the rounded shoe sole sides incorporated in the applicant's inventions described above. FIG. 65 correlates the height or extent of the rounded side portions of the shoe sole with a precise angular measurement from zero to 180 degrees. That angular measurement corresponds roughly with the support for sideways tilting provided by the rounded shoe sole sides of any angular amount from zero degrees to 180 degrees, at least for such rounded sides proximate to any one or more or all of the essential stability or propulsion structures of the foot, as defined above. The rounded shoe sole sides as described in this application can have any angular measurement from zero degrees to 180 degrees.

FIGS. 66A–66F, FIG. 67A–67E and FIG. 68 describe shoe sole structural inventions that are formed with an upper surface to conform, or at least be complementary, to the all or most or at least part of the shape of the wearer's foot sole, whether under a body weight load or unloaded, but without rounded stability barefoot-like lateral stability. FIG. 63 indicates that the base of the fifth metatarsal 97 is very close to being as important. Generally, the base and the head of the fifth metatarsal are completely unsupported by a conventional shoe sole.

Figure 64:
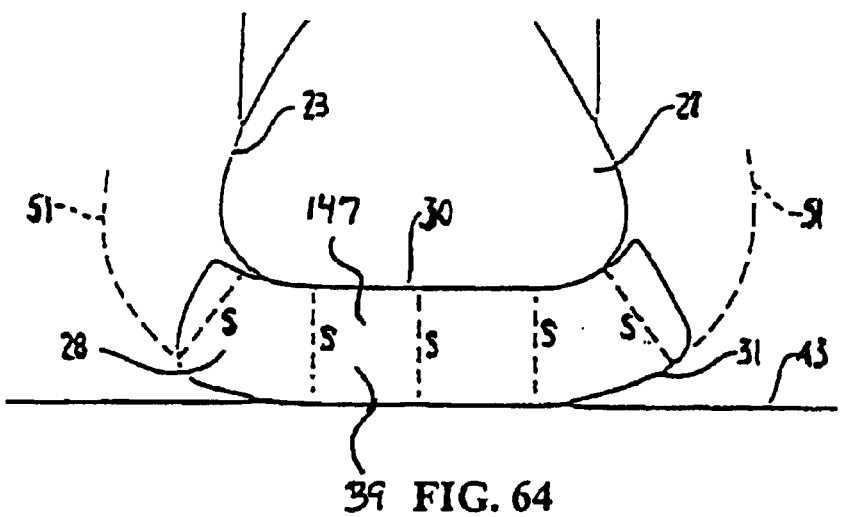
FIG. 64 shows on the right side an upper shoe sole surface of the rounded side that is complementary to the shape of the wearer's foot sole; on the left side

FIGS. 64A–64B demonstrate a variation in the Theoretically Ideal Stability Plane 51. In previously described embodiments, the inner surface of the Theoretically Ideal Stability Plane 51 conforms to the shape of the wearer's foot, especially its sides, so that the inner surface of the applicant's shoe sole invention conforms to the outer surface of the wearer's foot sole, especially it sides, when measured in frontal plane or transverse plane cross sections. For illustration purposes, the right side of FIG. 64 explicitly illustrates such an embodiment.

The right side of FIG. 64 includes an upper shoe sole surface that is complementary to the shape of all or a portion the wearer's foot sole. In addition, this application describes shoe rounded sole side designs wherein the inner surface of the Theoretically Ideal Stability Plane 51 lies at some point between conforming or complementary to the shape of the wearer's foot sole, that is—roughly paralleling the foot sole including its side—and paralleling the flat ground; that inner surface of the Theoretically Ideal Stability Plane 51 becomes load-bearing in contact with the foot sole during foot inversion and eversion, which is normal sideways or lateral motion.

Again, for illustration purposes, the left side of FIG. 64B describes shoe sole side designs wherein the lower surface of the Theoretically Ideal Stability Plane 51, which equates to the load-bearing surface of the bottom or outer shoe sole, of the shoe sole side portions is above the plane of the underneath portion of sides as defined by the applicant. As such, FIGS. 66–68 are similar to FIGS. 38–40 above, but without the rounded stability sides at the essential structural support and propulsion elements, which are the base and lateral tuberosity of the calcaneus, the heads of the first and fifth metatarsals, the base of the fifth metatarsal, and the first distal phalange, and with shoe sole rounded side thickness variations, as measured in frontal plane cross sections as defined in this and earlier applications.

FIGS. 66A–66F, FIG. 67A–67E, and FIG. 68, like the many other variations of the applicant's naturally rounded design described in this application, show a shoe sole invention wherein both the upper, foot sole-contacting surface of the shoe sole and the bottom, ground-contacting surface of the shoe sole mirror the contours of the bottom surface of the wearer's foot sole, forming in effect a flexible three dimensional mirror of the load-bearing portions of that foot sole when bare.

The shoe sole shown in FIGS. 66–68 preferably include an insole layer, a midsole layer, and bottom sole layer, and variation in the thickness of the shoe sole, as measured in sagittal plane cross sections, like the heel lift common to most shoes, as well as a shoe upper.

FIG. 69A–69D shows the implications of relative difference in range of motions between forefoot, midtarsal, and heel areas. FIG. 69A–D is a modification of FIG. 33 above, with the left side of the figures showing the required range of motion for each area.

Figure 69A:
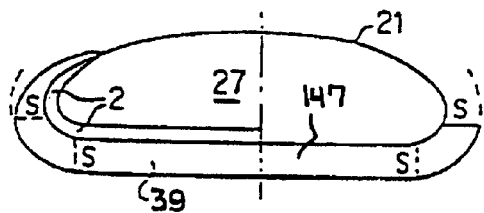

FIG. 69A shows a cross section of the forefoot area and therefore on the left side shows the highest rounded sides (compared to the thickness of the shoe sole in the forefoot area) to accommodate the greater forefoot range of motion. The rounded side is sufficiently high to support the entire range of motion of the wearer's foot sole. Note that the sock liner or insole 2 is shown.

Figure 69B:
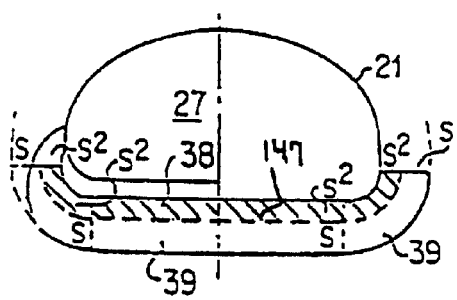
Figure 69C:
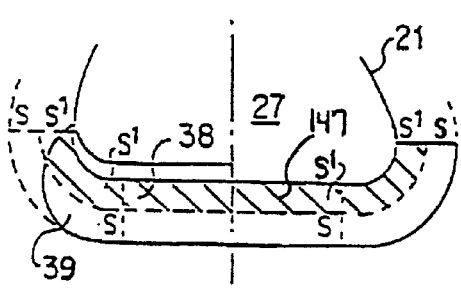
Figure 69D:
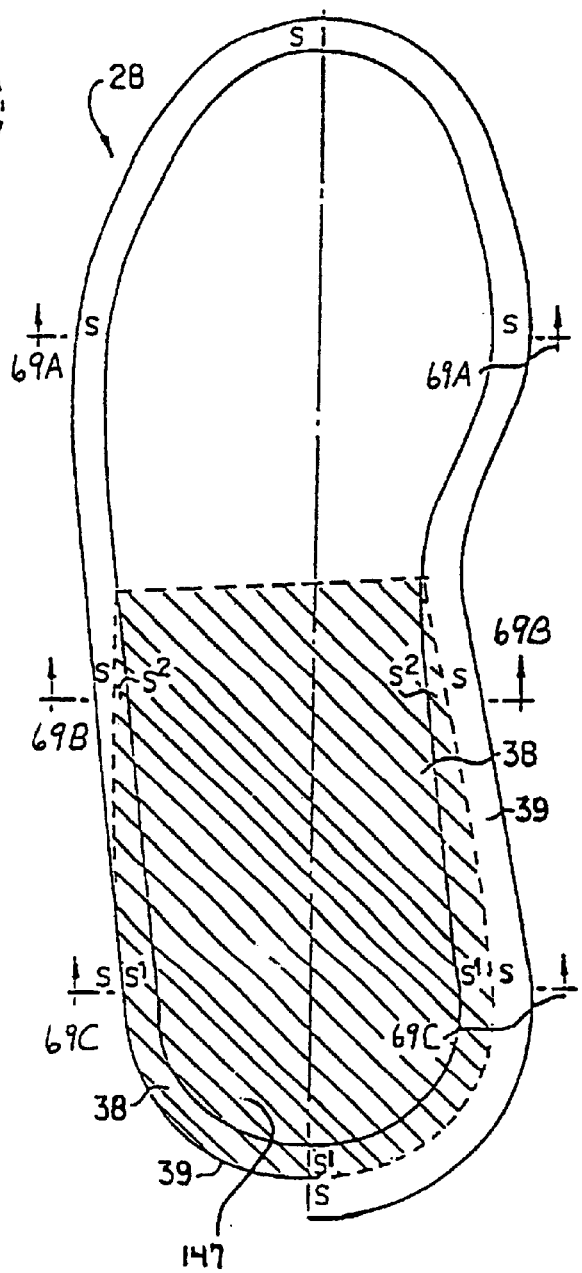

FIG. 69B shows a cross section of the midtarsal area at about the base of the fifth metatarsal, which has somewhat less range of motion and therefore the rounded sides are not as high (compared to the thickness of the shoe sole at the midtarsal). FIG. 69C shows a cross section of the heel area, where the range of motion is the least, so the height of the rounded sides is relatively least of the three general areas (when compared to the thickness of the shoe sole in the heel area).

Each of the three general areas, forefoot, midtarsal and heel, have rounded sides that differ relative to the high of those sides compared to the thickness of the shoe sole in the same area. At the same time, note that the absolute height of the rounded sides is about the same for all three areas and the contours have a similar outward appearance, even though the actual structure differences are quite significant as shown in cross section.

In addition, the rounded sides shown in FIG. 69A–D can be abbreviated to support only those essential structural support and propulsion elements identified in FIG. 40 above. The essential structural support elements are the base and lateral tuberosity of the calcaneus 95, the heads of the metatarsals 96, and the base of the fifth metatarsal 97. The essential propulsion element is the head of the first distal phalange 98.

Figure 70:
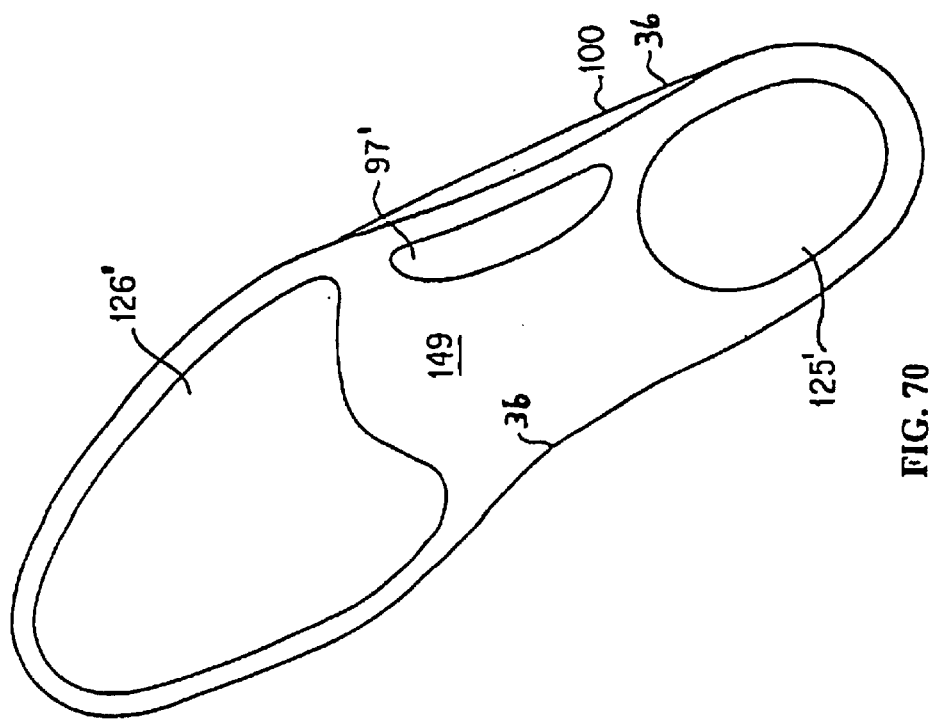
FIG. 70 shows an invention for a shoe sole that covers the full range of motion of the wearer's right foot sole.

FIG. 70 shows a similar view of a bottom sole structure 149, but with no side sections. The areas under the forefoot 126, heel 125, and base of the fifth metatarsal 97 would not be glued or attached firmly, while the other area (or most of it) would be glued or firmly attached. FIG. 70 also shows a modification of the outer periphery of the convention shoe sole 36: the typical indentation at the base of the fifth metatarsal is removed, replaced by a fairly straight line 100.

Figure 71:
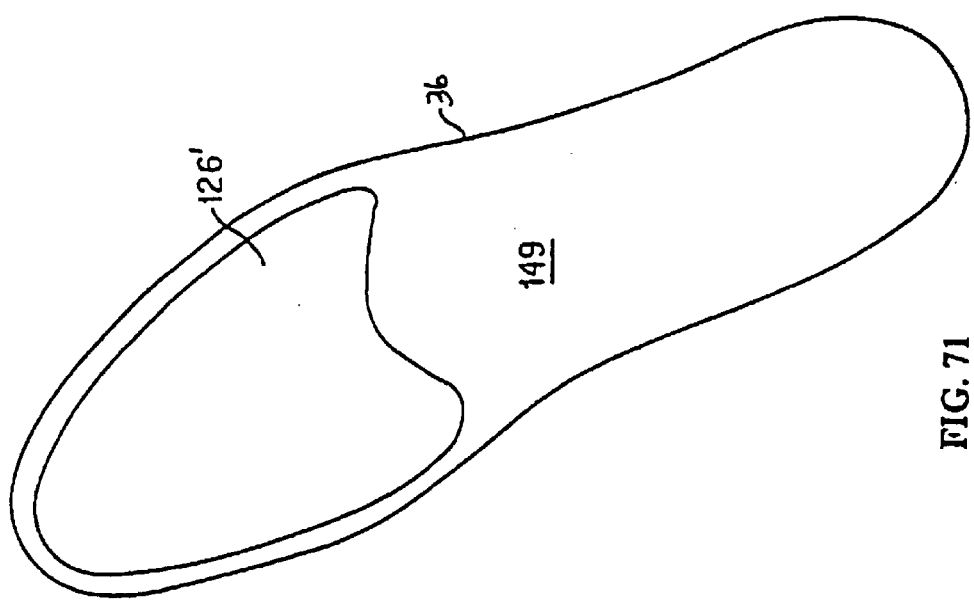
FIG. 71 shows an electronic image of the relative forces present at the different areas of the bare foot sole when at the maximum supination position shown as 37a in FIG. 62; the forces were measured during a standing simulation of the most common ankle spraining position.

FIG. 71 shows a similar structure to FIG. 70, but with only the section under the forefoot 126 unglued or not firmly attached; the rest of the bottom sole 149 (or most of it) would be glued or firmly attached.

Figure 72H:
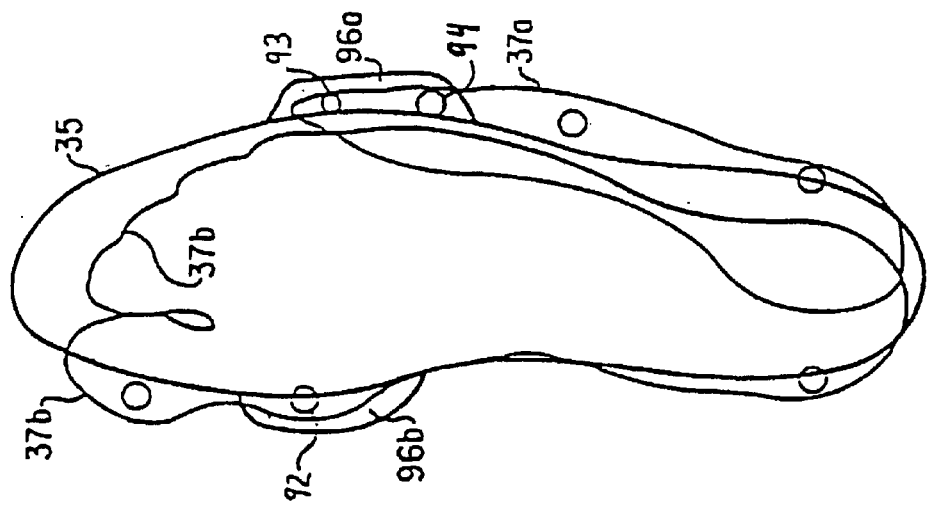
FIGS. 72G–H show shoe soles with only one or more of the essential stability elements, but which, based on FIG. 71, still represent major stability improvements over existing footwear. All omit changes in the heel area.
Figure 72G:
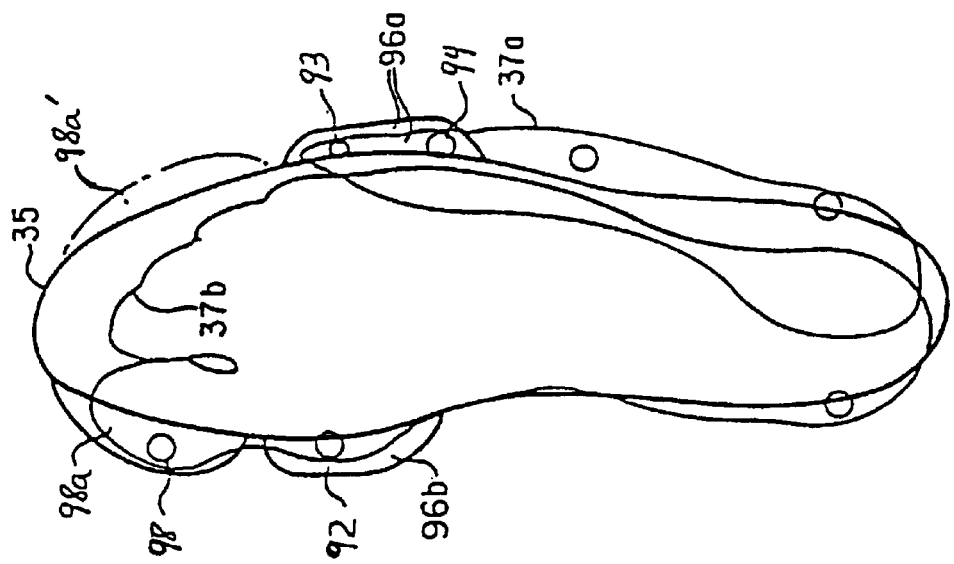

FIGS. 72G–72H show shoe soles with only one or more, but not all, of the essential stability elements (the use of all of which is still preferred) but which, based on FIG. 63, still represent major stability improvements over existing footwear. This approach of abbreviating structural support to a few elements has the economic advantage of being capable of construction using conventional flat sheets of shoe sole material, since the individual elements can be bent up to the rounded of the wearer's foot with reasonable accuracy and without difficulty. Whereas a continuous naturally rounded side that extends all of, or even a significant portion of, the way around the wearer's foot sole would buckle partially since a flat surface cannot be accurately fitted to a rounded surface; hence, injection molding is required for accuracy.

The features of FIGS. 72G–72H can be used in combination with the designs shown in this application. Further, various combinations of abbreviated structural support elements may be utilized other than those specifically illustrated in the figures.

FIG. 72G shows a shoe sole combining the additional stability corrections 96a, 96b, and 98a supporting the first and fifth metatarsal heads and distal phalange heads. The dashed line 98a' represents a symmetrical optional stability addition on the lateral side for the heads of the second through fifth distal phalanges, which are less important for stability.

FIG. 72H shows a shoe sole with symmetrical stability additions 96a and 96b. Besides being a major improvement in stability over existing footwear, this design is aesthetically pleasing and could even be used with high heel type shoes, especially those for women, but also any other form of footwear where there is a desire to retain relatively conventional looks or where the shear height of the heel or heel lift precludes stability side corrections at the heel or the base of the fifth metatarsal because of the required extreme thickness of the sides. This approach can also be used where it is desirable to leave the heel area conventional, since providing both firmness and flexibility in the heel is more difficult that in other areas of the shoe sole since the shoe sole thickness is usually much greater there; consequently, it is easier, less expensive in terms of change, and less of a risk in departing from well understood prior art just to provide additional stability corrections to the forefoot and/or base of the fifth metatarsal area only.

Since the shoe sole thickness of the forefoot can be kept relatively thin, even with very high heels, the additional stability corrections can be kept relatively inconspicuous. They can even be extended beyond the load-bearing range of motion of the wearer's foot sole, even to wrap all the way around the upper portion of the foot in a strictly ornamental way (although they can also play a part in the shoe upper's structure), as a modification of the strap, for example, often seen on conventional loafers.

FIGS. 73A–73D show close-up cross sections of shoe soles modified with the applicant's inventions for deformation sipes.

Figure 73A:
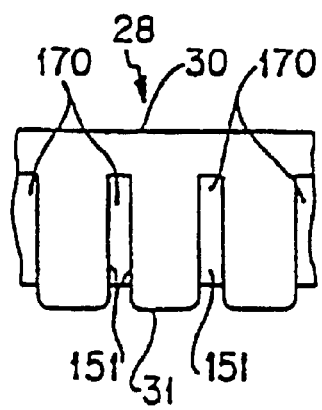
FIGS. 73A–73D show in close-up sections of the shoe sole various new forms of sipes, including both slits and channels.
Figure 73B:
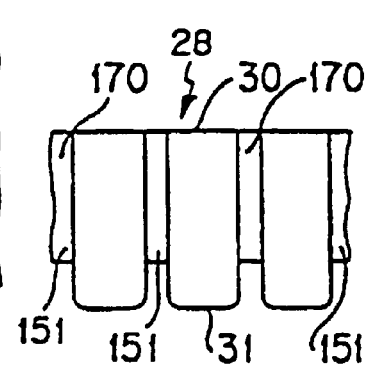

FIG. 73A shows a cross section of a design with deformation sipes in the form of channels, but with most of the channels filled with a material 170 flexible enough that it still allows the shoe sole to deform like the human foot. FIG. 73B shows a similar cross section with the channel sipes extending completely through the shoe sole, but with the intervening spaces also filled with a flexible material 170 like FIG. 73A; a flexible connecting top layer 123 can also be used, but is not shown. The relative size and shape of the sipes can vary almost infinitely. The relative proportion of flexible material 170 can vary, filling all or nearly all of the sipes, or only a small portion, and can vary between sipes in a consistent or even random pattern. As before, the exact structure of the sipes and filler material 170 can vary widely and still provide the same benefit, though some variations will be more effective than others. Besides the flexible connecting utility of the filler material 170, it also serves to keep out pebbles and other debris that can be caught in the sipes, allowing relatively normal bottom sole tread patterns to be created.

Figure 73C:
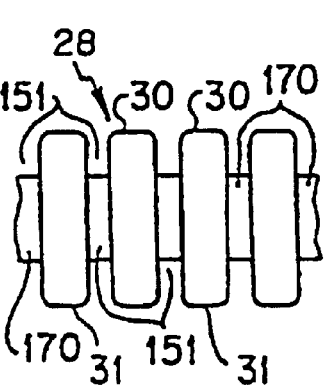
Figure 73D:
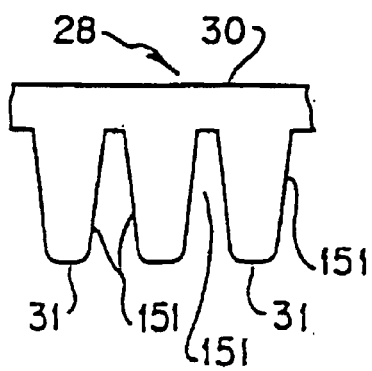

FIG. 73C shows a similar cross section of a design with deformation sipes in the form of channels that penetrate the shoe sole completely and are connected by a flexible material 170 which does not reach the upper surface 30 of the shoe sole 28. Such an approach creates can create and upper shoe sole surface similar to that of the trademarked Maseur® sandals, but one where the relative positions of the various sections of the upper surface of the shoe sole will vary between each other as the shoe sole bends up or down to conform to the natural deformation of the foot. The shape of the channels should be such that the resultant shape of the shoe sole sections would be similar but rounder than those honeycombed shapes of FIG. 14D of the '509 application; in fact, like the Maseur sandals, cylindrical with a rounded or beveled upper surface is probably optimal. The relative position of the flexible connecting material 170 can vary widely and still provide the essential benefit. Preferably, the attachment of the shoe uppers would be to the upper surface of the flexible connecting material 170.

A benefit of the FIG. 73C design is that the resulting upper surface 30 of the shoe sole can change relative to the surface of the foot sole due to natural deformation during normal foot motion. The relative motion makes practical the direct contact between shoe sole and foot sole without intervening insoles or socks, even in an athletic shoe. This constant motion between the two surfaces allows the upper surface of the shoe sole to be roughened to stimulate the development of tough calluses (called a "Seri boot"), as described at the end of FIG. 10 above, without creating points of irritation from constant, unrelieved rubbing of exactly the same corresponding shoe sole and foot sole points of contact.

FIG. 73C shows a similar cross section of a design with deformation sipes in the form of angled channels in roughly and inverted V shape. Such a structure allows deformation bending freely both up and down; in contrast deformation slits can only be bent up and channels with parallel side walls 151 generally offer only a limited range of downward motion. The FIG. 73D angled channels would be particularly useful in the forefoot area to allow the shoe sole to conform to the natural rounded of the toes, which curl up and then down. As before, the exact structure of the angle channels can vary widely and still provide the same benefit, though some variations will be more effective than others. Finally, though not shown, deformation slits can be aligned above deformation channels, in a sense continuing the channel in circumscribed form.

FIG. 74 shows sagittal plane shoe sole thickness variations, such as heel lifts 38 and forefoot lifts 40, and how the rounded sides 28a equal and therefore vary with those varying thicknesses, as discussed in connection with FIG. 31.

FIG. 75 shows, in FIGS. 75A–75C a method, known from the prior art, for assembling the midsole shoe sole structure of the present invention, showing in FIG. 75C the general concept of inserting the insertable midsole orthotic 145 into the shoe upper and sole combination in the same very simple manner as an intended wearer inserts his foot into the shoe upper and sole combination. FIGS. 75A and 75B show a similar insertion method for the bottom sole 149.

The combinations of the many elements the applicant's invention introduced in the preceding figures are shown because those embodiments are considered to be at least among the most useful. However, many other useful combinations embodiments are also clearly possible, but cannot be shown simply because of the impossibility of showing them all while maintaining a reasonable brevity and conciseness in what is already an unavoidably long description due to the inherently highly interconnected nature of the inventions shown herein, each of which can operate independently or as part of a combination of others.

Therefore, any combination that is not explicitly described above is implicit in the overall invention of this application and, consequently, any part of any of the preceding FIGS. 1–75 and/or textual specification can be combined with any other part of any one or more other of the FIGS. 1–75 and/or textual specification of this application to make new and useful improvements over the existing art.

In addition, any unique new part of any of the preceding FIGS. 1–73 and/or associated textual specification can be considered by itself alone as an individual improvement over the existing art.

The foregoing shoe designs meet the objectives of this invention as stated above. However, it will clearly be understood by those skilled in the art that the foregoing description has been made in terms of the preferred embodiments and various changes and modifications may be made without departing from the scope of the present invention which is to be defined by the appended claims.

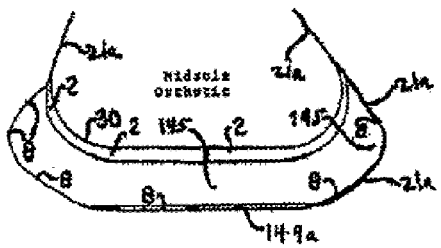

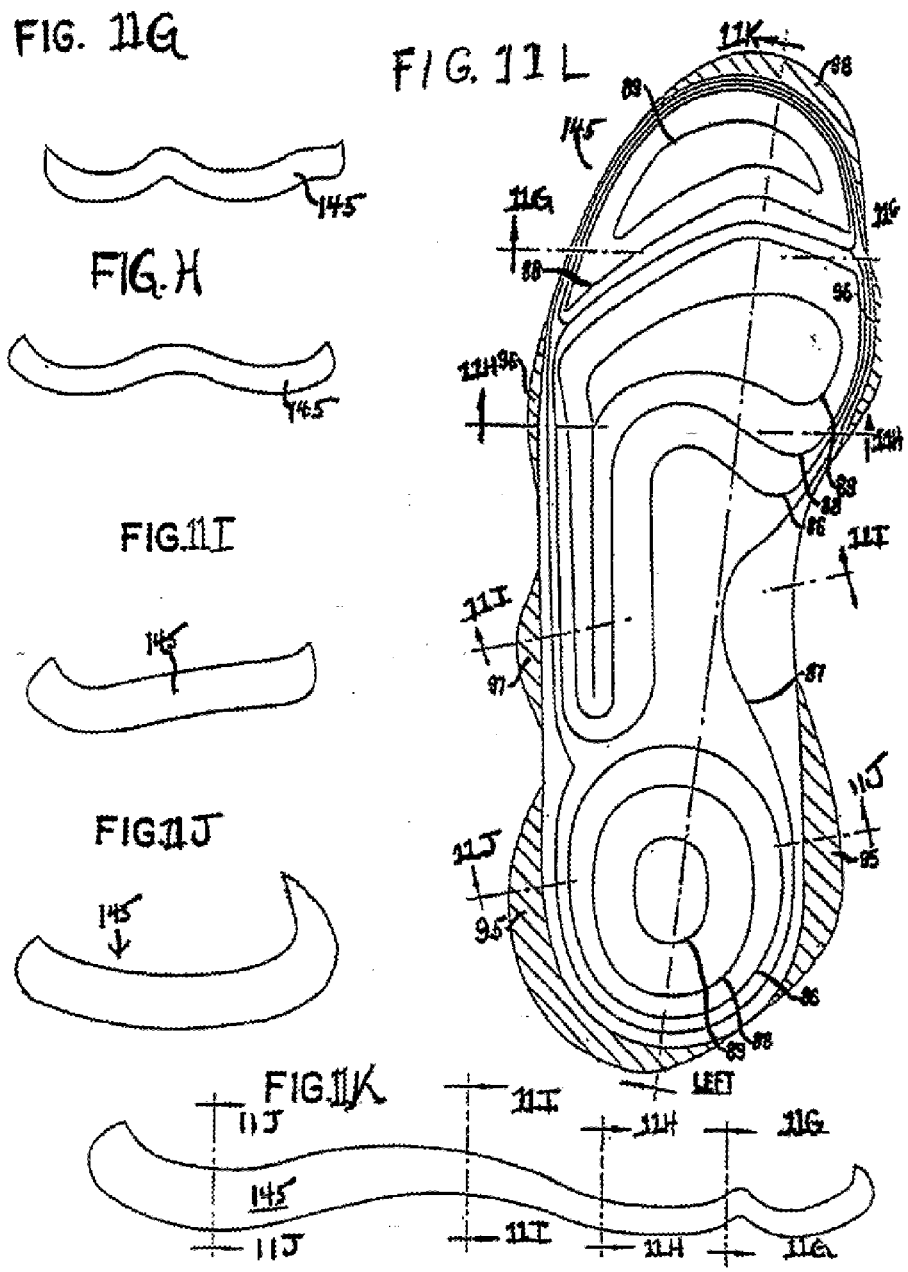

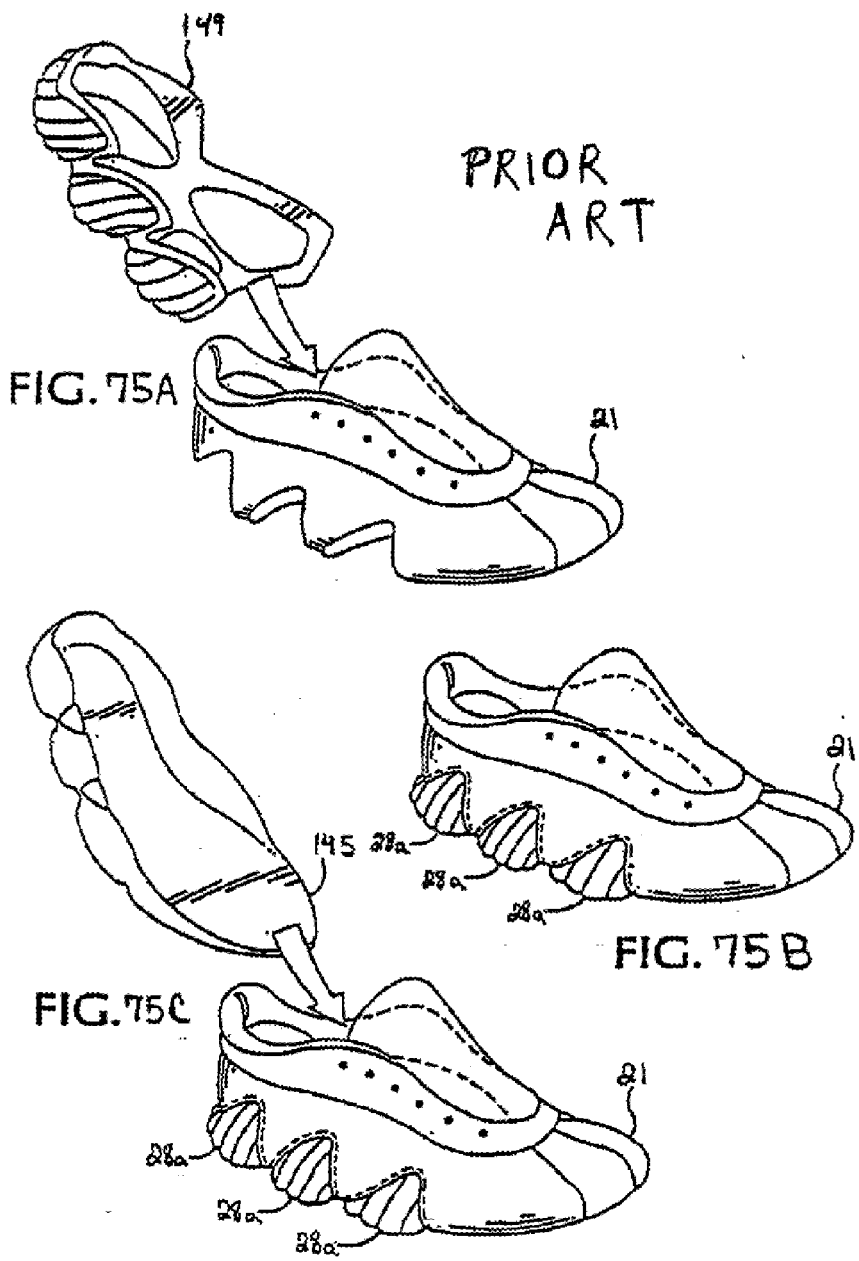

What is claimed is:

1. An orthotic inner shoe which comprises:
    an insertable midsole orthotic sized to fit inside and form part of the sole of a shoe designed to receive and retain said insertable midsole orthotic;
    a secondary outer sole on at least a portion of the outer surface of the insertable midsole orthotic to provide traction or wear resistance when said orthotic inner shoe is worn without the shoe designed to receive and retain said insertable midsole orthotic;
    a device associated with the insertable midsole orthotic for retaining the orthotic inner shoe on an intended wearer's foot when worn without the shoe designed to receive and retain the insertable midsole orthotic; and
    wherein said orthotic inner shoe is removable from said shoe in order to wear said orthotic inner shoe independently of said shoe.

2. The orthotic inner shoe as claimed in claim 1 wherein the device for retaining the orthotic inner shoe on an intended wearer's foot comprises an integral secondary upper.

3. The orthotic inner shoe as claimed in claim 1, wherein an upper portion of the insertable midsole orthotic provides the corrective orthotic effect and the upper portion of the insertable midsole orthotic comprises less than half of the thickness of the sole of the insertable midsole orthotic.

4. The orthotic inner shoe as claimed in claim 1, further comprising at least one computer controlled compartment, and wherein the computer control for the computer controlled compartment is located in an upper portion of the insertable midsole orthotic and the upper portion of the insertable midsole orthotic comprises less than half of the thickness of the sole of the insertable midsole orthotic.

5. The orthotic inner shoe as claimed in claim 1, wherein at least one portion of an outer surface of a side of the insertable midsole orthotic is concavely rounded relative to an inner section of the insertable midsole orthotic directly adjacent to the concavely rounded outer surface portion, as viewed in a frontal plane cross-section when the insertable midsole orthotic is upright and in an unloaded condition.

6. The orthotic inner shoe as claimed in claim 5, wherein at least one portion of an inner surface of a side of the insertable midsole orthotic is convexly rounded relative to a section of the insertable midsole orthotic directly adjacent to the convexly rounded inner surface portion, as viewed in a frontal plane cross-section when the insertable midsole orthotic is upright and in an unloaded condition.

7. The orthotic inner shoe as claimed in claim 6, wherein each at least one convexly rounded inner surface portion and each at least one concavely rounded outer surface portion is located at a corresponding location on the insertable midsole orthotic to thereby form at least one concavely rounded side portion of the insertable midsole orthotic located between said convexly rounded inner surface portion and the concavely rounded outer surface portion, as viewed in a frontal plane cross-section when the insertable midsole orthotic is upright and in an unloaded condition, said concavity of each said concavely rounded side portion being determined relative to a portion of the insertable midsole orthotic which is adapted to receive the foot of an intended wearer; and said at least one concavely rounded side portion is located at a location on the insertable midsole orthotic which corresponds to the position of at least one of the following parts of an intended wearer's foot when inside the insertable midsole orthotic: a base of a calcaneus, a lateral tuberosity of the calcaneus, a head of a first distal phalange, a longitudinal arch, a head of a first metatarsal, a head of a fifth metatarsal, and a base of the fifth metatarsal.

8. The orthotic inner shoe as claimed in claim 7, wherein a thickness of the insertable midsole orthotic tapers from a greater thickness measured at said at least one concavely rounded side portion to a lesser thickness at a location on one side of said concavely rounded side portion, as viewed in a horizontal plane when the insertable midsole orthotic is upright and in an unloaded condition.

9. The orthotic inner shoe as claimed in claim 8, wherein said thickness of the insertable midsole orthotic tapers to a lesser thickness on both sides of said concavely rounded side portion, as viewed in a horizontal plane when the orthotic inner shoe is upright and in an unloaded condition.

10. The orthotic inner shoe as claimed in claim 7, comprising at least two concavely rounded side portions and an indentation located between said two concavely rounded side portions, as viewed in a horizontal plane when the insertable midsole orthotic is upright and in an unloaded condition.

11. The orthotic inner shoe as claimed in claim 8, wherein each said concavely rounded side portion further comprises a concavely rounded portion of the outer surface of the insertable midsole orthotic, as viewed in a horizontal plane when the insertable midsole orthotic is upright and in an unloaded condition, said concavity of the concavely rounded portion of the outer surface being determined relative to an inner section of the insertable midsole orthotic directly adjacent to the concavely rounded outer surface portion.

12. The orthotic inner shoe as claimed in claim 1, further comprising an insole.

13. The orthotic inner shoe as claimed in claim 1, wherein said device is an upper.

14. A shoe comprising:
   a shoe upper and a shoe sole including at least a bottom sole;
   at least a portion of said shoe sole being formed by an orthotic inner shoe as claimed in claim 1;
   at least a portion of the side of said shoe upper being attached directly to the bottom sole such that the shoe upper abuts at least a portion of the outer surface of the orthotic inner shoe when said orthotic inner shoe is inserted into the shoe; and
   wherein said orthotic inner shoe is removable from the shoe and insertable into said shoe through an opening in the shoe upper provided for entry and exit of an intended wearer's foot into and out of said shoe.

15. A shoe as claimed in claim 14, wherein said orthotic inner shoe is releasably secured to said shoe by a releasable securing structure selected from the group consisting of mechanical fasteners, a snap fit, interlocking geometries and combinations thereof.

16. An insertable midsole orthotic sized to fit inside a shoe and form part of the shoe designed to received and retain said insertable midsole orthotic, which comprises:
   an inner surface and an outer surface which together define an insertable midsole orthotic having a lateral side, a medial side and a middle portion located between the lateral and medial sides;
   a plurality of protrusions on at least one side of said insertable midsole orthotic that interact with the shoe to retain said insertable midsole orthotic in said shoe;
   at least one portion of the outer surface of each said protrusion is concavely rounded relative to an inner section of the insertable midsole orthotic directly adjacent to the concavely rounded outer surface portion, as viewed in a frontal plane cross-section when the insertable midsole orthotic is upright and in an unloaded condition;
   at least one portion of an inner surface of a side of the insertable midsole orthotic is convexly rounded relative to a section of the insertable midsole orthotic directly adjacent to the convexly rounded inner surface portion, as viewed in a frontal plane cross-section when the insertable midsole orthotic is upright and-in an unloaded condition; and
   wherein said insertable midsole orthotic is removable from said shoe.

17. An insertable midsole orthotic as claimed in claim 16, wherein said at least one said protrusion is located on the lateral side of the insertable midsole orthotic and another of said protrusions is located on the medial side of the insertable midsole orthotic.

18. The insertable midsole orthotic as claimed in claim 16, wherein each at least one convexly rounded inner surface portion and each at least one concavely rounded outer surface portion is located at a corresponding location on the insertable midsole orthotic to thereby form at least one of said protrusions.

19. The insertable midsole orthotic as claimed in claim 18, wherein each said protrusion is located at a location on the insertable midsole orthotic which corresponds to the position of at least one of the following parts of an intended wearer's foot when inside the insertable midsole orthotic: a base of a calcaneus, a lateral tuberosity of the calcaneus, a head of a first distal phalange, a longitudinal arch, a head of a first metatarsal, a head of a fifth metatarsal, and a base of the fifth metatarsal.

20. The insertable midsole orthotic as claimed in claim 19, wherein a thickness of the insertable midsole orthotic tapers from a greater thickness measured at each said protrusion to a lesser thickness at a location on one side of each said protrusion, as viewed in a horizontal plane when the insertable midsole orthotic is upright and in an unloaded condition.

21. The insertable midsole orthotic as claimed in claim 20, wherein the thickness of the insertable midsole orthotic tapers to a lesser thickness on both sides of each said protrusion, as viewed in a horizontal plane when the insertable midsole orthotic is upright and in an unloaded condition.

22. The insertable midsole orthotic as claimed in claim 18, further comprising an indentation located between said two protrusions, as viewed in a horizontal plane when the insertable midsole orthotic is upright and in an unloaded condition.

23. A shoe comprising:
   a shoe upper and a shoe sole including at least a bottom sole;
   at least a portion of said shoe sole being formed by an insertable midsole orthotic as claimed in claim 16;
   at least a portion of the side of said shoe upper being attached directly to the bottom sole such that the shoe upper abuts at least a portion of the outer surface of the insertable midsole orthotic when said insertable midsole orthotic is inserted into the shoe; and
   wherein said insertable midsole orthotic is removable from the shoe and insertable into said shoe through an opening in the shoe upper provided for entry and exit of an intended wearer's foot into and out of said shoe.

24. A shoe as claimed in claim 23, wherein the at least two protrusions on the side of the insertable midsole orthotic are in abutting relationship with the bottom sole when the insertable midsole orthotic is inside the shoe, so that the protrusions occupy corresponding recesses in the bottom sole to thereby releasably retain said insertable midsole orthotic in said shoe.

25. A shoe as claimed in claim 24, wherein a thickness of the insertable midsole orthotic tapers from a greater thickness measured at one said protrusion to a lesser thickness at a location on one side of said protrusion, as viewed in a horizontal plane when the insertable midsole orthotic is upright and in an unloaded condition.

26. A shoe as claimed in claim 25, wherein at least one portion of the outer surface of a side of the insertable midsole orthotic is concavely rounded relative to an inner section of the insertable midsole orthotic directly adjacent to the concavely rounded outer surface portion, as viewed in a frontal plane cross-section when the insertable midsole orthotic is upright and in an unloaded condition.

27. A shoe as claimed in claim 26, wherein at least one portion of an inner surface of a side of the insertable midsole orthotic is convexly rounded relative to a section of the insertable midsole orthotic directly adjacent to the convexly rounded inner surface portion, as viewed in a frontal plane cross-section when the insertable midsole orthotic is upright and in an unloaded condition.

28. A shoe as claimed in claim 27, wherein each at least one convexly rounded inner surface portion and each at least one concavely rounded outer surface portion is located at a corresponding location on the insertable midsole orthotic to thereby form at least one of said protrusions.

29. A shoe as claimed in claim 28, wherein each said protrusion is located at a location on the insertable midsole orthotic which corresponds to the position of at least one of the following parts of an intended wearer's foot when inside the insertable midsole orthotic: a base of a calcaneus, a lateral tuberosity of the calcaneus, a head of a first distal phalange, a longitudinal arch, a head of a first metatarsal, a head of a fifth metatarsal, and a base of the fifth metatarsal.

* * * * *

UNITED STATES PATENT AND TRADEMARK OFFICE
CERTIFICATE OF CORRECTION

PATENT NO.       : 7,010,869 B1                                        Page 1 of 4
APPLICATION NO.  : 09/558629
DATED            : March 14, 2006
INVENTOR(S)      : Frampton E. Ellis, III It is certified that error appears in the above-identified patent and that said Letters Patent is hereby corrected as shown below:

On the Front Cover, published figure (75A) should be replaced with figure (11R) as follows:

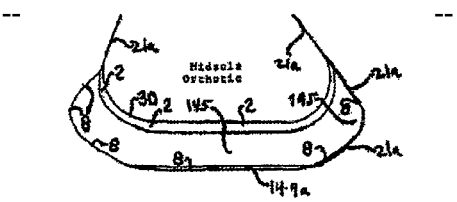

In the Drawings, Sheet 10, the unnumbered "Fig." should read --Fig. 11L--.
In the Drawings, Sheet 63, "Fig. 75A" should be labeled as --Prior Art--.
Column 20, line 27, "Fig. 11G" should be changed to --Fig. 11J--.
Column 20, line 28, "Fig. 11H" should be changed to --Fig.11I--.
Column 20, line 29, "Figs. 11I and 11J" should be changed to --Figs. 11H and 11G--.

Signed and Sealed this

Twenty-first Day of November, 2006

JON W. DUDAS
*Director of the United States Patent and Trademark Office*

United States Patent
Ellis, III

(12) United States Patent
(10) Patent No.: US 7,010,869 B1
(45) Date of Patent: Mar. 14, 2006

(54) SHOE SOLE ORTHOTIC STRUCTURES AND COMPUTER CONTROLLED COMPARTMENTS

(75) Inventor: Frampton E. Ellis, III, 2895 S. Abingdon St., Suite B2, Arlington, VA (US) 22206-1331

(73) Assignee: Frampton E. Ellis, III, Jasper, FL (US)

( * ) Notice: Subject to any disclaimer, the term of this patent is extended or adjusted under 35 U.S.C. 154(b) by 638 days.

(21) Appl. No.: 09/558,629

(22) Filed: Apr. 26, 2000

Related U.S. Application Data

(63) Continuation-in-part of application No. 09/358,848, filed on Jul. 22, 1999, now abandoned.
(60) Provisional application No. 60/139,319, filed on Jun. 15, 1999, provisional application No. 60/138,624, filed on Jun. 11, 1999, provisional application No. 60/133,114, filed on May 7, 1999, provisional application No. 60/131,255, filed on Apr. 27, 1999, and provisional application No. 60/130,990, filed on Apr. 26, 1999.

(51) Int. Cl.
*A43B 17/00* (2006.01)
*A43B 19/00* (2006.01)
*A43B 7/14* (2006.01)
*A61F 5/14* (2006.01)

(52) U.S. Cl. .................. 36/25 R; 36/88; 36/101; 36/100; 36/146; 36/161; 36/10

(58) Field of Classification Search ............ 36/25 R, 36/29, 32 R, 43, 22 R, 30 R, 31, 100, 101, 36/15, 103, 7.1 R, 7.2, 7.4, 7.7, 146, 161, 36/163, 88, 117.1, 117.4, 10
See application file for complete search history.

(56) References Cited

U.S. PATENT DOCUMENTS

| | | | |
|---|---|---|---|
| 597,524 A | 1/1898 | Molloy et al. | |
| 3,005,272 A | 10/1961 | Shelare et al. | |
| 4,263,728 A | 4/1981 | Frecentese | |

(Continued)

FOREIGN PATENT DOCUMENTS

| EP | 0 679 377 | 11/1995 |
| EP | 0 864 263 | 9/1998 |
| WO | 9000358 | 1/1990 |

(Continued)

OTHER PUBLICATIONS

Converse advertisement in box of shoes purchased in 1999, *Coming Spring 2000—Helium Cross Training*, 1 page.
L.L. Bean Catalog, Summer 1992, p. 122, Catalog entry for Birkenstock Sandals for Men and Women.

(Continued)

*Primary Examiner*—Anthony D. Stashick
(74) *Attorney, Agent, or Firm*—Knoble Yoshida & Dunleavy, LLC

(57) ABSTRACT

This invention relates generally to footwear with a shoe sole, including at least one insertable midsole orthotic. The insertable midsole orthotic is removably inserted within the shoe upper, the sides of which hold it in position. The shoe sole includes a concavely rounded side or underneath portion, which may be formed in part by the insertable midsole orthotic. The insertable midsole orthotic may extend the length of the shoe sole or may form only a part of the shoe sole and can incorporate cushioning or structural compartments or components.

The insertable midsole orthotic permits replacement of midsole material which has degraded or has worn out in order to maintain optimal characteristics of the shoe sole and allows customization for the individual wearer to provide tailored cushioning or support characteristics for the purpose of orthopedic, podiatric, corrective, prescriptive, therapeutic and/or prosthetic purposes.

29 Claims, 63 Drawing Sheets